(12) United States Patent
Richard et al.

(10) Patent No.: US 12,004,749 B2
(45) Date of Patent: *Jun. 11, 2024

(54) ADAPTER, EXTENSION, AND CONNECTOR ASSEMBLIES FOR SURGICAL DEVICES

(71) Applicant: Covidien LP, Mansfield, MA (US)

(72) Inventors: Paul Richard, Shelton, CT (US); Ramiro Cabrera, Cheshire, CT (US); Stephen Paul, Burlington, CT (US); Jonathan Sapienza, Orange, CT (US)

(73) Assignee: Covidien LP, Mansfield, MA (US)

( * ) Notice: Subject to any disclaimer, the term of this patent is extended or adjusted under 35 U.S.C. 154(b) by 263 days.

This patent is subject to a terminal disclaimer.

(21) Appl. No.: 17/392,654

(22) Filed: Aug. 3, 2021

(65) Prior Publication Data

US 2021/0361289 A1 Nov. 25, 2021

Related U.S. Application Data

(60) Continuation of application No. 16/448,139, filed on Jun. 21, 2019, now Pat. No. 11,083,462, which is a
(Continued)

(51) Int. Cl.
*A61B 17/115* (2006.01)
*A61B 17/34* (2006.01)
*A61B 17/00* (2006.01)

(52) U.S. Cl.
CPC .......... *A61B 17/1155* (2013.01); *A61B 17/34* (2013.01); *A61B 2017/00398* (2013.01);
(Continued)

(58) Field of Classification Search
CPC ...... A61B 17/1155; A61B 2017/00398; A61B 2017/0046; A61B 2017/00473; A61B 2017/00477; A61B 17/068
See application file for complete search history.

(56) References Cited

U.S. PATENT DOCUMENTS

| | | | |
|---|---|---|---|
| 2,777,340 A | 1/1957 | Hettwer et al. | |
| 2,957,353 A | 10/1960 | Babacz | |

(Continued)

FOREIGN PATENT DOCUMENTS

| | | |
|---|---|---|
| CA | 2451558 A1 | 1/2003 |
| CA | 2824590 A1 | 4/2014 |

(Continued)

OTHER PUBLICATIONS

European Office Action dated Sep. 21, 2017 corresponding to counterpart Patent Application EP 16 164 391.1.
(Continued)

*Primary Examiner* — Michelle Lopez
(74) *Attorney, Agent, or Firm* — Carter, DeLuca & Farrell LLP

(57) ABSTRACT

An adapter assembly for connecting an end effector to an electrosurgical instrument is provided. The adapter assembly includes a drive transfer assembly, first and second pusher assemblies, a drive member, an extension assembly, and a trocar assembly. The drive transfer assembly includes first, second and third rotatable shafts. Each pusher assembly is operably connected to a rotatable shaft for converting rotational motion from one rotatable shaft to longitudinal movement to perform a different function. The drive member is operably connected to the third rotatable shaft for transferring rotational motion from the third rotatable shaft to perform a third function. The extension assembly is operably connected to a distal end of the adapter assembly and includes at least one flexible band assembly operably connected to one of the first and second pusher assemblies. The trocar assembly is configured for releasable engagement with the extension assembly.

20 Claims, 31 Drawing Sheets

Related U.S. Application Data division of application No. 14/991,157, filed on Jan. 8, 2016, now Pat. No. 10,327,779.

(60) Provisional application No. 62/145,759, filed on Apr. 10, 2015.

(52) U.S. Cl.
CPC ............... *A61B 2017/0046* (2013.01); *A61B 2017/00473* (2013.01); *A61B 2017/00477* (2013.01)

(56) References Cited

U.S. PATENT DOCUMENTS

| | | |
|---|---|---|
| 3,111,328 A | 11/1963 | Di Rito et al. |
| 3,695,058 A | 10/1972 | Keith, Jr. |
| 3,734,515 A | 5/1973 | Dudek |
| 3,759,336 A | 9/1973 | Marcovitz et al. |
| 4,162,399 A | 7/1979 | Hudson |
| 4,606,343 A | 8/1986 | Conta et al. |
| 4,705,038 A | 11/1987 | Sjostrom et al. |
| 4,722,685 A | 2/1988 | de Estrada et al. |
| 4,823,807 A | 4/1989 | Russell et al. |
| 4,874,181 A | 10/1989 | Hsu |
| 5,129,118 A | 7/1992 | Walmesley |
| 5,129,570 A | 7/1992 | Schulze et al. |
| 5,152,744 A | 10/1992 | Krause et al. |
| 5,301,061 A | 4/1994 | Nakada et al. |
| 5,312,023 A | 5/1994 | Green et al. |
| 5,326,013 A | 7/1994 | Green et al. |
| 5,333,773 A * | 8/1994 | Main ................... A61B 17/115 227/19 |
| 5,350,355 A | 9/1994 | Sklar |
| 5,383,874 A | 1/1995 | Jackson et al. |
| 5,383,880 A | 1/1995 | Hooven |
| 5,389,098 A | 2/1995 | Tsuruta et al. |
| 5,395,033 A | 3/1995 | Byrne et al. |
| 5,400,267 A | 3/1995 | Denen et al. |
| 5,411,508 A | 5/1995 | Bessler et al. |
| 5,413,267 A | 5/1995 | Solyntjes et al. |
| 5,427,087 A | 6/1995 | Ito et al. |
| 5,433,721 A | 7/1995 | Hooven et al. |
| 5,464,415 A | 11/1995 | Chen |
| 5,467,911 A | 11/1995 | Tsuruta et al. |
| 5,476,379 A | 12/1995 | Disel |
| 5,487,499 A | 1/1996 | Sorrentino et al. |
| 5,518,163 A | 5/1996 | Hooven |
| 5,518,164 A | 5/1996 | Hooven |
| 5,526,822 A | 6/1996 | Burbank et al. |
| 5,529,235 A | 6/1996 | Boiarski et al. |
| 5,535,934 A | 7/1996 | Boiarski et al. |
| 5,535,937 A | 7/1996 | Boiarski et al. |
| 5,540,375 A | 7/1996 | Bolanos et al. |
| 5,540,706 A | 7/1996 | Aust et al. |
| 5,542,594 A | 8/1996 | Mckean et al. |
| 5,549,637 A | 8/1996 | Crainich |
| 5,553,675 A | 9/1996 | Pitzen et al. |
| 5,562,239 A | 10/1996 | Boiarski et al. |
| 5,564,615 A | 10/1996 | Bishop et al. |
| 5,609,560 A | 3/1997 | Ichikawa et al. |
| 5,626,587 A | 5/1997 | Bishop et al. |
| 5,632,432 A | 5/1997 | Schulze et al. |
| 5,645,209 A | 7/1997 | Green et al. |
| 5,647,526 A | 7/1997 | Green et al. |
| 5,653,374 A | 8/1997 | Young et al. |
| 5,658,300 A | 8/1997 | Bito et al. |
| 5,662,662 A | 9/1997 | Bishop et al. |
| 5,667,517 A | 9/1997 | Hooven |
| 5,669,918 A | 9/1997 | Balazs et al. |
| 5,693,042 A | 12/1997 | Boiarski et al. |
| 5,704,534 A | 1/1998 | Huitema et al. |
| 5,713,505 A | 2/1998 | Huitema |
| 5,762,603 A | 6/1998 | Thompson |
| 5,779,130 A | 7/1998 | Alesi et al. |
| 5,782,396 A | 7/1998 | Mastri et al. |
| 5,782,397 A | 7/1998 | Koukline |
| 5,792,573 A | 8/1998 | Pitzen et al. |
| 5,797,536 A | 8/1998 | Smith et al. |
| 5,810,863 A * | 9/1998 | Wolf ................ A61B 17/3417 606/167 |
| 5,820,009 A | 10/1998 | Melling et al. |
| 5,863,159 A | 1/1999 | Lasko |
| 5,908,427 A | 6/1999 | McKean et al. |
| 5,954,259 A | 9/1999 | Viola et al. |
| 5,964,774 A | 10/1999 | McKean et al. |
| 5,993,454 A | 11/1999 | Longo |
| 6,010,054 A | 1/2000 | Johnson et al. |
| 6,017,354 A | 1/2000 | Culp et al. |
| 6,032,849 A | 3/2000 | Mastri et al. |
| 6,045,560 A | 4/2000 | McKean et al. |
| 6,090,123 A | 7/2000 | Culp et al. |
| 6,126,651 A | 10/2000 | Mayer |
| 6,129,547 A | 10/2000 | Cise et al. |
| 6,165,169 A | 12/2000 | Panescu et al. |
| 6,239,732 B1 | 5/2001 | Cusey |
| 6,241,139 B1 | 6/2001 | Milliman et al. |
| 6,264,086 B1 | 7/2001 | McGuckin, Jr. |
| 6,264,087 B1 | 7/2001 | Whitman |
| 6,280,417 B1 * | 8/2001 | Bohannon .......... A61B 17/3496 604/167.03 |
| 6,302,311 B1 | 10/2001 | Adams et al. |
| 6,315,184 B1 | 11/2001 | Whitman |
| 6,321,855 B1 | 11/2001 | Barnes |
| 6,329,778 B1 | 12/2001 | Culp et al. |
| 6,343,731 B1 | 2/2002 | Adams et al. |
| 6,348,061 B1 | 2/2002 | Whitman |
| 6,368,324 B1 | 4/2002 | Dinger et al. |
| 6,371,909 B1 | 4/2002 | Hoeg et al. |
| 6,434,507 B1 | 8/2002 | Clayton et al. |
| 6,443,973 B1 | 9/2002 | Whitman |
| 6,461,372 B1 | 10/2002 | Jensen et al. |
| 6,488,197 B1 | 12/2002 | Whitman |
| 6,491,201 B1 | 12/2002 | Whitman |
| 6,533,157 B1 | 3/2003 | Whitman |
| 6,537,280 B2 | 3/2003 | Dinger et al. |
| 6,610,066 B2 | 8/2003 | Dinger et al. |
| 6,611,793 B1 | 8/2003 | Burnside et al. |
| 6,645,218 B1 | 11/2003 | Cassidy et al. |
| 6,654,999 B2 | 12/2003 | Stoddard et al. |
| 6,698,643 B2 | 3/2004 | Whitman |
| 6,699,177 B1 | 3/2004 | Wang et al. |
| 6,716,233 B1 | 4/2004 | Whitman |
| 6,743,240 B2 | 6/2004 | Smith et al. |
| 6,783,533 B2 | 8/2004 | Green et al. |
| 6,792,390 B1 | 9/2004 | Burnside et al. |
| 6,793,652 B1 | 9/2004 | Whitman et al. |
| 6,817,508 B1 | 11/2004 | Racenet et al. |
| 6,830,174 B2 | 12/2004 | Hillstead et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,860,892 B1 | 3/2005 | Tanaka et al. |
| 6,899,538 B2 | 5/2005 | Matoba |
| 6,905,057 B2 | 6/2005 | Swayze et al. |
| 6,959,852 B2 | 11/2005 | Shelton, IV et al. |
| 6,964,363 B2 | 11/2005 | Wales et al. |
| 6,981,628 B2 | 1/2006 | Wales |
| 6,981,941 B2 | 1/2006 | Whitman et al. |
| 6,986,451 B1 | 1/2006 | Mastri et al. |
| 6,988,649 B2 | 1/2006 | Shelton, IV et al. |
| 7,032,798 B2 | 4/2006 | Whitman et al. |
| RE39,152 E | 6/2006 | Aust et al. |
| 7,055,731 B2 | 6/2006 | Shelton, IV et al. |
| 7,059,508 B2 | 6/2006 | Shelton, IV et al. |
| 7,077,856 B2 | 7/2006 | Whitman |
| 7,111,769 B2 | 9/2006 | Wales et al. |
| 7,122,029 B2 | 10/2006 | Koop et al. |
| 7,140,528 B2 | 11/2006 | Shelton, IV |
| 7,141,049 B2 | 11/2006 | Stern et al. |
| 7,143,923 B2 | 12/2006 | Shelton, IV et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |

(56) References Cited

U.S. PATENT DOCUMENTS

| | | |
|---|---|---|
| 7,172,104 B2 | 2/2007 | Scirica et al. |
| 7,225,964 B2 | 6/2007 | Mastri et al. |
| 7,238,021 B1 | 7/2007 | Johnson |
| 7,246,734 B2 | 7/2007 | Shelton, IV |
| 7,252,660 B2 | 8/2007 | Kunz |
| 7,328,828 B2 | 2/2008 | Ortiz et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,422,139 B2 | 9/2008 | Shelton, IV et al. |
| 7,431,189 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,347 B2 | 1/2009 | Roy |
| 7,481,824 B2 | 1/2009 | Boudreaux et al. |
| 7,487,899 B2 | 2/2009 | Shelton, IV et al. |
| 7,549,564 B2 | 6/2009 | Boudreaux |
| 7,556,186 B2 | 7/2009 | Milliman |
| 7,565,993 B2 | 7/2009 | Milliman et al. |
| 7,568,603 B2 | 8/2009 | Shelton, IV et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,670,334 B2 | 3/2010 | Hueil et al. |
| 7,673,780 B2 | 3/2010 | Shelton, IV et al. |
| 7,699,835 B2 | 4/2010 | Lee et al. |
| 7,721,931 B2 | 5/2010 | Shelton, IV et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,758,613 B2 | 7/2010 | Whitman |
| 7,766,210 B2 | 8/2010 | Shelton, IV et al. |
| 7,770,773 B2 | 8/2010 | Whitman et al. |
| 7,770,775 B2 | 8/2010 | Shelton, IV et al. |
| 7,793,812 B2 | 9/2010 | Moore et al. |
| 7,799,039 B2 | 9/2010 | Shelton, IV et al. |
| 7,802,712 B2 | 9/2010 | Milliman et al. |
| 7,803,151 B2 | 9/2010 | Whitman |
| 7,822,458 B2 | 10/2010 | Webster et al. |
| 7,845,534 B2 | 12/2010 | Viola et al. |
| 7,845,537 B2 | 12/2010 | Shelton, IV et al. |
| 7,857,185 B2 | 12/2010 | Swayze et al. |
| 7,870,989 B2 | 1/2011 | Viola et al. |
| 7,900,805 B2 | 3/2011 | Shelton, IV et al. |
| 7,905,897 B2 | 3/2011 | Whitman et al. |
| 7,918,230 B2 | 4/2011 | Whitman et al. |
| 7,922,061 B2 | 4/2011 | Shelton, IV et al. |
| 7,922,719 B2 | 4/2011 | Ralph et al. |
| 7,947,034 B2 | 5/2011 | Whitman |
| 7,951,071 B2 | 5/2011 | Whitman et al. |
| 7,954,682 B2 | 6/2011 | Giordano et al. |
| 7,959,051 B2 | 6/2011 | Smith et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,992,758 B2 | 8/2011 | Whitman et al. |
| 8,011,550 B2 | 9/2011 | Aranyi et al. |
| 8,016,178 B2 | 9/2011 | Olson et al. |
| 8,016,855 B2 | 9/2011 | Whitman et al. |
| 8,020,743 B2 | 9/2011 | Shelton, IV |
| 8,025,199 B2 | 9/2011 | Whitman et al. |
| 8,035,487 B2 | 10/2011 | Malackowski |
| 8,052,024 B2 | 11/2011 | Viola et al. |
| 8,114,118 B2 | 2/2012 | Knodel et al. |
| 8,127,975 B2 | 3/2012 | Olson et al. |
| 8,132,705 B2 | 3/2012 | Viola et al. |
| 8,152,516 B2 | 4/2012 | Harvey et al. |
| 8,157,150 B2 | 4/2012 | Viola et al. |
| 8,157,151 B2 | 4/2012 | Ingmanson et al. |
| 8,182,494 B1 | 5/2012 | Yencho et al. |
| 8,186,555 B2 | 5/2012 | Shelton, IV et al. |
| 8,186,587 B2 | 5/2012 | Zmood et al. |
| 8,220,367 B2 | 7/2012 | Hsu |
| 8,235,273 B2 | 8/2012 | Olson et al. |
| 8,241,322 B2 | 8/2012 | Whitman et al. |
| 8,272,554 B2 | 9/2012 | Whitman et al. |
| 8,292,150 B2 | 10/2012 | Bryant |
| 8,292,888 B2 | 10/2012 | Whitman |
| 8,342,379 B2 | 1/2013 | Whitman et al. |
| 8,348,130 B2 | 1/2013 | Shah et al. |
| 8,348,855 B2 | 1/2013 | Hillely et al. |
| 8,353,440 B2 | 1/2013 | Whitman et al. |
| 8,357,144 B2 | 1/2013 | Whitman et al. |
| 8,365,633 B2 | 2/2013 | Simaan et al. |
| 8,365,972 B2 | 2/2013 | Aranyi et al. |
| 8,371,492 B2 | 2/2013 | Aranyi et al. |
| 8,372,057 B2 | 2/2013 | Cude et al. |
| 8,391,957 B2 | 3/2013 | Carlson et al. |
| 8,403,926 B2 | 3/2013 | Nobis et al. |
| 8,418,904 B2 | 4/2013 | Wenchell et al. |
| 8,424,739 B2 | 4/2013 | Racenet et al. |
| 8,454,585 B2 | 6/2013 | Whitman |
| 8,505,802 B2 | 8/2013 | Viola et al. |
| 8,517,241 B2 | 8/2013 | Nicholas et al. |
| 8,523,043 B2 | 9/2013 | Ullrich et al. |
| 8,551,076 B2 | 10/2013 | Duval et al. |
| 8,561,871 B2 | 10/2013 | Rajappa et al. |
| 8,561,874 B2 | 10/2013 | Scirica |
| 8,590,763 B2 | 11/2013 | Milliman |
| 8,602,287 B2 | 12/2013 | Yates et al. |
| 8,623,000 B2 | 1/2014 | Humayun et al. |
| 8,627,995 B2 | 1/2014 | Smith et al. |
| 8,632,463 B2 | 1/2014 | Drinan et al. |
| 8,636,766 B2 | 1/2014 | Milliman et al. |
| 8,647,258 B2 | 2/2014 | Aranyi et al. |
| 8,652,121 B2 | 2/2014 | Quick et al. |
| 8,657,174 B2 | 2/2014 | Yates et al. |
| 8,657,177 B2 | 2/2014 | Scirica et al. |
| 8,672,206 B2 | 3/2014 | Aranyi et al. |
| 8,696,552 B2 | 4/2014 | Whitman |
| 8,708,213 B2 | 4/2014 | Shelton, IV et al. |
| 8,715,306 B2 | 5/2014 | Faller et al. |
| 8,758,391 B2 | 6/2014 | Swayze et al. |
| 8,806,973 B2 | 8/2014 | Ross et al. |
| 8,808,311 B2 | 8/2014 | Heinrich et al. |
| 8,820,605 B2 | 9/2014 | Shelton, IV |
| 8,851,355 B2 | 10/2014 | Aranyi et al. |
| 8,858,571 B2 | 10/2014 | Shelton, IV et al. |
| 8,875,972 B2 | 11/2014 | Weisenburgh et al. |
| 8,888,762 B2 | 11/2014 | Whitman |
| 8,893,946 B2 | 11/2014 | Boudreaux et al. |
| 8,899,462 B2 | 12/2014 | Kostrzewski et al. |
| 8,905,289 B2 | 12/2014 | Patel et al. |
| 8,910,847 B2 | 12/2014 | Nalagatla et al. |
| 8,919,630 B2 | 12/2014 | Milliman |
| 8,931,680 B2 | 1/2015 | Milliman |
| 8,939,344 B2 | 1/2015 | Olson et al. |
| 8,950,646 B2 | 2/2015 | Viola |
| 8,960,519 B2 | 2/2015 | Whitman et al. |
| 8,961,396 B2 | 2/2015 | Azarbarzin et al. |
| 8,967,443 B2 | 3/2015 | McCuen |
| 8,968,276 B2 | 3/2015 | Zemlok et al. |
| 8,968,337 B2 | 3/2015 | Whitfield et al. |
| 8,992,422 B2 | 3/2015 | Spivey et al. |
| 9,016,545 B2 | 4/2015 | Aranyi et al. |
| 9,023,014 B2 | 5/2015 | Chowaniec et al. |
| 9,033,868 B2 | 5/2015 | Whitman et al. |
| 9,055,943 B2 | 6/2015 | Zemlok et al. |
| 9,064,653 B2 | 6/2015 | Prest et al. |
| 9,072,515 B2 | 7/2015 | Hall et al. |
| 9,113,847 B2 | 8/2015 | Whitman et al. |
| 9,113,875 B2 | 8/2015 | Viola et al. |
| 9,113,876 B2 | 8/2015 | Zemlok et al. |
| 9,113,899 B2 | 8/2015 | Garrison et al. |

(56) References Cited

U.S. PATENT DOCUMENTS

| | | |
|---|---|---|
| 9,216,013 B2 | 12/2015 | Scirica et al. |
| 9,282,961 B2 | 3/2016 | Whitman et al. |
| 9,282,963 B2 | 3/2016 | Bryant |
| 9,295,522 B2 | 3/2016 | Kostrzewski |
| 9,307,986 B2 | 4/2016 | Hall et al. |
| 9,579,099 B2 | 2/2017 | Penna et al. |
| 10,327,779 B2 | 6/2019 | Richard et al. |
| 10,463,365 B2 | 11/2019 | Williams |
| 10,485,549 B2 | 11/2019 | Williams et al. |
| 10,561,417 B2 | 2/2020 | Zergiebel et al. |
| 11,083,462 B2 | 8/2021 | Richard et al. |
| 2001/0031975 A1 | 10/2001 | Whitman et al. |
| 2002/0049454 A1 | 4/2002 | Whitman et al. |
| 2002/0165541 A1 | 11/2002 | Whitman |
| 2003/0038938 A1 | 2/2003 | Jung et al. |
| 2003/0165794 A1 | 9/2003 | Matoba |
| 2004/0111012 A1 | 6/2004 | Whitman |
| 2004/0133189 A1 | 7/2004 | Sakurai |
| 2004/0153124 A1 | 8/2004 | Whitman |
| 2004/0176751 A1 | 9/2004 | Weitzner et al. |
| 2004/0193146 A1 | 9/2004 | Lee et al. |
| 2005/0125027 A1 | 6/2005 | Knodel et al. |
| 2005/0131442 A1 | 6/2005 | Yachia et al. |
| 2006/0142656 A1 | 6/2006 | Malackowski et al. |
| 2006/0142740 A1 | 6/2006 | Sherman et al. |
| 2006/0142744 A1 | 6/2006 | Boutoussov |
| 2006/0259073 A1 | 11/2006 | Miyamoto et al. |
| 2006/0278680 A1 | 12/2006 | Viola et al. |
| 2006/0284730 A1 | 12/2006 | Schmid et al. |
| 2007/0023476 A1 | 2/2007 | Whitman et al. |
| 2007/0023477 A1 | 2/2007 | Whitman et al. |
| 2007/0029363 A1 | 2/2007 | Popov |
| 2007/0084897 A1 | 4/2007 | Shelton et al. |
| 2007/0102472 A1 | 5/2007 | Shelton |
| 2007/0152014 A1 | 7/2007 | Gillum et al. |
| 2007/0175947 A1 | 8/2007 | Ortiz et al. |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0175961 A1 | 8/2007 | Shelton et al. |
| 2007/0270784 A1 | 11/2007 | Smith et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0058801 A1 | 3/2008 | Taylor et al. |
| 2008/0109012 A1 | 5/2008 | Falco et al. |
| 2008/0110958 A1 | 5/2008 | McKenna et al. |
| 2008/0147089 A1 | 6/2008 | Loh et al. |
| 2008/0167736 A1 | 7/2008 | Swayze et al. |
| 2008/0185419 A1 | 8/2008 | Smith et al. |
| 2008/0188841 A1 | 8/2008 | Tomasello et al. |
| 2008/0197167 A1 | 8/2008 | Viola et al. |
| 2008/0208195 A1 | 8/2008 | Shores et al. |
| 2008/0228213 A1* | 9/2008 | Blakeney ............ A61B 17/3421 606/185 |
| 2008/0237296 A1 | 10/2008 | Boudreaux et al. |
| 2008/0251561 A1 | 10/2008 | Eades et al. |
| 2008/0255413 A1 | 10/2008 | Zemlok et al. |
| 2008/0255607 A1 | 10/2008 | Zemlok |
| 2008/0262654 A1 | 10/2008 | Omori et al. |
| 2008/0308603 A1 | 12/2008 | Shelton et al. |
| 2009/0012533 A1 | 1/2009 | Barbagli et al. |
| 2009/0090763 A1 | 4/2009 | Zemlok et al. |
| 2009/0099876 A1 | 4/2009 | Whitman |
| 2009/0138006 A1 | 5/2009 | Bales et al. |
| 2009/0171147 A1 | 7/2009 | Lee et al. |
| 2009/0182193 A1 | 7/2009 | Whitman et al. |
| 2009/0209990 A1 | 8/2009 | Yates et al. |
| 2009/0254094 A1 | 10/2009 | Knapp et al. |
| 2009/0299141 A1 | 12/2009 | Downey et al. |
| 2010/0023022 A1 | 1/2010 | Zeiner et al. |
| 2010/0069942 A1 | 3/2010 | Shelton, IV |
| 2010/0108741 A1 | 5/2010 | Hessler et al. |
| 2010/0193568 A1 | 8/2010 | Scheib et al. |
| 2010/0211053 A1 | 8/2010 | Ross et al. |
| 2010/0225073 A1 | 9/2010 | Porter et al. |
| 2011/0071508 A1 | 3/2011 | Duval et al. |
| 2011/0077673 A1 | 3/2011 | Grubac et al. |
| 2011/0101065 A1* | 5/2011 | Milliman ............ A61B 17/068 227/175.1 |
| 2011/0121049 A1 | 5/2011 | Malinouskas et al. |
| 2011/0125138 A1 | 5/2011 | Malinouskas et al. |
| 2011/0139851 A1 | 6/2011 | McCuen |
| 2011/0155783 A1 | 6/2011 | Rajappa et al. |
| 2011/0155786 A1 | 6/2011 | Shelton, IV |
| 2011/0172648 A1 | 7/2011 | Jeong |
| 2011/0174099 A1 | 7/2011 | Ross et al. |
| 2011/0184245 A1 | 7/2011 | Xia et al. |
| 2011/0204119 A1 | 8/2011 | McCuen |
| 2011/0218522 A1 | 9/2011 | Whitman |
| 2011/0276057 A1 | 11/2011 | Conlon et al. |
| 2011/0290854 A1 | 12/2011 | Timm et al. |
| 2011/0290855 A1 | 12/2011 | Moore et al. |
| 2011/0295242 A1 | 12/2011 | Spivey et al. |
| 2011/0295269 A1 | 12/2011 | Swensgard et al. |
| 2012/0000962 A1 | 1/2012 | Racenet et al. |
| 2012/0074199 A1 | 3/2012 | Olson et al. |
| 2012/0089131 A1 | 4/2012 | Zemlok et al. |
| 2012/0104071 A1 | 5/2012 | Bryant |
| 2012/0116368 A1 | 5/2012 | Viola |
| 2012/0143002 A1 | 6/2012 | Aranyi et al. |
| 2012/0172924 A1 | 7/2012 | Allen, IV |
| 2012/0211542 A1 | 8/2012 | Racenet |
| 2012/0223121 A1 | 9/2012 | Viola et al. |
| 2012/0245428 A1 | 9/2012 | Smith et al. |
| 2012/0253329 A1 | 10/2012 | Zemlok et al. |
| 2012/0310220 A1 | 12/2012 | Malkowski et al. |
| 2012/0323226 A1 | 12/2012 | Chowaniec et al. |
| 2012/0330285 A1 | 12/2012 | Hartoumbekis et al. |
| 2013/0018361 A1 | 1/2013 | Bryant |
| 2013/0093149 A1 | 4/2013 | Saur et al. |
| 2013/0181029 A1 | 7/2013 | Milliman |
| 2013/0181035 A1 | 7/2013 | Milliman |
| 2013/0184704 A1 | 7/2013 | Beardsley et al. |
| 2013/0214025 A1 | 8/2013 | Zemlok et al. |
| 2013/0274722 A1 | 10/2013 | Kostrzewski et al. |
| 2013/0282052 A1 | 10/2013 | Aranyi et al. |
| 2013/0292451 A1 | 11/2013 | Viola et al. |
| 2013/0313304 A1 | 11/2013 | Shelton, IV et al. |
| 2013/0317486 A1 | 11/2013 | Nicholas et al. |
| 2013/0319706 A1 | 12/2013 | Nicholas et al. |
| 2013/0324978 A1 | 12/2013 | Nicholas et al. |
| 2013/0324979 A1 | 12/2013 | Nicholas et al. |
| 2013/0334281 A1 | 12/2013 | Williams |
| 2014/0012236 A1 | 1/2014 | Williams et al. |
| 2014/0012237 A1 | 1/2014 | Pribanic et al. |
| 2014/0012289 A1 | 1/2014 | Snow et al. |
| 2014/0025046 A1 | 1/2014 | Williams et al. |
| 2014/0110455 A1 | 4/2014 | Ingmanson et al. |
| 2014/0207125 A1 | 7/2014 | Applegate et al. |
| 2014/0207182 A1 | 7/2014 | Zergiebel et al. |
| 2014/0207185 A1 | 7/2014 | Goble et al. |
| 2014/0236173 A1 | 8/2014 | Scirica et al. |
| 2014/0236174 A1 | 8/2014 | Williams et al. |
| 2014/0276932 A1 | 9/2014 | Williams et al. |
| 2014/0299647 A1 | 10/2014 | Scirica et al. |
| 2014/0303668 A1 | 10/2014 | Nicholas et al. |
| 2014/0352463 A1 | 12/2014 | Parihar |
| 2014/0358129 A1 | 12/2014 | Zergiebel et al. |
| 2014/0361068 A1 | 12/2014 | Aranyi et al. |
| 2014/0365235 A1 | 12/2014 | DeBoer et al. |
| 2014/0373652 A1 | 12/2014 | Zergiebel et al. |
| 2015/0014392 A1 | 1/2015 | Williams et al. |
| 2015/0048144 A1 | 2/2015 | Whitman |
| 2015/0076205 A1 | 3/2015 | Zergiebel |
| 2015/0080912 A1 | 3/2015 | Sapre |
| 2015/0108201 A1 | 4/2015 | Williams |
| 2015/0112381 A1 | 4/2015 | Richard |
| 2015/0122870 A1 | 5/2015 | Zemlok et al. |
| 2015/0133224 A1 | 5/2015 | Whitman et al. |
| 2015/0133957 A1 | 5/2015 | Kostrzewski |
| 2015/0150547 A1 | 6/2015 | Ingmanson et al. |

(56) References Cited

U.S. PATENT DOCUMENTS

| | | |
|---|---|---|
| 2015/0150574 A1 | 6/2015 | Richard et al. |
| 2015/0157320 A1 | 6/2015 | Zergiebel et al. |
| 2015/0157321 A1 | 6/2015 | Zergiebel et al. |
| 2015/0164502 A1 | 6/2015 | Richard et al. |
| 2015/0190133 A1 | 7/2015 | Penna et al. |
| 2015/0201931 A1 | 7/2015 | Zergiebel et al. |
| 2015/0272577 A1 | 10/2015 | Zemlok et al. |
| 2015/0297199 A1 | 10/2015 | Nicholas et al. |
| 2015/0303996 A1 | 10/2015 | Calderoni |
| 2015/0320420 A1 | 11/2015 | Penna et al. |
| 2015/0327850 A1 | 11/2015 | Kostrzewski |
| 2015/0342601 A1 | 12/2015 | Williams et al. |
| 2015/0342603 A1 | 12/2015 | Zergiebel et al. |
| 2015/0374366 A1 | 12/2015 | Zergiebel et al. |
| 2015/0374370 A1 | 12/2015 | Zergiebel et al. |
| 2015/0374371 A1 | 12/2015 | Richard et al. |
| 2015/0374372 A1 | 12/2015 | Zergiebel et al. |
| 2015/0374449 A1 | 12/2015 | Chowaniec et al. |
| 2015/0380187 A1 | 12/2015 | Zergiebel et al. |
| 2016/0095585 A1 | 4/2016 | Zergiebel et al. |
| 2016/0095596 A1 | 4/2016 | Scirica et al. |
| 2016/0106406 A1 | 4/2016 | Cabrera |
| 2016/0113648 A1 | 4/2016 | Zergiebel et al. |
| 2016/0113649 A1 | 4/2016 | Zergiebel et al. |

FOREIGN PATENT DOCUMENTS

| | | | |
|---|---|---|---|
| CN | 102247182 A | 11/2011 | |
| DE | 102008053842 A1 | 5/2010 | |
| EP | 0705571 A1 | 4/1996 | |
| EP | 1769754 A1 | 4/2007 | |
| EP | 2055243 A2 | 5/2009 | |
| EP | 2316345 A1 | 5/2011 | |
| EP | 2333509 A1 | 6/2011 | |
| EP | 2505144 A1 | 10/2012 | |
| EP | 2668910 A2 | 12/2013 | |
| EP | 3011915 A2 | 4/2016 | |
| EP | 3078335 A1 * | 10/2016 | ......... A61B 17/1155 |
| ES | 2333509 A1 | 2/2010 | |
| JP | 08038488 | 2/1996 | |
| JP | 2005125075 A | 5/2005 | |
| KR | 20120022521 A | 3/2012 | |
| WO | 2011108840 A2 | 9/2011 | |
| WO | 2012040984 A1 | 4/2012 | |
| WO | 2013059432 A1 | 4/2013 | |
| WO | 2014139442 A1 | 9/2014 | |

OTHER PUBLICATIONS

Chinese Office Action dated Feb. 11, 2023, issued in corresponding CN Appln. No. 202010429218, 6 pages.
Chinese First Office Action dated Nov. 6, 2019 corresponding to counterpart Patent Application CN 201610222068.3.
Japanese Office Action dated Dec. 11, 2019 corresponding to counterpart Patent Application JP 2016-075076.
Japanese Notice of Allowance corresponding to counterpart Patent Application No. JP 2016-075076 dated Aug. 4, 2020; and machine generated English Translation.
Extended European Search Report corresponding to counterpart International Application No. EP 14 18 4882.0 dated May 12, 2015.
Canadian Office Action corresponding to counterpart International Application No. CA 2640399 dated May 7, 2015.
Japanese Office Action corresponding to counterpart International Application No. JP 2011-197365 dated Mar. 23, 2015.
Japanese Office Action corresponding to counterpart International Application No. JP 2011-084092 dated May 20, 2015.
Japanese Office Action corresponding to counterpart International Application No. JP 2014-148482 dated Jun. 2, 2015.
Extended European Search Report corresponding to counterpart International Application No. EP 14 18 9358.6 dated Jul. 8, 2015.
Extended European Search Report corresponding to counterpart International Application No. EP 14 19 61482 dated Apr. 23, 2015.
Partial European Search Report corresponding to counterpart International Application No. EP 14 19 6704.2 dated May 11, 2015.
Australian Office Action corresponding to counterpart International Application No. AU 2010241367 dated Aug. 20, 2015.
Partial European Search Report corresponding to counterpart International Application No. EP 14 19 97833 dated Sep. 3, 2015.
Extended European Search Report corresponding to counterpart International Application No. EP 15 16 9962.6 dated Sep. 14, 2015.
Extended European Search Report corresponding to counterpart Int'l Appln. No. EP 16 16 43911 dated Aug. 16, 2016.
Extended European Search Report corresponding to International Application No. EP 15 15 1076.5 dated Apr. 22, 2015.
Japanese Office Action corresponding to International Application No. JP 2011-084092 dated Jan. 14, 2016.
Extended European Search Report corresponding to International Application No. EP 12 19 79702 dated Jan. 28, 2016.
Chinese Office Action corresponding to International Application No. CN 201210560638.1 dated Oct. 21, 2015.
European Office Action corresponding to International Application No. EP 14 15 9056.2 dated Oct. 26, 2015.
Australian Examination Report No. 1 corresponding to International Application No. AU 2015200153 dated Dec. 11, 2015.
Australian Examination Report No. 1 corresponding to International Application No. AU 2014204542 dated Jan. 7, 2016.
Chinese Office Action corresponding to International Application No. CN 201310125449.6 dated Feb. 3, 2016.
Extended European Search Report corresponding to International Application No. EP 15 19 0245.9 dated Jan. 28, 2016.
Extended European Search Report corresponding to International Application No. EP 15 16 7793.7 dated Apr. 5, 2016.
European Office Action corresponding to International Application No. EP 14 18 4882.0 dated Apr. 25, 2016.
Extended European Search Report corresponding to International Application No. EP 14 19 6704.2 dated Sep. 24, 2015.
International Search Report and Written Opinion corresponding to Int'l Appln. No. PCT/US2015/051837, dated Dec. 21, 2015.
Extended European Search Report corresponding to International Application No. EP 14 19 7563.1 dated Aug. 5, 2015.
Partial European Search Report corresponding to International Application No. EP 15 19 0643.5 dated Feb. 26, 2016.
Extended European Search Report corresponding to International Application No. EP 15 16 6899.3 dated Feb. 3, 2016.
Extended European Search Report corresponding to International Application No. EP 14 19 9783.3 dated Dec. 22, 2015.
Extended European Search Report corresponding to International Application No. EP 15 17 3807.7 dated Nov. 24, 2015.
Extended European Search Report corresponding to International Application No. EP 15 19 0760.7 dated Apr. 1, 2016.
Extended European Search Report corresponding to International Application No. EP 15 17 3803.6 dated Nov. 24, 2015.
Extended European Search Report corresponding to International Application No. EP 15 17 3804.4 dated Nov. 24, 2015.
Extended European Search Report corresponding to International Application No. EP 15 18 8539.9 dated Feb. 17, 2016.
Extended European Search Report corresponding to International Application No. EP 15 17 3910.9 dated Nov. 13, 2015.
European Office Action corresponding to International Application No. EP 14 15 2236.7 dated Aug. 11, 2015.
Extended European Search Report corresponding to International Application No. EP 15 18 4915.5 dated Jan. 5, 2016.

* cited by examiner

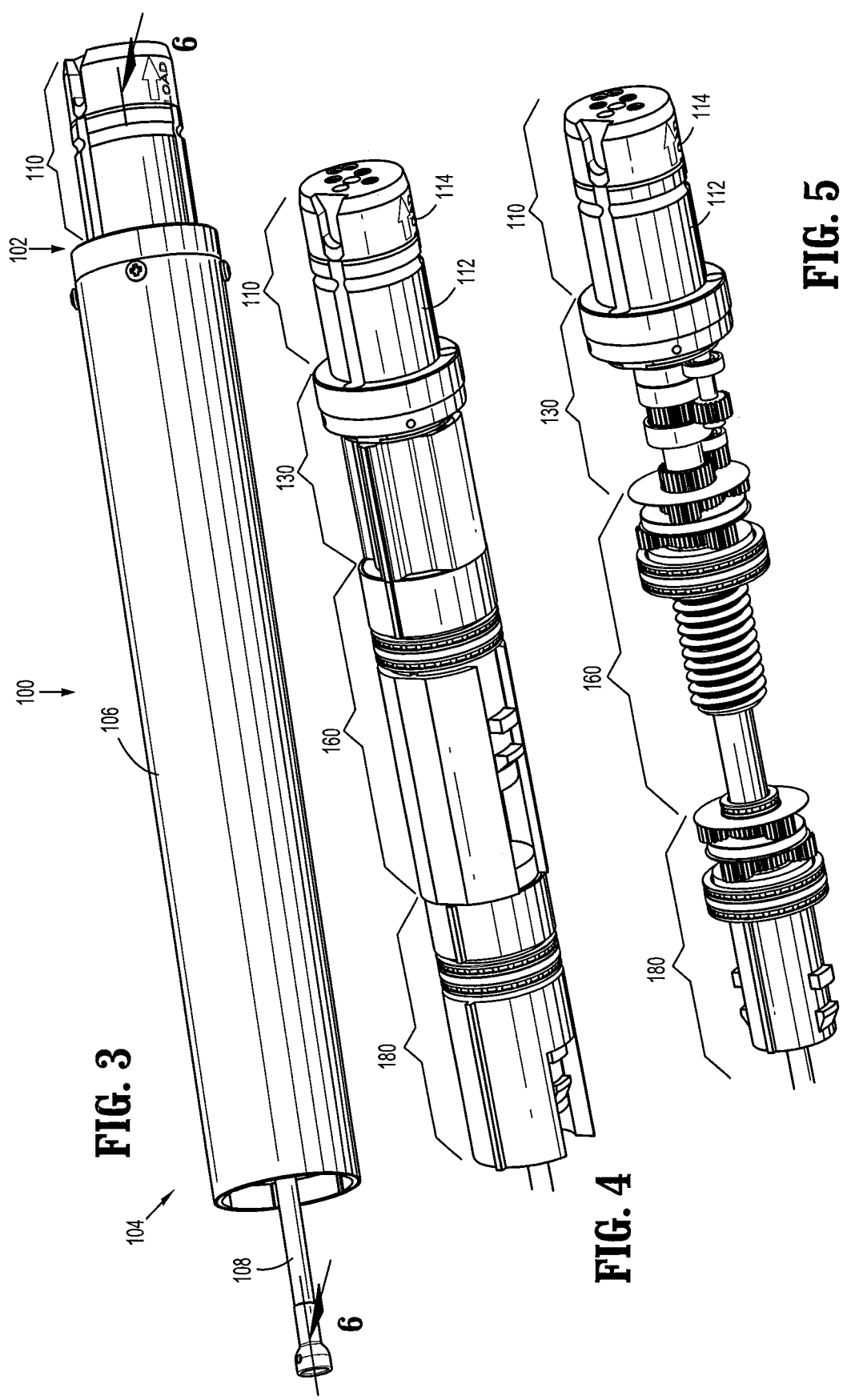

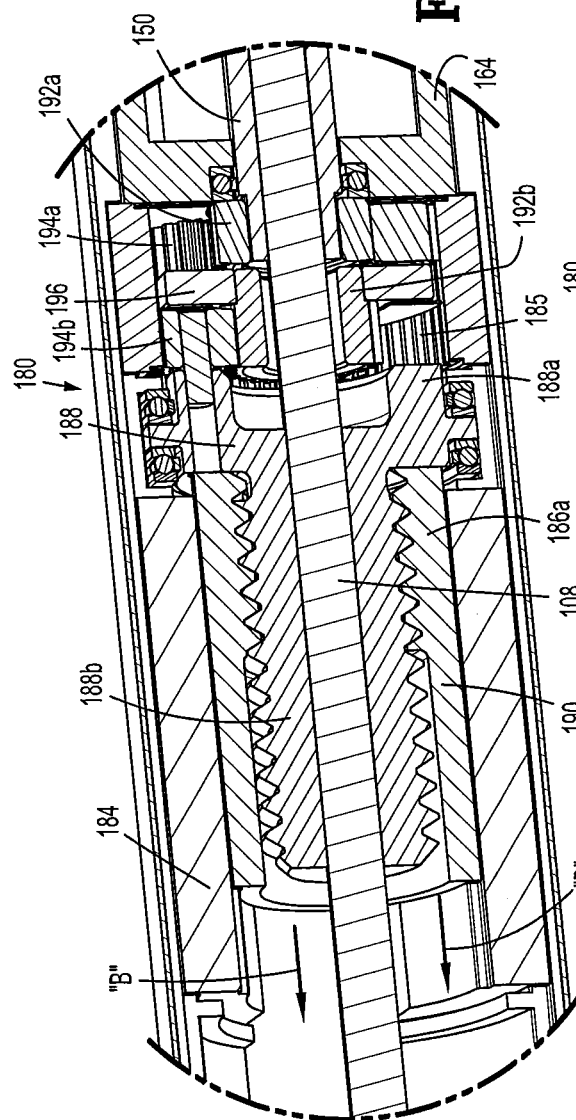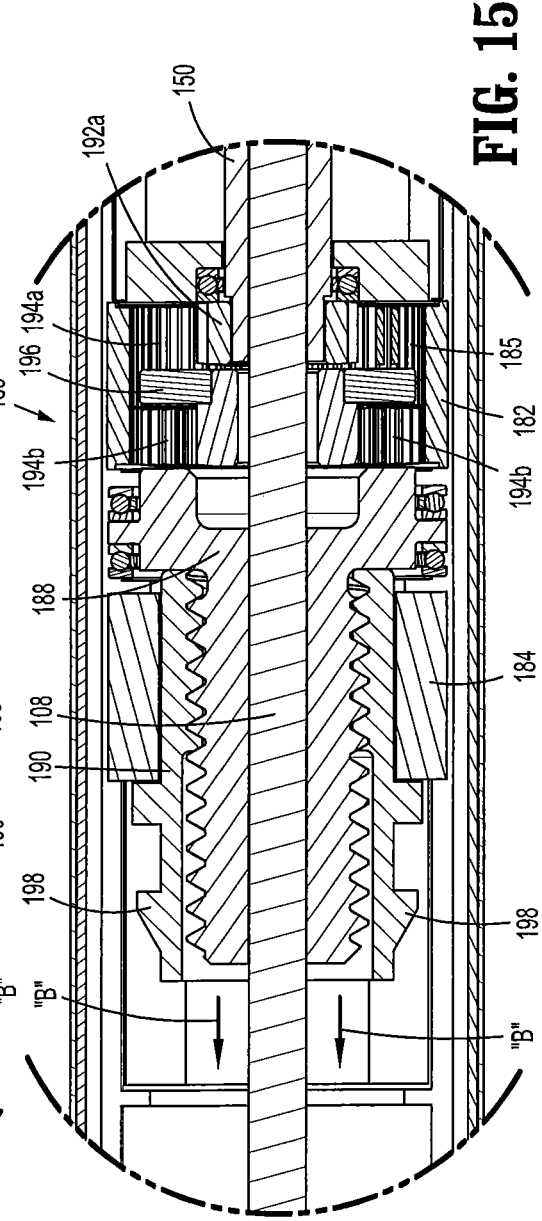

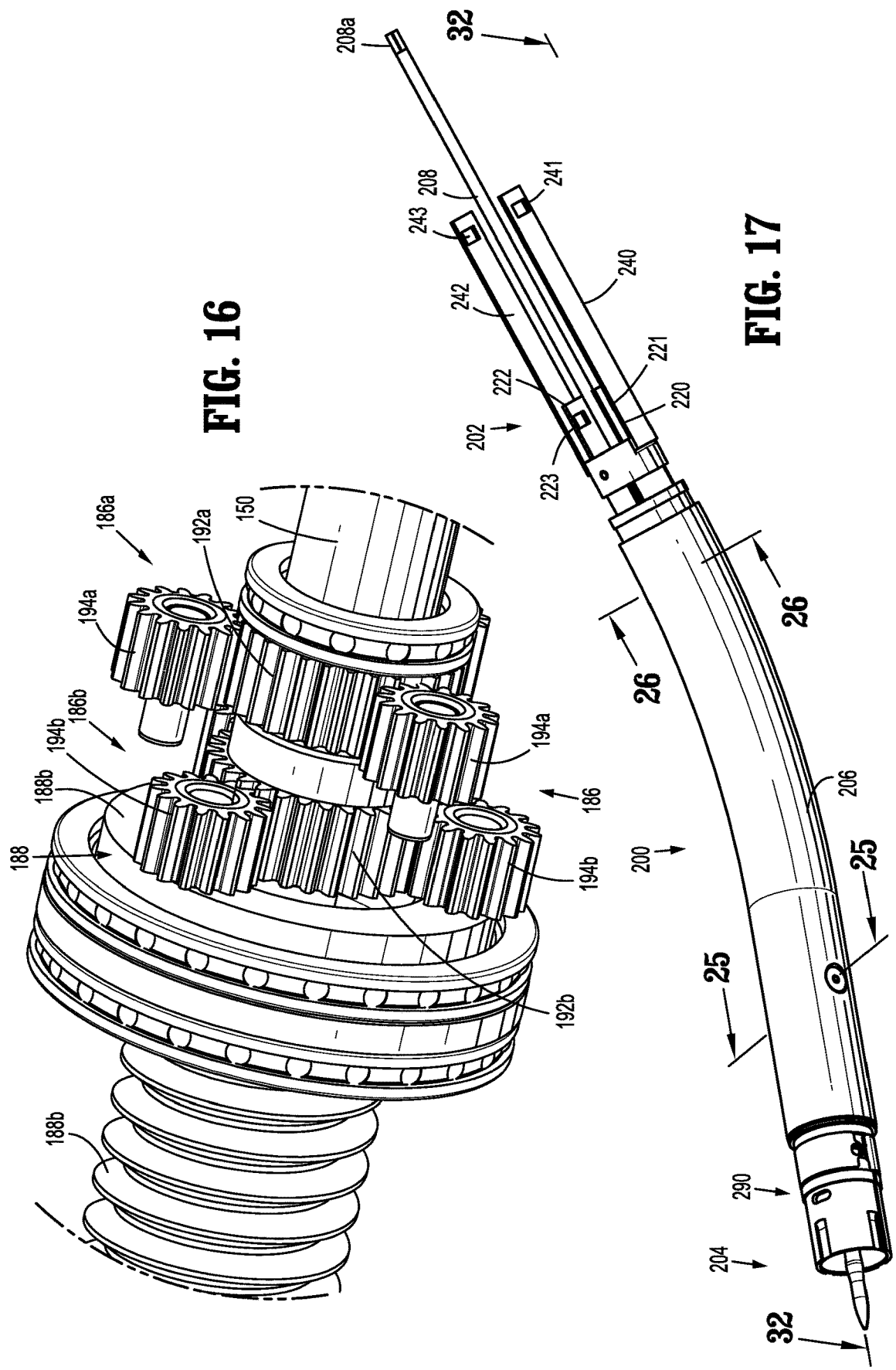

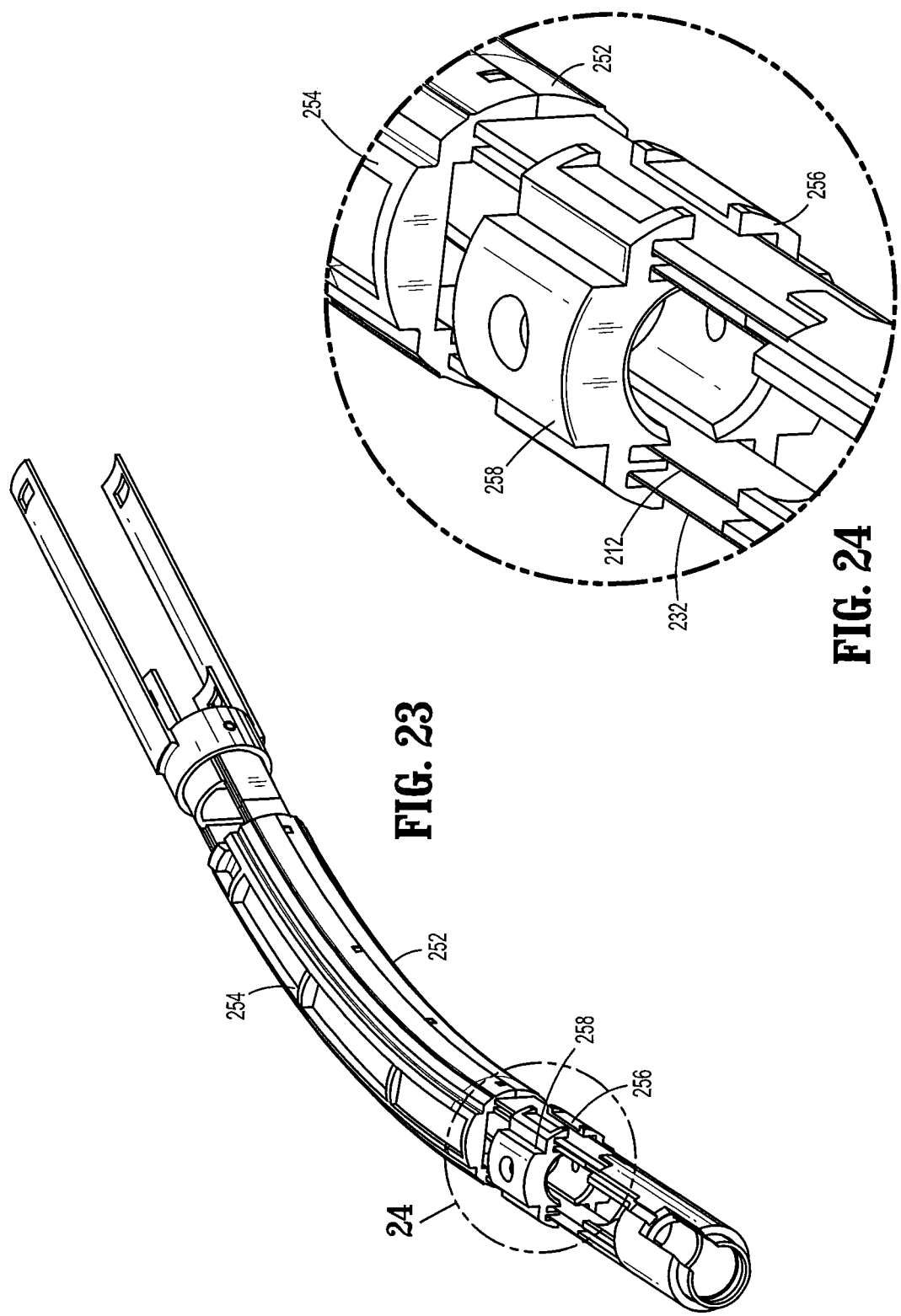

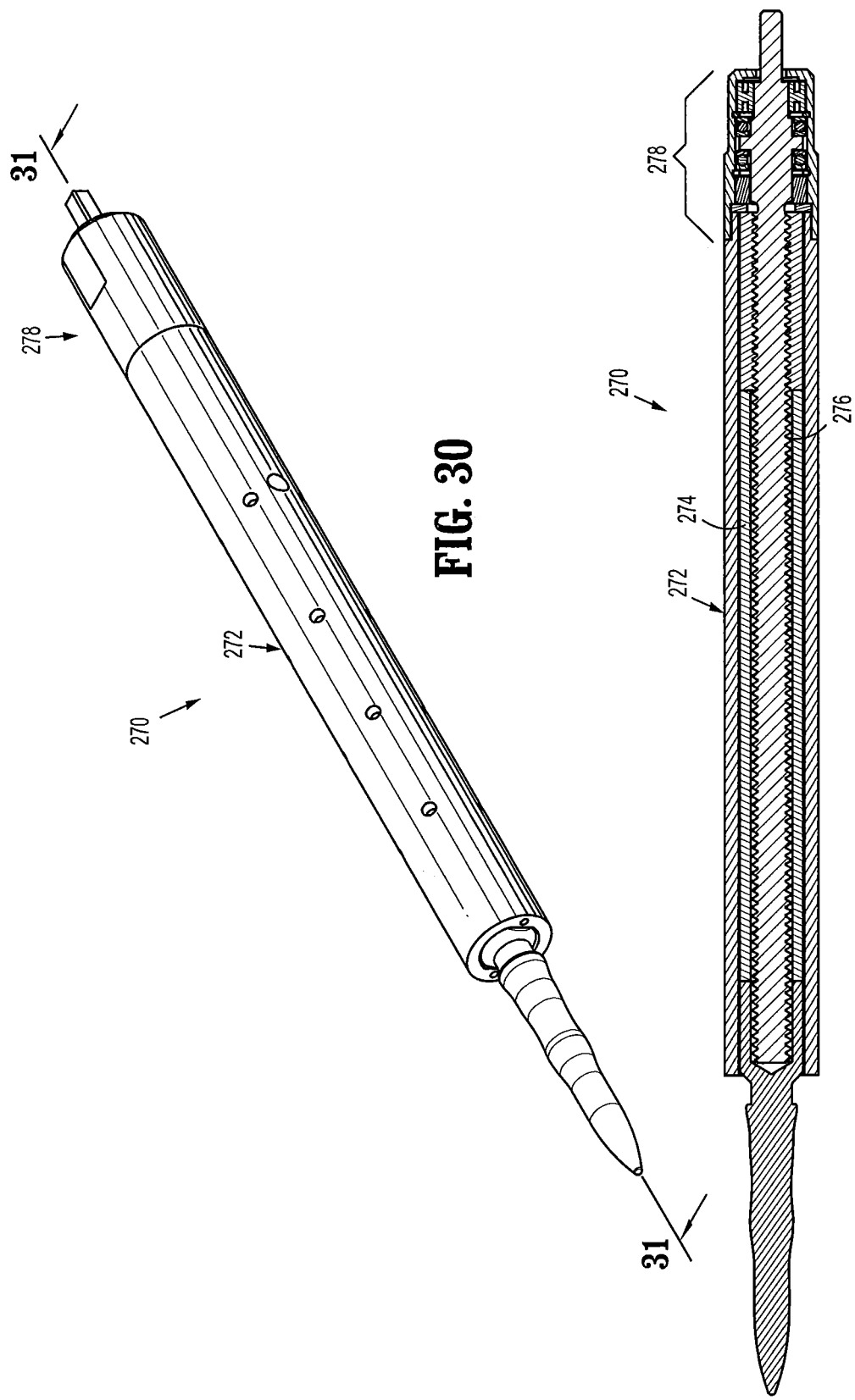

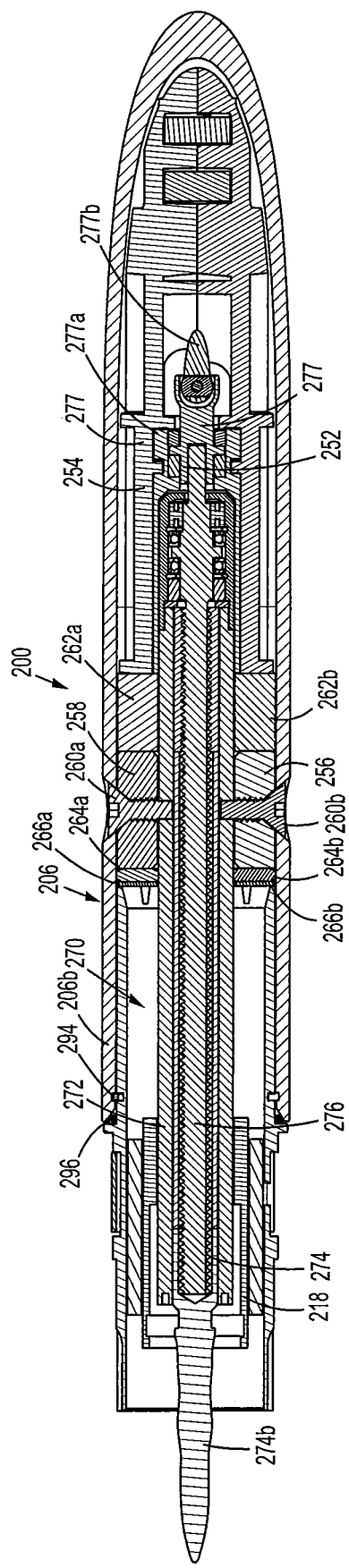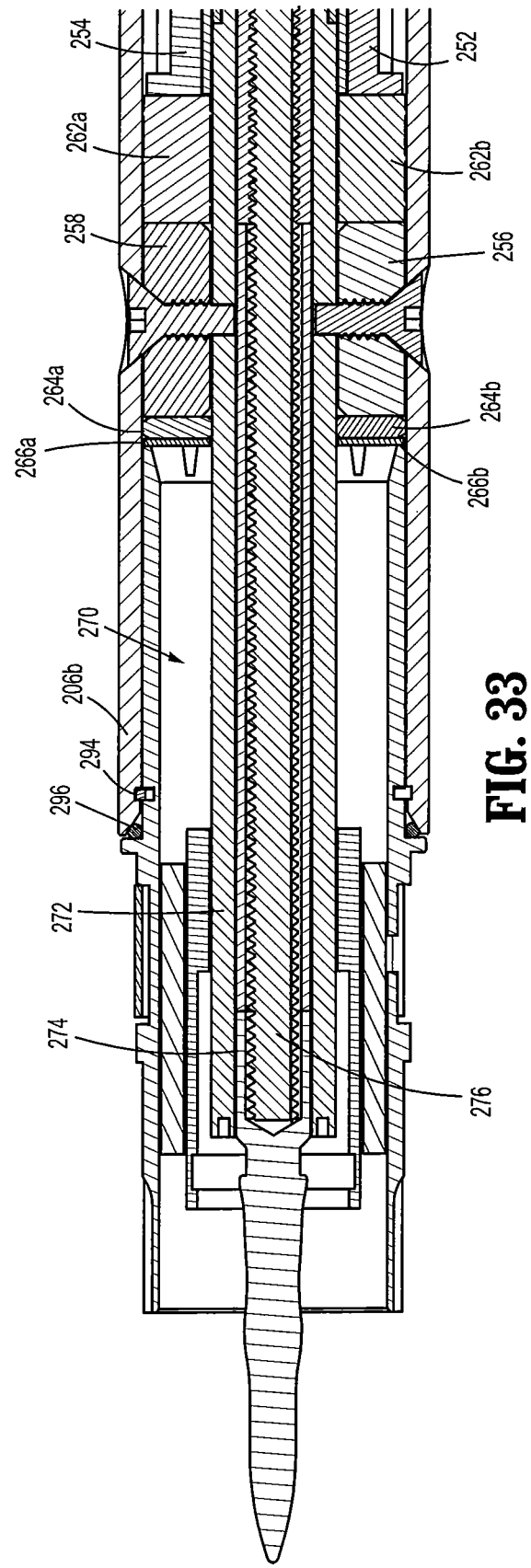

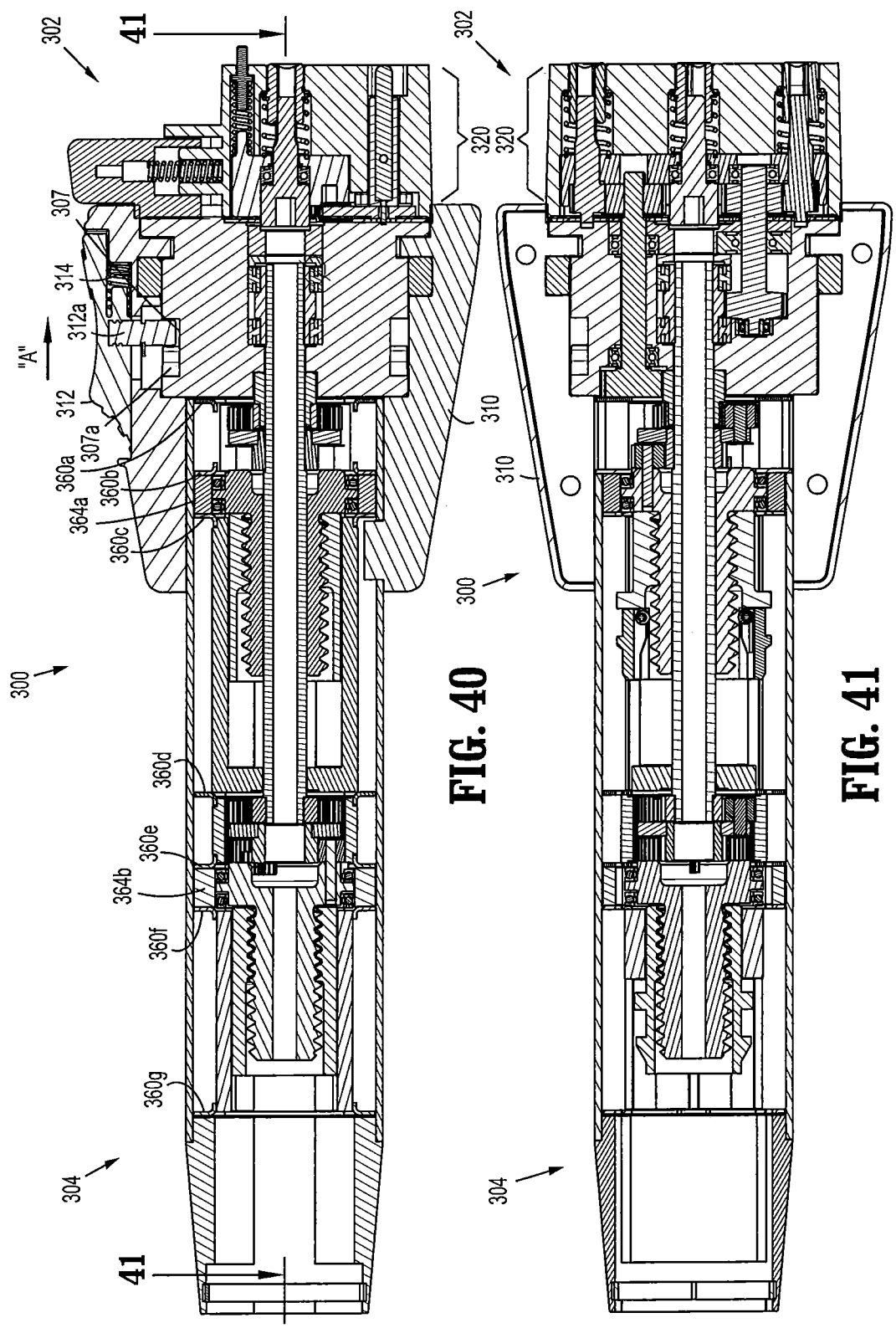

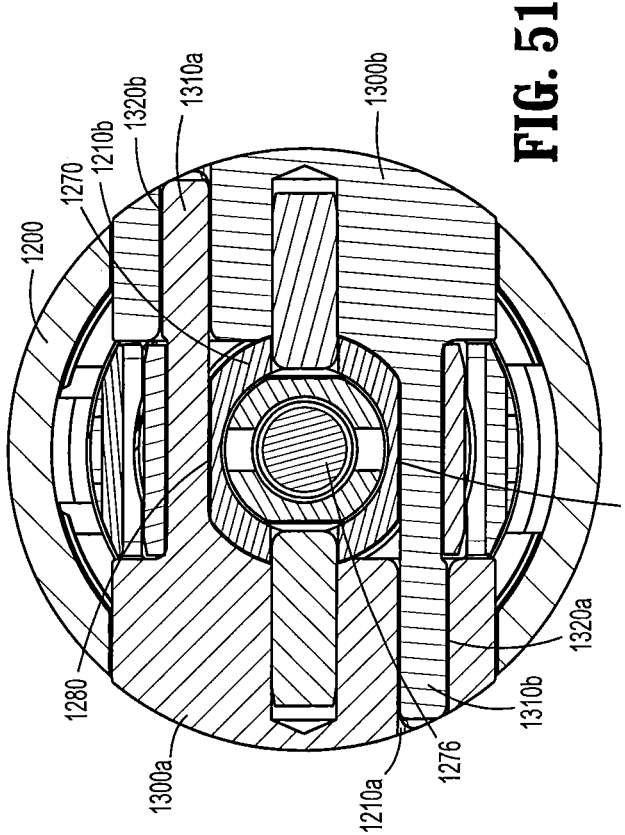
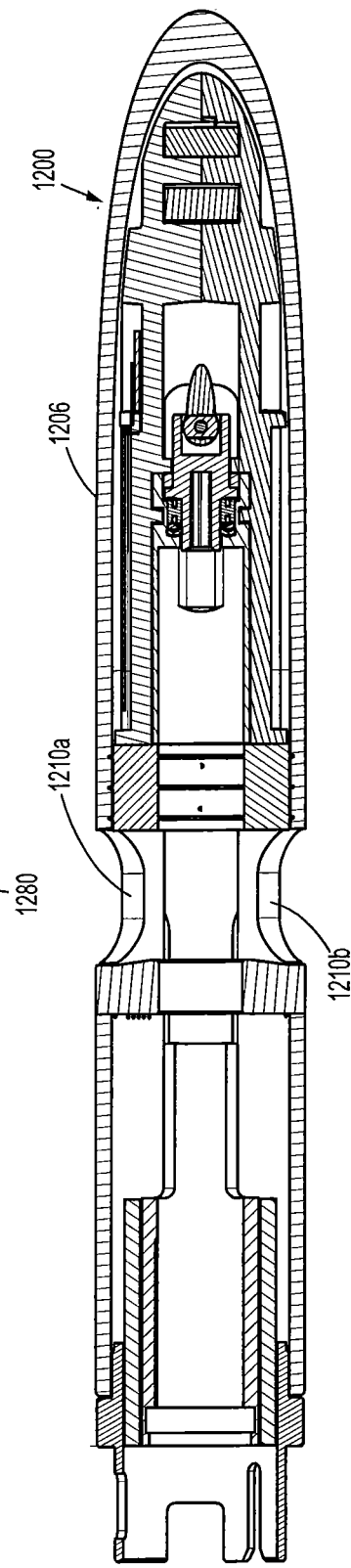

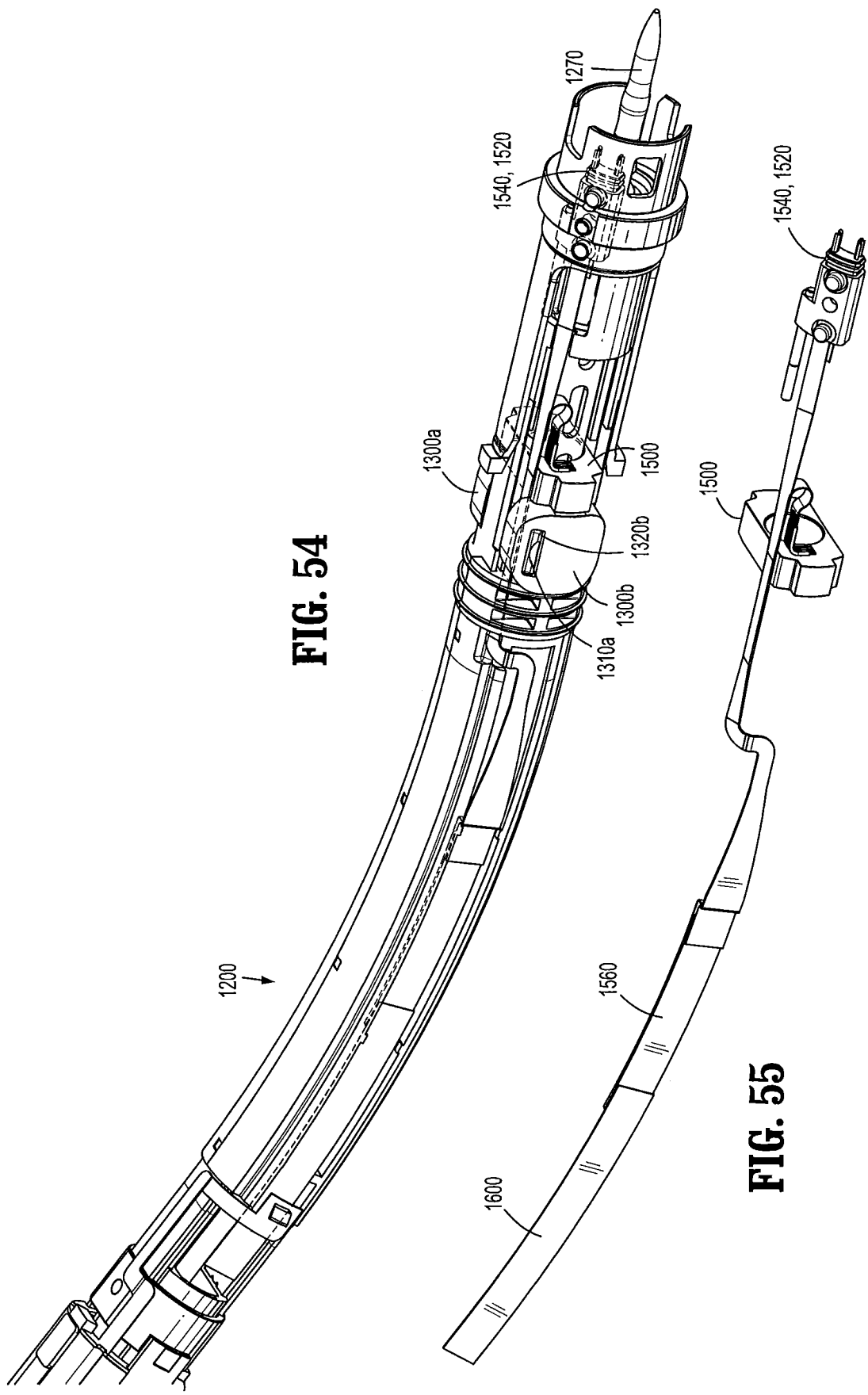

ADAPTER, EXTENSION, AND CONNECTOR ASSEMBLIES FOR SURGICAL DEVICES

CROSS-REFERENCE TO RELATED APPLICATIONS

This application is a continuation application of U.S. patent application Ser. No. 16/448,139, filed on Jun. 21, 2019, now U.S. Pat. No. 11,083,462, which is a divisional application of U.S. patent application Ser. No. 14/991,157, filed on Jan. 8, 2016, now U.S. Pat. No. 10,327,779, which claims the benefit of and priority to U.S. Provisional Patent Application No. 62/145,759, filed on Apr. 10, 2015, the entire contents of which are incorporated by reference herein.

BACKGROUND

The present disclosure relates generally to powered surgical devices. More specifically, the present disclosure relates to adapter and extension assemblies for selectively connecting end effectors to the actuation units of the powered surgical devices.

Powered devices for use in surgical procedures are known. To permit reuse of the handle assemblies of these powered surgical devices and so that the handle assembly may be used with a variety of end effectors, adapter assemblies and extension assemblies have been developed for selective attachment to the handle assemblies and to a variety of end effectors. Following use or following a useful life, the adapter and/or extension assemblies may be disposed of along with the end effector. In some instances, the adapter assemblies and extension assemblies may be sterilized for reuse.

SUMMARY

The present disclosure relates to an adapter assembly for connecting an end effector to an electrosurgical instrument. The adapter assembly includes a drive transfer assembly, first and second pusher assemblies, a drive member, an extension assembly, and a trocar assembly. The drive transfer assembly includes first, second and third rotatable shafts. Each pusher assembly is operably connected to a rotatable shaft for converting rotational motion from one rotatable shaft to longitudinal movement to perform a different function. The drive member is operably connected to the third rotatable shaft for transferring rotational motion from the third rotatable shaft to perform a third function. The extension assembly is operably connected to a distal end of the adapter assembly and includes at least one flexible band assembly operably connected to one of the first and second pusher assemblies. The trocar assembly is configured for releasable engagement with the extension assembly.

In disclosed embodiments, the adapter assembly further comprises at least one retention member, for example a first retention member and a second retention member, configured to releasably couple the trocar assembly with the extension assembly. It is disclosed that each retention member is configured to engage a flat portion of the trocar assembly, the first retention member is configured to engage the second retention member, and that the second retention member is configured to engage the first retention member.

It is also disclosed that the retention member includes a nub configured to releasably engage a respective detent of the trocar assembly.

Additionally, it is disclosed that the extension assembly defines a longitudinal axis, and that the retention member is movable in a direction perpendicular to the longitudinal axis through an opening of the extension assembly and into engagement with the trocar assembly.

The present disclosure also relates to an electromechanical circular stapling instrument including a handle assembly, an elongated portion extending distally from the handle assembly and defining a longitudinal axis, a trocar assembly including a distal tip for penetrating tissue, and first and second retention members configured to releasably couple the trocar assembly with the elongated portion. The trocar assembly is configured for releasable engagement with the elongated portion. The retention members are configured to engage a flat portion of the trocar assembly. The first retention member is configured to engage the second retention member, and the second retention member is configured to engage the first retention member. It is further disclosed that each of the first retention member and the second retention member is configured to engage a flat portion of the trocar assembly.

In disclosed embodiments, the retention members include a nub configured to releasably engage a respective detent of the trocar assembly.

It is also disclosed that the retention members are movable in a direction perpendicular to the longitudinal axis through an opening of the elongated portion and into engagement with the trocar assembly.

The present disclosure also relates to a method of securing a trocar assembly to an elongated portion of a surgical instrument. The method includes inserting a portion of a first retention member through a first opening in an outer wall of the elongated portion of the surgical instrument, inserting a portion of a second retention member through a second opening in the outer wall of the elongated portion of the surgical instrument, engaging the portion of the first retention member with a first flat portion of the trocar assembly, engaging the portion of the second retention member with a second flat portion of the trocar assembly, and engaging the first retention member with the second retention member.

In disclosed embodiments, the method also includes engaging a nub of the first retention member with a first detent of the trocar assembly and engaging a nub of the second retention member with a second detent of the trocar assembly.

It is further disclosed that engaging the first retention member with the second retention member includes inserting an extension portion of the first retention member at least partially within a receptacle of the second retention member, and that the method also includes inserting an extension portion of the second retention member at least partially within a receptacle of the first retention member. It is also disclosed that inserting the extension portion of the first retention member at least partially within the receptacle of the second retention member and inserting the extension portion of the second retention member at least partially within the receptacle of the first retention member occur simultaneously.

In disclosed embodiments, inserting the portion of the first retention member through the first opening in the outer wall of the elongated portion of the surgical instrument includes moving the first retention member in a direction perpendicular to a longitudinal axis defined by the elongated portion.

BRIEF DESCRIPTION OF THE DRAWINGS

Embodiments of the present disclosure are described herein with reference to the accompanying drawings, wherein:

FIG. 3 is a perspective side view of the adapter assembly of FIG. 1;

FIG. 4 is a perspective side view of the adapter assembly of FIG. 3 with the outer sleeve removed;

FIG. 5 is a perspective side view of the adapter assembly of FIGS. 3 and 4 with proximal and distal housings of first and second pusher assemblies removed;

FIG. 14 is an enlarged view of the indicated area of detail of FIG. 6;

FIG. 15 is an enlarged view of the indicated area of detail of FIG. 7;

FIG. 16 is an enlarged view of the indicated area of detail of FIG. 9;

FIG. 17 is a perspective side view of the extension assembly of FIG. 1;

FIG. 23 is a front, perspective view of the inner and outer flexible band assemblies and the frame assembly of FIG. 20;

FIG. 24 is an enlarged view of the indicated area of detail of FIG. 23;

FIG. 30 is a perspective side view of the trocar assembly of FIG. 29;

FIG. 31 is a cross-sectional side view taken along line 31-31 of FIG. 30;

FIG. 32 is a cross-sectional top view taken along line 32-32 of FIG. 17;

FIG. 33 is an enlarge cross-sectional view of the distal end of the extension assembly of FIG. 17;

FIG. 40 is a cross-sectional side view taken along line 40-40 of FIG. 36;

FIG. 41 is a cross-sectional side view taken along line 41-41 of FIG. 40;

FIG. 51 is a transverse cross-sectional view of a portion of the distal end of the adapter assembly of FIG. 50;

FIG. 52 is a longitudinal cross-sectional view of the distal end of the adapter assembly taken along line 52-52 of FIG. 50;

FIGS. 53 and 54 are perspective views of a distal portion of the adapter assembly of FIG. 50, with some parts removed; and FIG. 55 is a perspective view of a sensor assembly of the adapter assembly of FIG. 50.

DETAILED DESCRIPTION

Figure 1:
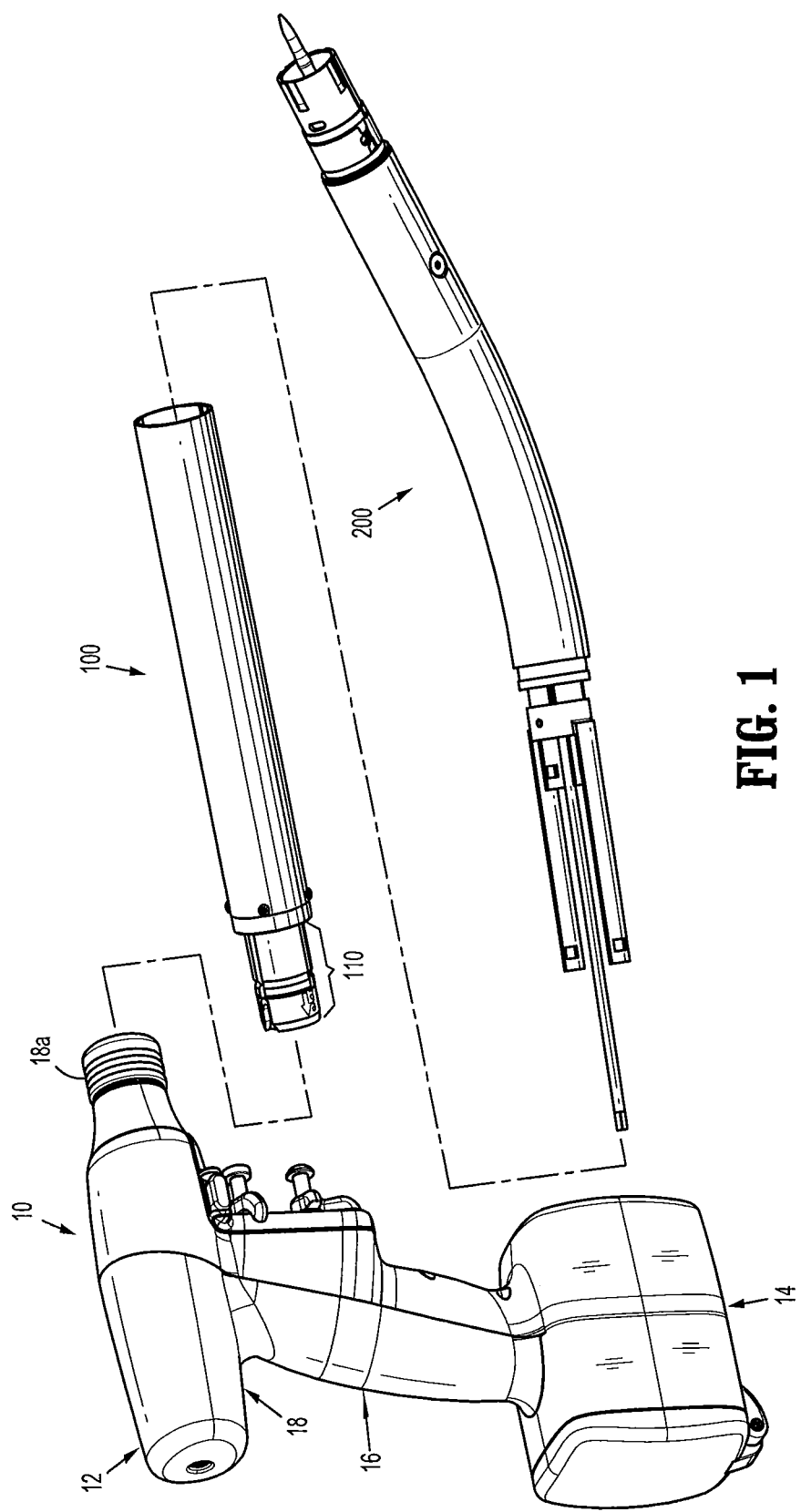
FIG. 1 is a perspective separated view of an adapter assembly, in accordance with an embodiment of the present disclosure, an extension assembly, in accordance with an embodiment of the present disclosure, and an exemplary handheld electromechanical surgical device.

Embodiments of the presently disclosed adapter assemblies and extension assemblies for surgical devices and/or handle assemblies are described in detail with reference to the drawings, in which like reference numerals designate identical or corresponding elements in each of the several views. As used herein the term "distal" refers to that portion of the adapter assembly or surgical device, or component thereof, farther from the user, while the term "proximal" refers to that portion of the adapter assembly or surgical device, or component thereof, closer to the user.

With reference to FIG. 1, an adapter assembly in accordance with an embodiment of the present disclosure, shown generally as adapter assembly 100, and an extension assembly according to an embodiment of the present disclosure, shown generally as extension assembly 200, are configured for selective connection to a powered handheld electromechanical instrument shown, generally as surgical device 10. As illustrated in FIG. 1, surgical device 10 is configured for selective connection with adapter assembly 100, and, in turn, adapter assembly 100 is configured for selective connection with an extension assembly 200. Extension assembly 200 is configured for selective connection with a tool assembly or end effector, e.g. tool assembly 30 (FIG. 34), including a loading unit, e.g. loading unit 40 (FIG. 34), and an anvil assembly, e.g., anvil assembly 50 (FIG. 34), for applying a circular array of staples (not shown) to tissue (not shown).

Figure 2:
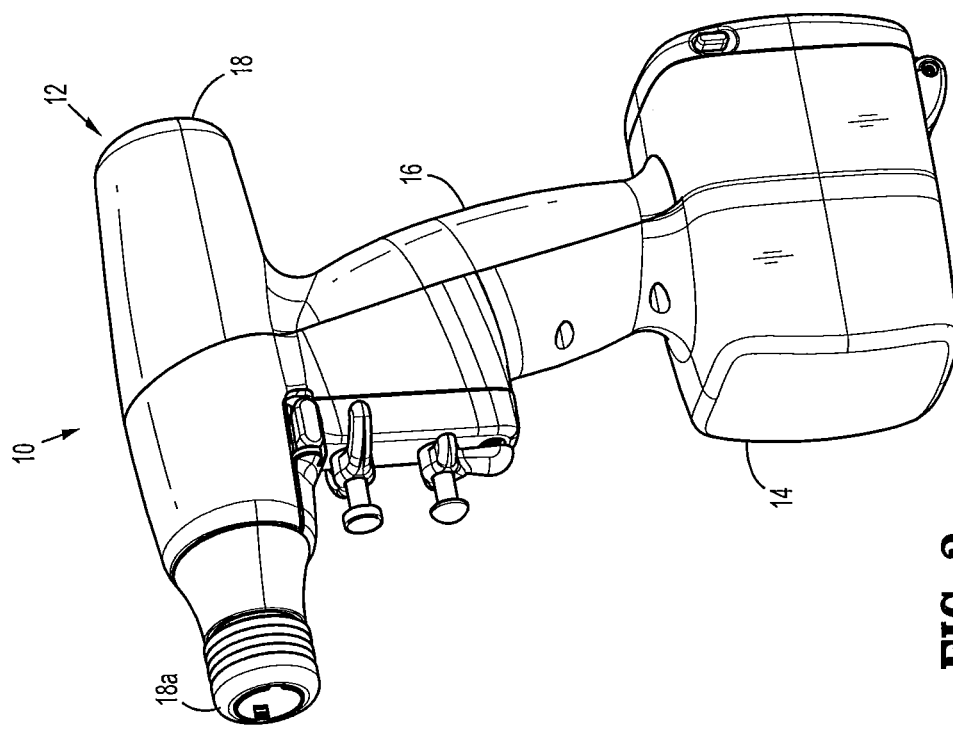
FIG. 2 is a perspective side view of the exemplary handheld electromechanical surgical device of FIG. 1.
Figure 6:
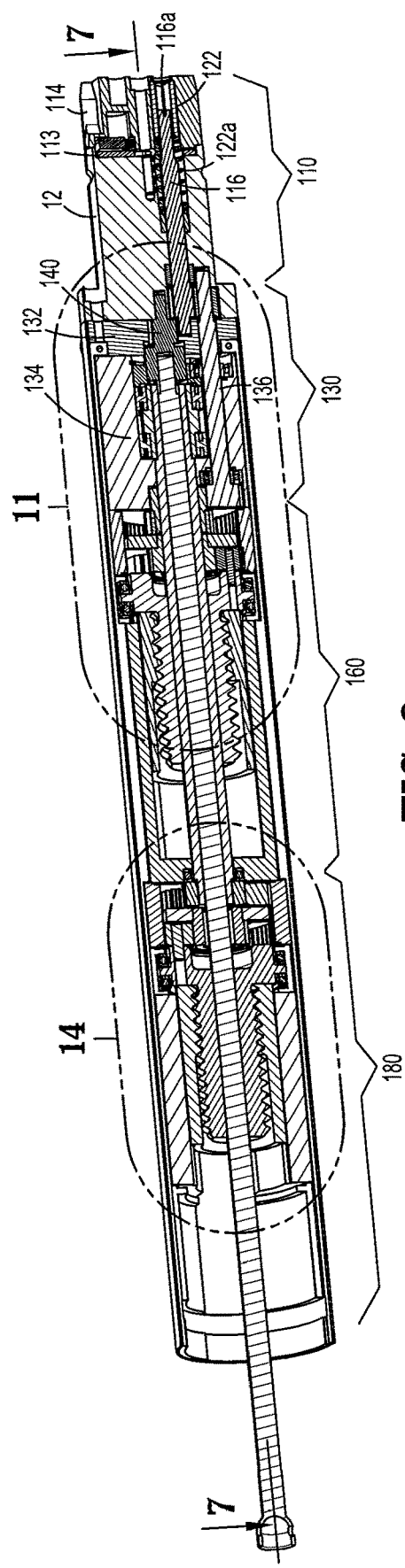
FIG. 6 is a cross-sectional side view of the adapter assembly of FIGS. 3-5 taken along line 6-6 in FIG. 3.
Figure 7:
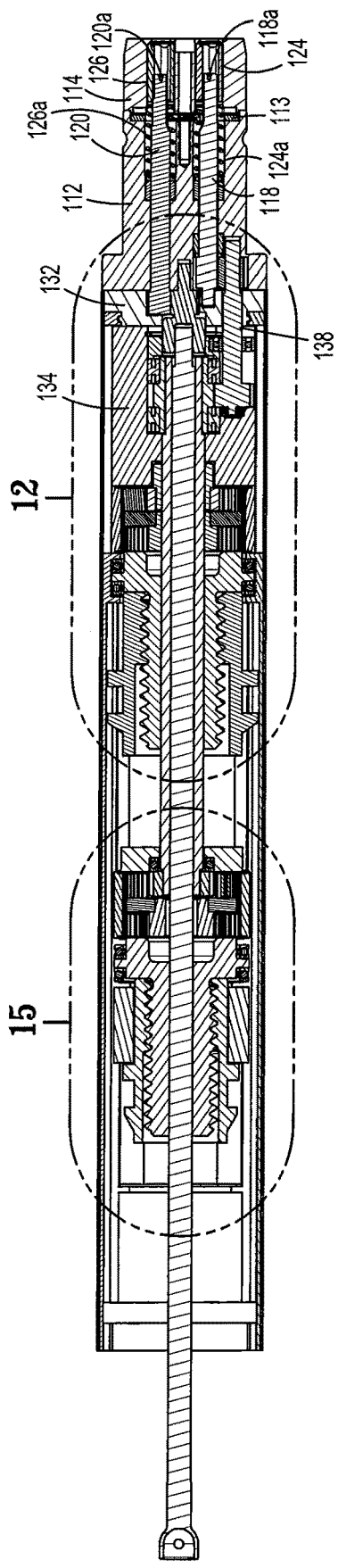
FIG. 7 is a cross-sectional side view of the adapter assembly of FIGS. 3-5 taken along line 7-7 in FIG. 6.
Figure 8:
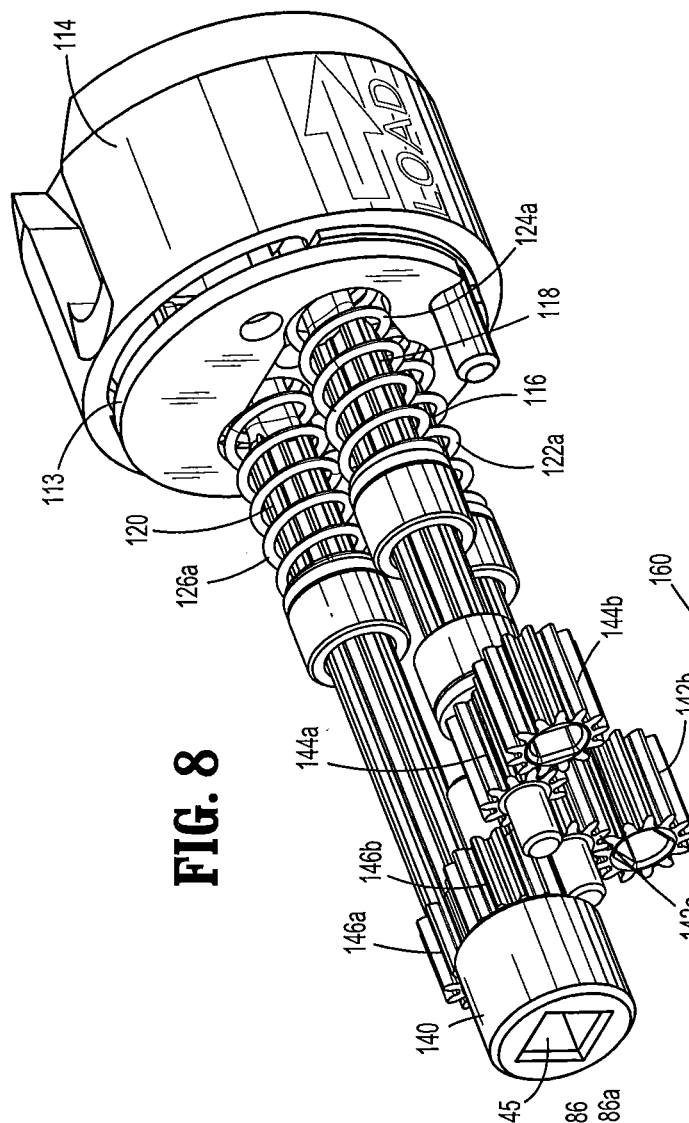
FIG. 8 is an enlarged, perspective view of a coupling assembly and a transfer assembly of the adapter assembly of FIGS. 3-7.
Figure 9:
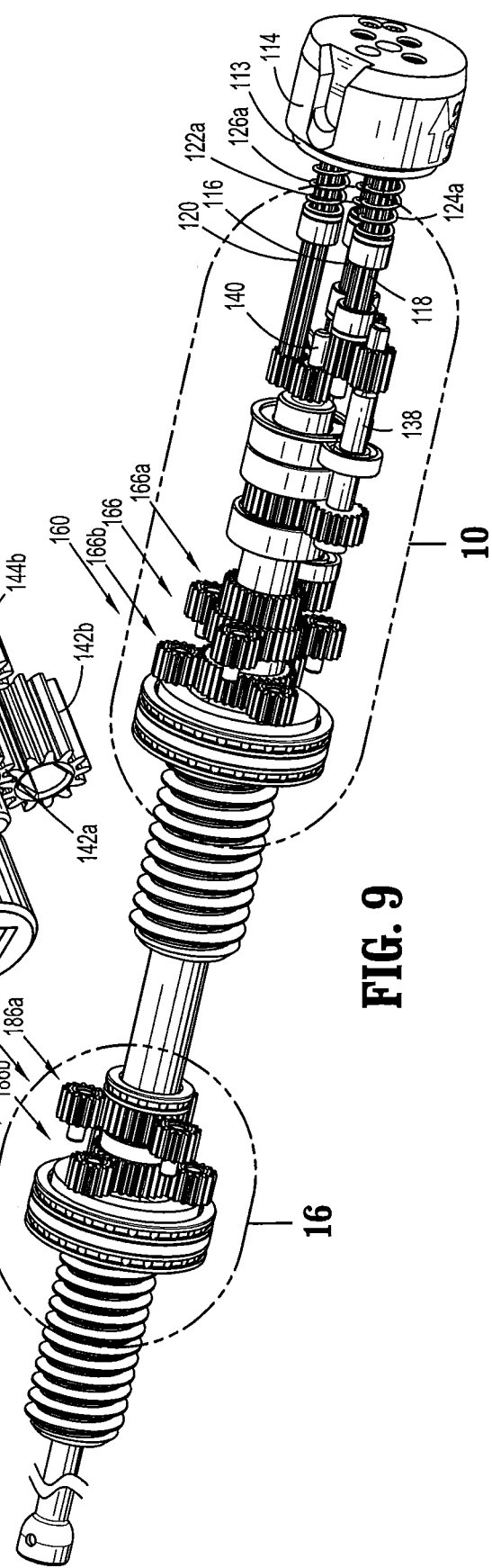
FIG. 9 is a perspective side view of the adapter assembly of FIGS. 3-7 with the housing assemblies removed.

As illustrated in FIGS. 1 and 2, surgical device 10 includes a handle housing 12 having a lower housing portion 14, an intermediate housing portion 16 extending from and/or supported on lower housing portion 14, and an upper housing portion 18 extending from and/or supported on intermediate housing portion 16. A distal half-section of upper housing portion 18 defines a nose or connecting portion 18a configured to accept a corresponding drive coupling assembly 110 (FIG. 10) of adapter assembly 100. For a detailed description of the structure and function of an exemplary electromechanical instrument, please refer to commonly-owned U.S. Pat. Appl. Publ. No. 2012/0253329 ("the '329 application"), now U.S. Pat. No. 9,055,943, the contents of which are incorporated by reference herein in their entirety.

Adapter assembly 100 will now be described with reference to FIGS. 3-20. Referring initially to FIG. 3, adapter assembly 100 includes a proximal end 102 configured for operable connection to connecting portion 18a (FIG. 1) of surgical device 10 (FIG. 1) and a distal end 104 configured for operable connection to extension assembly 200 (FIG. 1). In accordance with the present disclosure, adapter assembly 100 may be substantially or fully rigid along the entire length.

Turning to FIGS. 3-5, from proximal end 102 to distal end 104 of adapter assembly 100, adapter assembly 100 includes a drive coupling assembly 110, a drive transfer assembly 130 operably connected to drive coupling assembly 110, a first pusher assembly 160 operably connected to drive transfer assembly 130, and a second pusher assembly 180 operably connected to drive transfer assembly 130. Each of drive transfer assembly 130, first pusher assembly 160 and second pusher assembly 180 are operably maintained within an outer sleeve 106 (FIG. 3). As will be described in further detail below, a shaft 108 (FIG. 3) extends longitudinally through adapter assembly 100 and is operably connected to drive transfer assembly 130.

With reference to FIGS. 5-9, drive coupling assembly 110 has a cylindrical profile and is configured to selectively secure adapter assembly 100 to surgical device 10 (FIG. 1). Drive coupling assembly 110 includes a connector housing 112 and a connector extension 114 fixedly connected to connector housing 112 by a mounting plate 113. Connector housing 112 and connector extension 114 operate to rotatably support a first rotatable proximal drive shaft 116, a second rotatable proximal drive shaft 118, and a third rotatable proximal drive shaft 120. Connector housing 112 and connector extension 114 of drive coupling assembly 110 also rotatably supports first, second, and third connector sleeves 122, 124, and 126, respectively. Each of connector sleeves 122, 124, 126 is configured to mate with respective first, second, and third drive connectors (not shown) of surgical device 10 (FIG. 1). Each connector sleeve 122, 124, 126 is further configured to mate with a proximal end 116a, 118a, 120a of respective first, second and third proximal drive shafts 116, 118, 120.

Drive coupling assembly 110 also includes first, second and third biasing members 122a, 124a and 126a disposed distally of respective first, second and third connector sleeves 122, 124, 126. Each of biasing members 122a, 124a and 126a is disposed about respective first, second, and third rotatable proximal drive shafts 116, 118 and 120 to help maintain connector sleeves 122, 124, and 126 engaged with the distal end of respective drive rotatable drive connectors (not shown) of surgical device 10 when adapter assembly 100 is connect to surgical device 10. In particular, first, second and third biasing members 122a, 124a and 126a function to bias respective connector sleeves 122, 124 and 126 in a proximal direction.

For a detailed description of an exemplary drive coupling assembly, please refer to the '329 application, the contents of which was previously incorporated by reference herein.

With reference to FIGS. 9-13, drive transfer assembly 130 (FIGS. 10 and 13) of adapter assembly 100 has a cylindrical profile and operably connects distal ends of first, second and third rotatable proximal drive shafts 116, 118 and 120 to shaft 108, first pusher assembly 160, and second pusher assembly 180, respectively. Drive transfer assembly 130 includes a support plate 132 (FIGS. 11 and 12) secured to a proximal end of connector housing 112 and a drive transfer housing 134 positioned adjacent support plate 132. Support plate 132 and housing 134 operate to rotatably support a first rotatable distal drive shaft 136, a second rotatable distal drive shaft 138 and a drive member 140.

First and second rotatable distal drive shafts 136 and 138 are each operably connected to respective first and second rotatable proximal drive shafts 116 and 118 of drive coupling assembly 110 by a pair of gears. In particular, distal ends of each of first and second rotatable proximal drive shaft 116 and 118 include a geared portion 142a and 144a, respectively, which engages a proximal drive gear 142b and 144b on a proximal end of respective first and second distal drive shafts 136 and 138. As shown, each of respective paired geared portion and proximal drive gear 142a, 142b and 144a, 144b are the same size to provide a 1:1 gear ratio between the respective rotatable proximal and distal drive shafts. In this manner, respective rotatable proximal and distal drive shafts rotate at the same speed. However, it is envisioned that either or both of the paired geared portions and proximal drive gears may be of different sizes to alter the gear ratio between the rotatable proximal and distal drive shafts.

A distal end of third proximal drive shaft 120 of drive coupling assembly 110 includes a geared portion 146a that engages a geared portion 146b formed on a proximal end of drive member 140 of drive transfer assembly 130. The size of geared portion 146a on third proximal drive shaft 120 and geared portion 146b on drive member 140 are the same size to provide a 1:1 gear ratio between third proximal drive shaft 120 and drive member 140. In this manner, third proximal drive shaft 120 and drive member 140 rotate at the same speed. However, it is envisioned that either or both of geared portions 146a, 146b may be of different sizes to alter the gear ratio between third proximal drive shaft 120 and drive member 140. A distal end of drive member 140 defines a socket 145 that receives a proximal end 108a of shaft 108. Alternatively, socket 145 may be configured to operably engage a proximal end 208a of a drive shaft (FIG. 17) of an extension assembly 200 (FIG. 17).

Drive transfer assembly 130 also includes a drive connector 148 (FIG. 11) operably connecting first rotatable distal drive shaft 136 to first pusher assembly 160 and a tubular connector 150 operably connecting second rotatable distal drive shaft 138 to second pusher assembly 180. In particular, a distal end of first rotatable distal drive shaft 136 includes a geared portion 152a that engages a geared portion 152b of drive connector 148. A distal end of second rotatable distal drive shaft 138 includes a geared portion 154a that engages a drive gear 154b secured to a proximal end of tubular connector 150.

Figure 10:
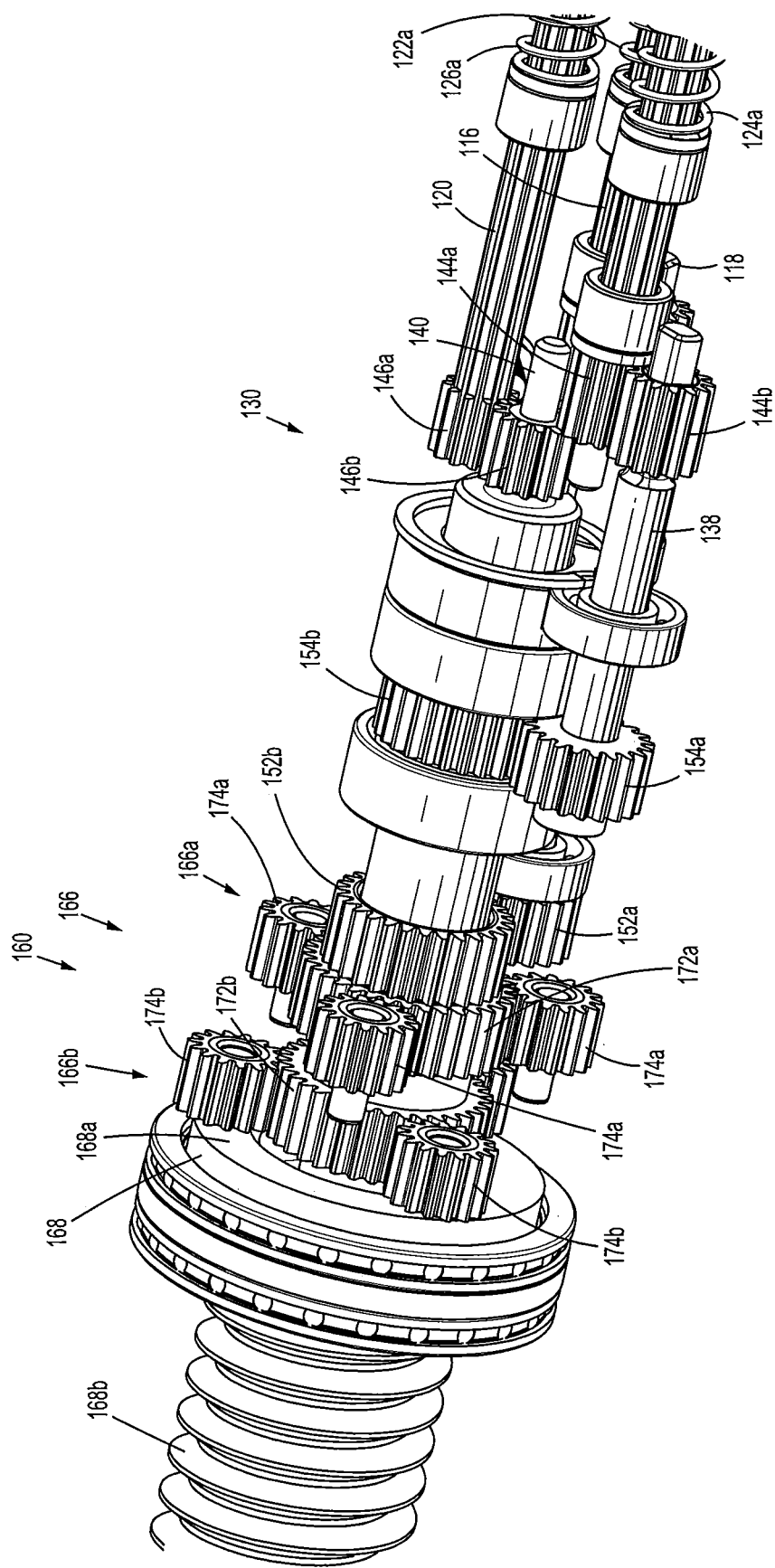
FIG. 10 is an enlarged view of the indicated area of detail of FIG. 9.
Figure 11:
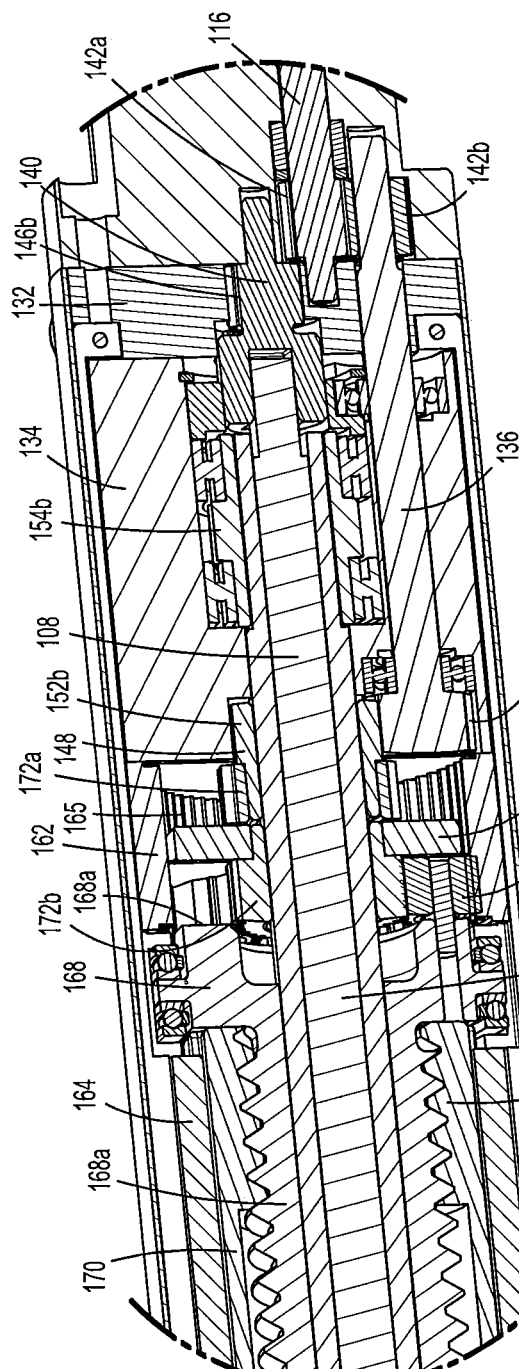
FIG. 11 is an enlarged view of the indicated area of detail of FIG. 6.

As shown in FIG. 10, geared portion 152a of first rotatable distal drive shaft 136 is smaller than geared portion 152b of drive connector 148 to provide a gear ratio of greater than 1:1 between first rotatable distal drive shaft 136 and drive connector 148. In this manner, drive connector 148 rotates at a slower speed than first rotatable distal drive shaft 136. Similarly, geared portion 154a of second rotatable distal drive shaft 138 is smaller than drive gear 154b on tubular connector 150 to provide a gear ratio of greater than 1:1 between second rotatable distal drive shaft 138 and drive connector 148. In this manner, tubular connector 150 rotates at a slower speed than second rotatable distal drive shaft 138. However, it is envisioned that each of paired geared portion 152a and geared portion 152b, and geared portion 154a and drive gear 154b may be the same size to provide a gear ratio of 1:1 between respective first rotatable distal drive shaft 136 and drive connector 148 and between second rotatable distal drive shaft 138 and tubular connector 150.

With particular reference to FIGS. 9-13, first pusher assembly 160 includes proximal and distal housing sections 162, 164 (FIG. 11), a planetary gear assembly 166 operably mounted within proximal housing section 162, a screw member 168 (FIG. 11) operably connected to planetary gear assembly 166 and rotatably supported within distal housing section 164, and a pusher member 170 (FIG. 11) operably connected to screw member 168 and slidably disposed within distal housing section 164. Planetary gear assembly 166 includes first and second planetary gear systems 166a, 166b (FIG. 10). First planetary gear system 166a includes a central drive gear 172a mounted on a distal end of drive connector 148 of drive transfer assembly 130 and a plurality of planetary gears 174a rotatably mounted to a rotatable support ring 176.

Each planetary gear 174a of first planetary gear system 166a engages central drive gear 172a and a toothed inner surface 165 of proximal housing section 162. As central drive gear 172a rotates in a first direction, i.e., clockwise, each planetary gear 174a rotates in a second direction, i.e., counter-clockwise. As each planetary gear 174a rotates in the second direction, engagement of planetary gears 174a with toothed inner surface 165 of proximal housing section 162 causes rotatable support ring 176 to rotate in the first direction. Conversely, rotation of central drive gear 172a in the second direction causes rotation of each planetary gear 174a in the first direction thereby causing rotation of rotatable support ring 176 in the second direction. The configuration of first planetary gear system 166a provides a reduction in the gear ratio. In this manner, the speed of rotation of rotatable support ring 176 is less than the speed of rotation of central drive gear 172a.

Second planetary gear system 166b includes a central drive gear 172b securely affixed to rotatable support ring 176 and a plurality of planetary gears 174b rotatably mounted to a proximal end surface 168a of screw member 168. Each planetary gear 174b of second planetary gear system 166b engages central drive gear 172b and toothed inner surface 165 of proximal housing section 162. As rotatable support ring 176 of first planetary gear system 166a rotates in the first direction thereby causing central drive gear 172b to also rotate in the first direction, each planetary gear 174b rotates in the second direction. As each planetary gear 174b rotates in the second direction, engagement of planetary gears 174b with toothed inner surface 165 of proximal housing section 162 causes screw member 168 to rotate in the first direction. Conversely, rotation of central drive gear 172b in the second direction causes rotation of each planetary gear 174b in the first direction, thereby causing screw member 168 to rotate in the second direction. The configuration of second planetary gear system 166b provides a reduction in the gear ratio. In this manner, the speed of rotation of screw member 168 is less than the speed of rotation of central drive gear 172b. First and second planetary gear systems 166a, 166b operate in unison to provide a reduction in the gear ratio between first rotatable proximal drive shaft 116 and screw member 168. In this manner, the reduction in the speed of rotation of screw member 168 relative to drive connector 148 is a product of the reduction provided by the first and second planetary gear systems 166a, 166b.

Screw member 168 is rotatably supported within proximal housing portion 162 and includes a threaded distal end 168b that operably engages a threaded inner surface 170a of pusher member 170. As screw member 168 is rotated in the first direction, engagement of threaded distal end 168b of screw member 168 with threaded inner surface 170a of pusher member 170 (which is keyed to permit axial translation and prevent rotation thereof) causes longitudinal advancement of pusher member 170, as indicated by arrows "A" in FIG. 12. Conversely, rotation of screw member 168 in the second direction causes retraction of pusher member 170.

Pusher member 170 of first pusher assembly 160 of adapter assembly 100 includes a pair of tabs 178 formed on a distal end thereof for engaging connector extensions 240, 242 (FIG. 19) of outer flexible band assembly 230 (FIG. 19) of extension assembly 200 (FIG. 17). Although shown as tabs 178, it is envisioned that pusher member 170 may include any structure suitable for selectively engaging connector extensions 240, 242 of outer flexible band 230 of extension assembly 200.

With particular reference now to FIGS. 14-16, second pusher assembly 180 is substantially similar to first pusher assembly 160, and includes proximal and distal housing sections 182, 184, a planetary gear assembly 186 operably mounted within proximal housing section 182, a screw member 188 operably connected to planetary gear assembly 186 and rotatably supported within distal housing section 184, and a pusher member 190 operably connected to screw member 188 and slidably disposed within distal housing section 184. Planetary gear assembly 186 includes first and second planetary gear systems 186a, 186b (FIG. 16). First planetary gear system 186a includes a central drive gear 192a mounted on a distal end of tubular connector 150 of drive transfer assembly 130 and a plurality of planetary gears 194a rotatably mounted to a rotatable support ring 196.

Each planetary gear 194a of first planetary gear system 186a engages central drive gear 192a and a toothed inner surface 185 of proximal housing section 182. As central drive gear 192a rotates in a first direction, i.e., clockwise, each planetary gear 194a rotates in a second direction, i.e., counter-clockwise. As each planetary gear 194a rotates in the second direction, engagement of planetary gears 194a with toothed inner surface 185 of distal housing section 182 causes rotatable support ring 196 to rotate in the first direction. Conversely, rotation of central drive gear 192a in the second direction causes rotation of each planetary gear 194a in the first direction thereby causing rotation of rotatable support ring 196 in the second direction. The configuration of first planetary gear system 186a provides a reduction in the gear ratio. In this manner, the speed of rotation of rotatable support ring 196 is less than the speed of rotation of central drive gear 192a.

Second planetary gear system 186b includes a central drive gear 192b securely affixed to rotatable support ring 196 and a plurality of planetary gears 194b rotatably mounted to a proximal end surface 188a of screw member 188. Each planetary gear 194b of second planetary gear system 186b engages central drive gear 192b and toothed inner surface 185 of proximal housing section 182. As rotatable support ring 196 of first planetary gear system 186a rotates in the first direction thereby causing central drive gear 192b to also rotate in the first direction, each planetary gear 194b rotates in the second direction. As each planetary gear 194b rotates in the second direction, engagement of planetary gears 194b with toothed inner surface 185 of proximal housing section 182 causes screw member 188 to rotate in the first direction. Conversely, rotation of central drive gear 192b in the second direction causes rotation of each planetary gear 194b in the first direction, thereby causing screw member 188 to rotate in the second direction. The configuration of second planetary gear system 186b provides a reduction in the gear ratio. In this manner, the speed of rotation of screw member 188 is less than the speed of rotation of central drive gear 192b. First and second planetary gear systems 186a, 186b operate in unison to provide a reduction in the gear ratio between second rotatable proximal drive shaft 118 and screw member 188. In this manner, the reduction in the speed of rotation of screw member 188 relative to tubular connector 150 is a product of the reduction provided by the first and second planetary gear systems 186a, 186b.

Screw member 188 is rotatably supported within proximal housing portion 182 and includes a threaded distal end 188b that operably engages a threaded inner surface 190a of pusher member 190. As screw member 188 is rotated in the first direction, engagement of threaded distal end 188b of screw member 188 with threaded inner surface 190a of pusher member 190 (which is keyed to permit axial translation and prevent rotation thereof) causes longitudinal advancement of pusher member 190. Conversely, rotation of screw member 188 in the second direction causes retraction of pusher member 190.

Pusher member 190 of second pusher assembly 180 of adapter assembly 100 includes a pair of tabs 198 formed on a distal end thereof for engaging connector extensions 220, 222 (FIG. 18) of inner flexible band assembly 210 (FIG. 18) of extension assembly 200 (FIG. 17). Although shown as tabs 198, it is envisioned that pusher member 190 may include any structure suitable for selectively engaging connector extensions 240, 242 of outer flexible band 230 of extension assembly 200.

Turning now to FIGS. 17-34, extension assembly 200 for operably connecting adapter assembly 100 (FIG. 3) with a circular loading unit, e.g. loading unit 40 (FIG. 34) and an anvil assembly, e.g., anvil assembly 50 (FIG. 34) will be described. In particular, a proximal end 202 of extension assembly 200 operably connects with distal end 104 (FIG. 3) of adapter assembly 100 (FIG. 3) and a distal end 204 of extension assembly 200 operably connects with loading unit 40 and anvil assembly 50. As shown, extension assembly 200 provides a slight curvature between proximal and distal end 202, 204. In an alternative embodiment, extension assembly 200 may be straight or may include a greater curvature. In accordance with the present disclosure, extension assembly 200 may be substantially or fully rigid along its entire length.

Although extension assembly 200 will be shown and described as being used to connect loading unit 40 and anvil assembly 50 to adapter assembly 100 (FIG. 3), it is envisioned that the aspects of the present disclosure may be modified for use with various loading units, anvil assemblies, and adapter assemblies. Exemplary loading units and anvil assemblies are described in commonly-owned U.S. Pat. No. 8,590,763, and U.S. patent application Ser. No. 14/056,301 (now U.S. Pat. No. 10,463,365) and Ser. No. 14/149,355 (now U.S. Pat. No. 9,579,099) the contents of each being incorporated herein by reference in their entirety.

Extension assembly 200 includes an inner flexible band assembly 210 (FIG. 18), an outer flexible band assembly 230 (FIG. 19) slidably disposed about inner flexible band assembly 210, a frame assembly 250 (FIG. 20) for supporting inner and outer flexible band assemblies 210, 230, a trocar assembly 270 (FIG. 28) operably received through inner and outer flexible band assemblies 210, 230, and a connector assembly 290 for securing loading unit 40 (FIG. 34) to extension assembly 200. An outer sleeve 206 (FIG. 17) is received about frame assembly 250 and trocar assembly 270, and inner and outer flexible band assemblies 210, 230 are slidably received through outer sleeve 206. As will be described in further detail below, extension assembly 200 may include a drive shaft 208 operably connected to trocar assembly 270 and extending through proximal end 202 of extension assembly 200.

Figure 18:
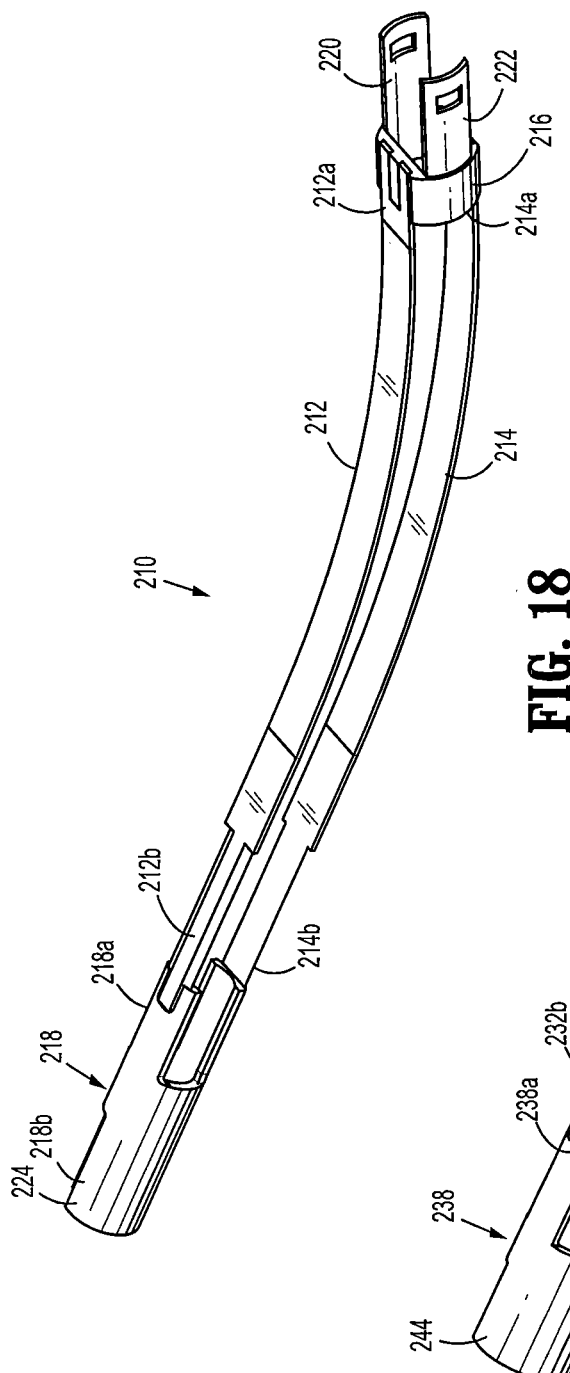
FIG. 18 is a perspective side view of an inner flexible band assembly of the extension assembly of FIG. 17.

With reference to FIG. 18, inner flexible band assembly 210 includes first and second inner flexible bands 212, 214, a support ring 216, a support base 218, and first and second connection extensions 220, 222. Proximal ends 212a, 214a of respective first and second inner flexible bands 212, 214 are laterally spaced apart and securely attached to support ring 216. Distal ends 212b, 214b of first and second inner flexible bands 212, 214 are laterally spaced apart and securely attached to a proximal end 218a of support base 218. Each of first and second inner flexible bands 212, 214 may be attached to support ring 216 and/or support base 218 in any suitable manner, including, for example, by press-fitting, welding, adhesives, and/or with mechanical fasteners. As will be described in further detail below, inner flexible band assembly 210 is configured to be slidably received about trocar assembly 270 (FIG. 28) and within outer flexible band assembly 230 (FIG. 19) and outer sleeve 206 (FIG. 17).

First and second connection extensions 220, 222 of inner flexible band assembly 210 extend proximally from support ring 216 and operably connect inner flexible band assembly 210 with pusher member 190 (FIG. 15) of second pusher assembly 180 (FIG. 15) of adapter assembly 100 (FIG. 3). In particular, each of first and second connection extensions 220, 222 define respective openings 221, 223 configured to receive tabs 198 (FIG. 15) of pusher member 190 (FIG. 15) of second pusher assembly 180. Receipt of tabs 198 of pusher member 190 within openings 221, 223 of respective first and second extensions 220, 222 secure inner flexible band assembly 210 of extension assembly 200 with second pusher assembly 180 of adapter assembly 100. First and second connection extensions 220, 222 may be integrally formed with support ring 216, or attached thereto in any suitable manner.

Figure 34:
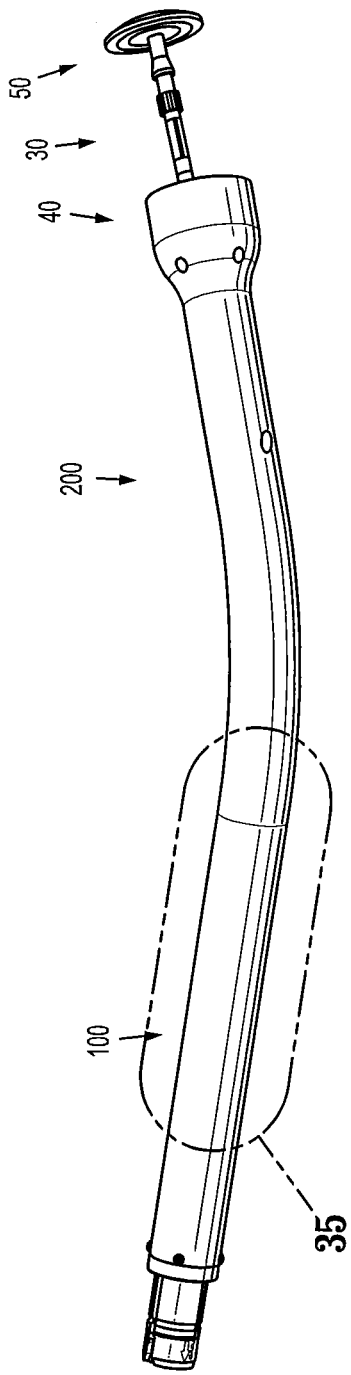
FIG. 34 is a perspective side view of the adapter assembly of FIG. 3 connected to the extension assembly of FIG. 17 and an end effector and an anvil assembly connected to the extension assembly.

Support base 218 extends distally from inner flexible bands 212, 214 and is configured to selectively connect extension assembly 200 with loading unit 40 (FIG. 34). Specifically, a distal end 218b of support base 218 includes a flange 224 for operable engagement with an axially movable assembly (not shown) of loading unit 40 (FIG. 34). In one embodiment, flange 224 is configured for connection with a knife assembly (not shown) of loading unit 40 (FIG. 34).

Figure 19:
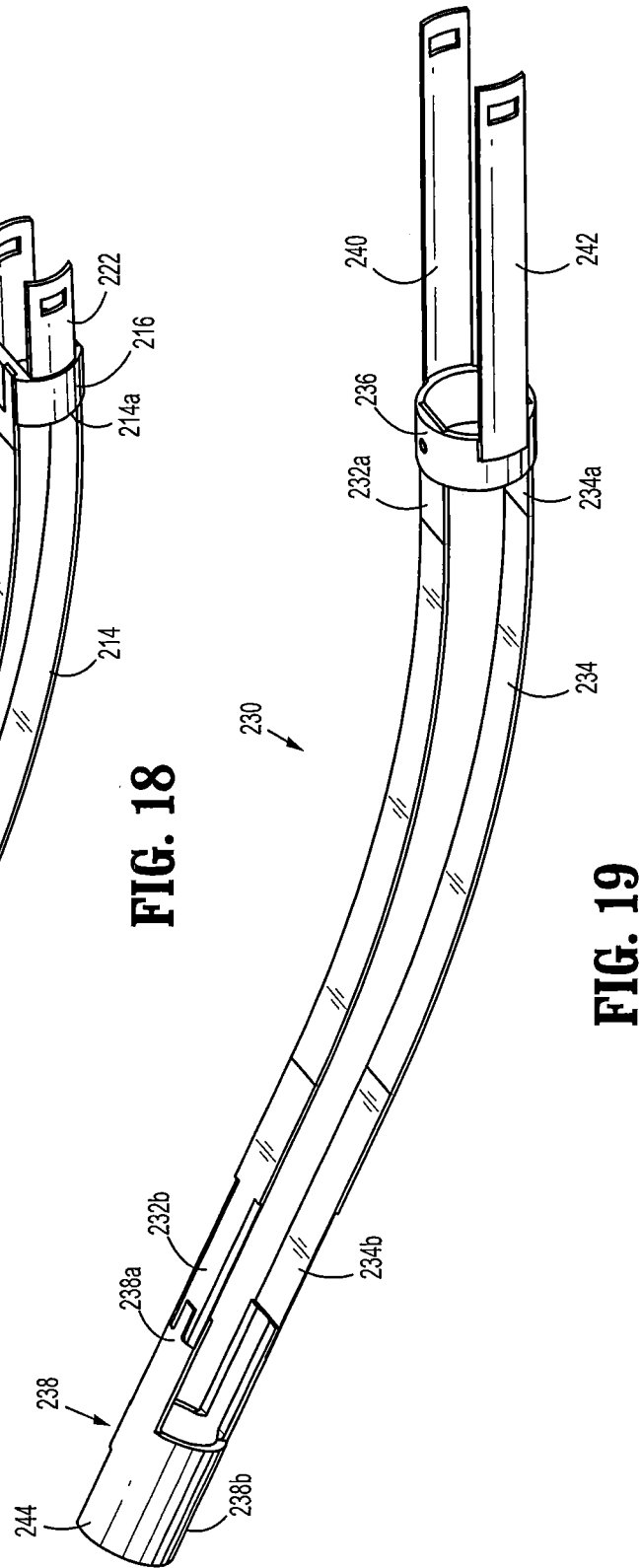
FIG. 19 is a perspective side view of an outer flexible band assembly of the extension assembly of FIG. 17.
Figure 20:
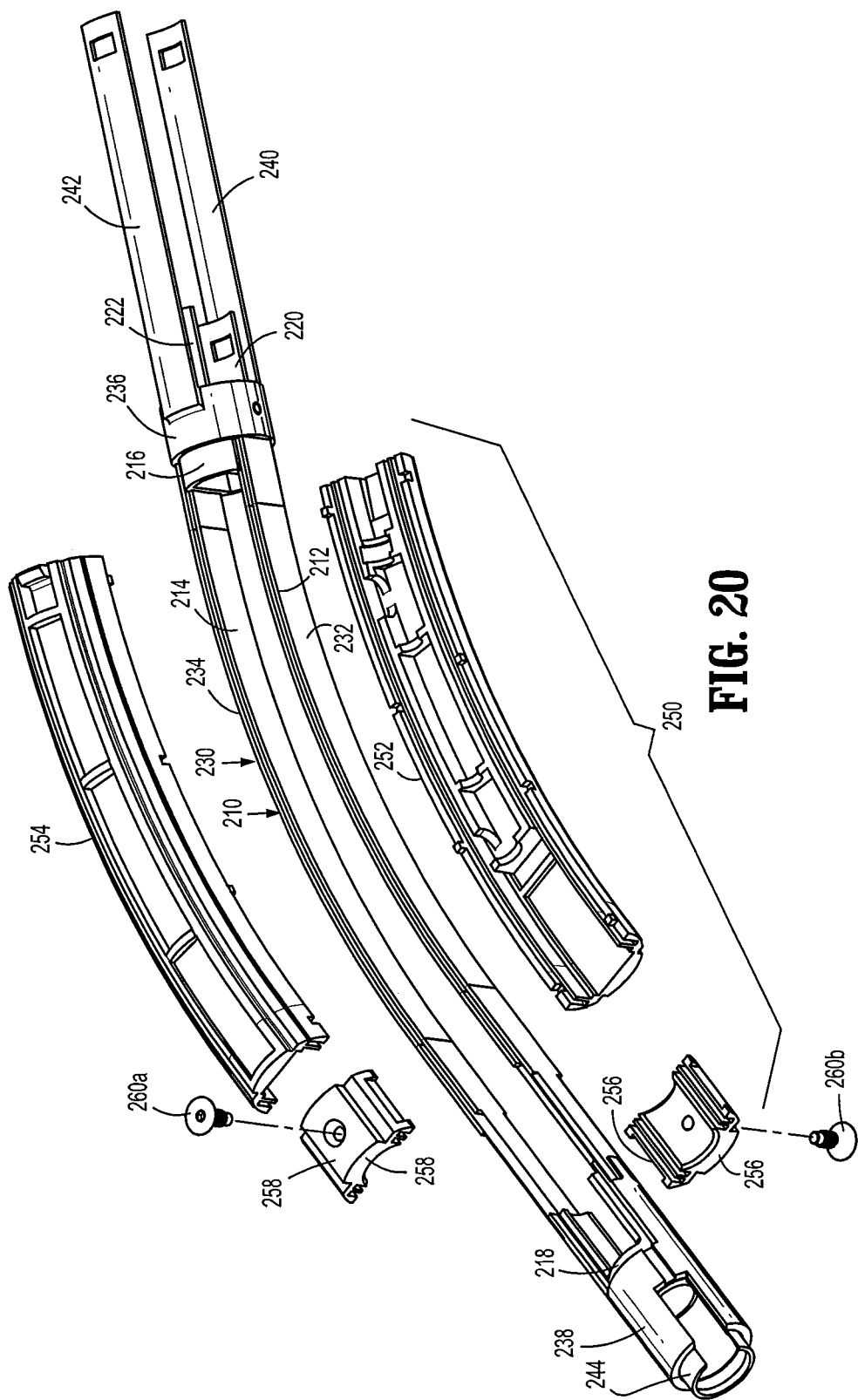
FIG. 20 is a perspective side view of the inner and outer flexible band assemblies of FIGS. 18 and 19 and an exploded view of a frame assembly of the extension assembly of FIG. 17.
Figure 21:
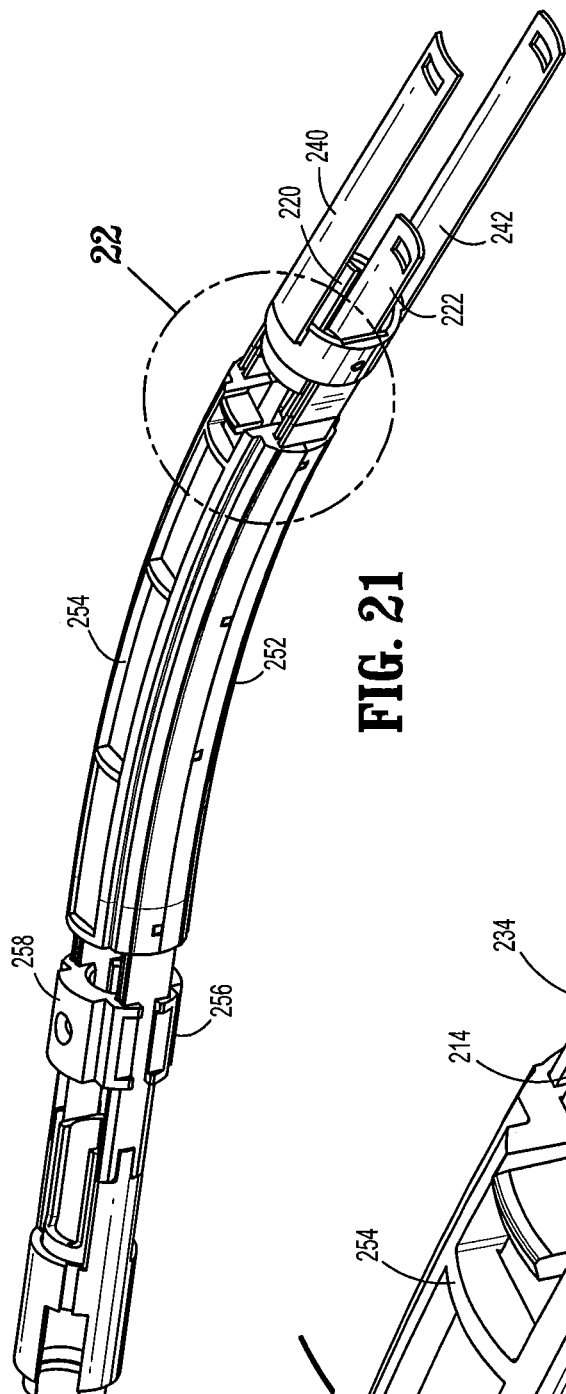
FIG. 21 is a perspective side view of the inner and outer flexible band assemblies and the frame assembly of FIG. 20.
Figure 22:
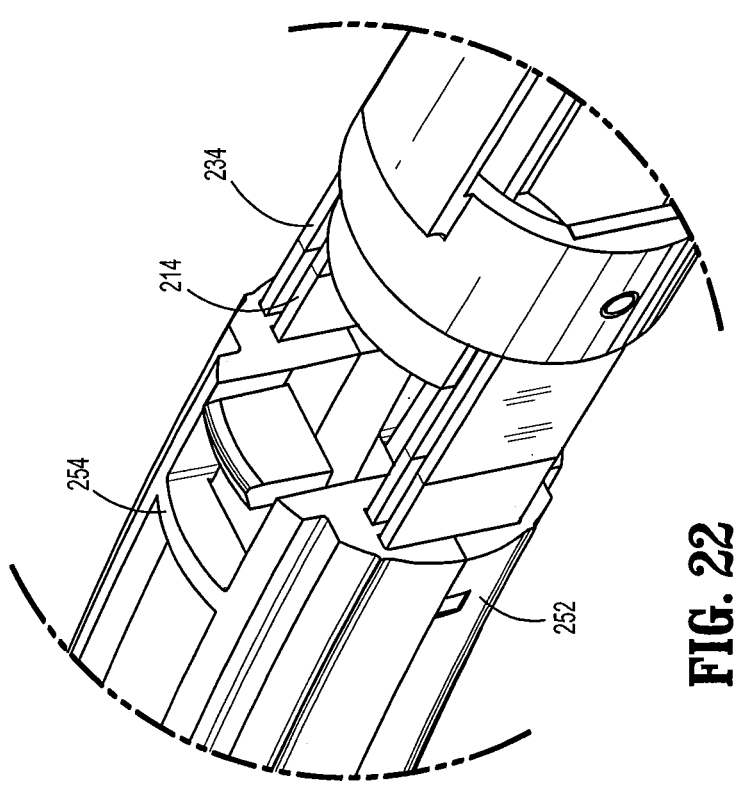
FIG. 22 is an enlarged view of the indicated area of detail of FIG. 21.
Figure 25:
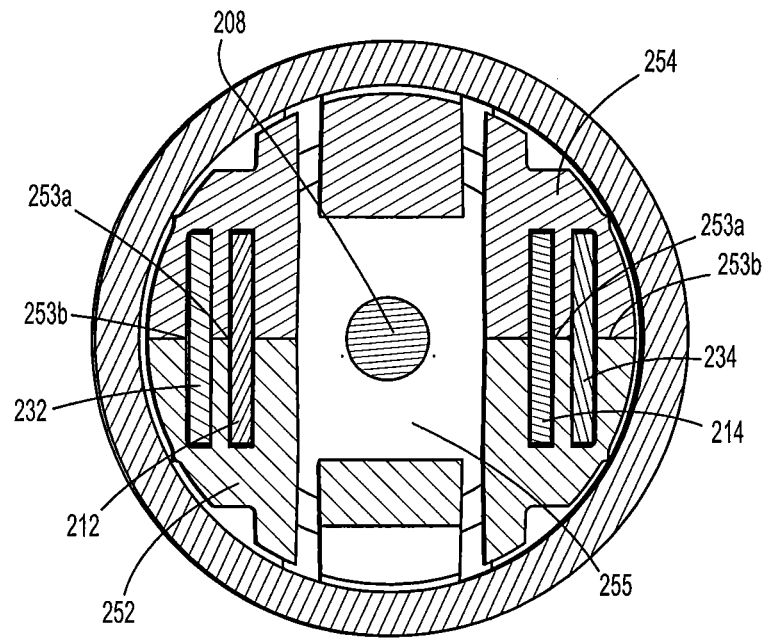
FIG. 25 is a cross-sectional end view taken along line 25-25 of FIG. 17.

With reference now to FIG. 19, outer flexible band assembly 230 is substantially similar to inner flexible band assembly 210 and includes first and second flexible bands 232, 234 laterally spaced and connected on proximal ends 232a, 234a to a support ring 236 and on distal ends 234b, 234b to a proximal end 238a of a support base 238. Each of first and second outer flexible bands 232, 234 may be attached to support ring 236 and support base 238 in any suitable manner, including, for example, by press-fitting, welding, adhesives, and/or with mechanical fasteners. As will be described in further detail below, outer flexible band assembly 230 is configured to receive trocar assembly 270 (FIG. 28) therethrough.

First and second connection extensions 240, 242 of outer flexible band assembly 230 extend proximally from support ring 236 and operably connect outer flexible band assembly 230 with pusher member 170 (FIG. 12) of first pusher assembly 160 (FIG. 12) of adapter assembly 100 (FIG. 1). In particular, each of first and second connection extensions 240, 242 define respective openings 241, 243 configured to receive tabs 178 (FIG. 12) of pusher member 170 of first pusher assembly 160. Receipt of tabs 178 of pusher member 170 within openings 241, 243 of respective first and second extensions 240, 242 secures outer flexible band assembly 230 of extension assembly 200 with first pusher assembly 160 of adapter assembly 100. First and second connection extensions 240, 242 may be integrally formed with support ring 236, or attached thereto in any suitable manner.

Support base 238 extends distally from outer flexible bands 232, 234 and is configured to selectively connect extension assembly 200 with loading unit 40 (FIG. 34). Specifically, a distal end 238b of support base 238 includes a flange 244 for operable engagement with an axially movable assembly (not shown) of a loading unit (not shown). In one embodiment, flange 244 is configured for connection with a staple pusher assembly (not shown) of loading unit 40 (FIG. 34).

With reference now to FIGS. 20-26, frame assembly 250 includes first and second proximal spacer members 252, 254, and first and second distal spacer members 256, 258. When secured together, first and second proximal spacer members 252, 254 define a pair of inner longitudinal slots 253a for slidably receiving first and second flexible bands 212, 214 (FIG. 18) of inner flexible band assembly 210 (FIG. 18) and a pair of outer longitudinal slots 253b for slidably receiving first and second flexible bands 232, 234 (FIG. 19) of outer flexible band assembly 230 (FIG. 19). First and second proximal spacer members 252, 254 further define a longitudinal passage 255 for receipt of trocar assembly 270.

In one embodiment, and as shown, first and second proximal spacer members 252, 254 are formed of plastic and are secured together with a snap-fit arrangement. Alternatively, first and second proximal spacer members 252, 254 may be formed of metal or other suitable material and may be secured together in any suitable manner, including by welding, adhesives, and/or using mechanical fasteners.

First and second distal spacer members 256, 258 define a pair of inner slots 257a for slidably receiving first and second flexible bands 212, 214 (FIG. 18) of inner flexible band assembly 210 (FIG. 18) and a pair of outer slots 257b for slidably receiving first and second flexible bands 232, 234 (FIG. 19) of outer flexible band assembly 230 (FIG. 19). First and second distal spacer members 256, 258 further define a longitudinal passage 259 for receipt of trocar assembly 270.

Figure 26:
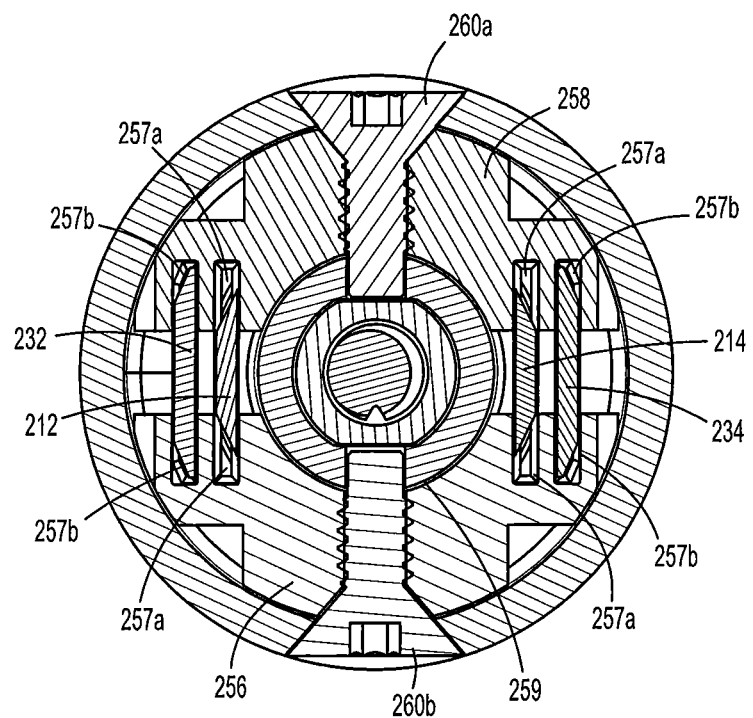
FIG. 26 is a cross-sectional end view taken along line 26-26 of FIG. 17.

In one embodiment, and as shown, each of first and second distal spacer members 256, 258 are secured about inner and outer flexible band assemblies 210, 230 and to outer sleeve 206 (FIG. 17) by a pair of screws 260a, 260b (FIG. 26). Alternatively, first and second distal spacer members 256, 258 may be secured together in any suitable manner, including by welding, adhesives, and/or using mechanical fasteners. First and second distal spacer members 256, 258 may be formed of metal or any other suitable material.

Figure 27:
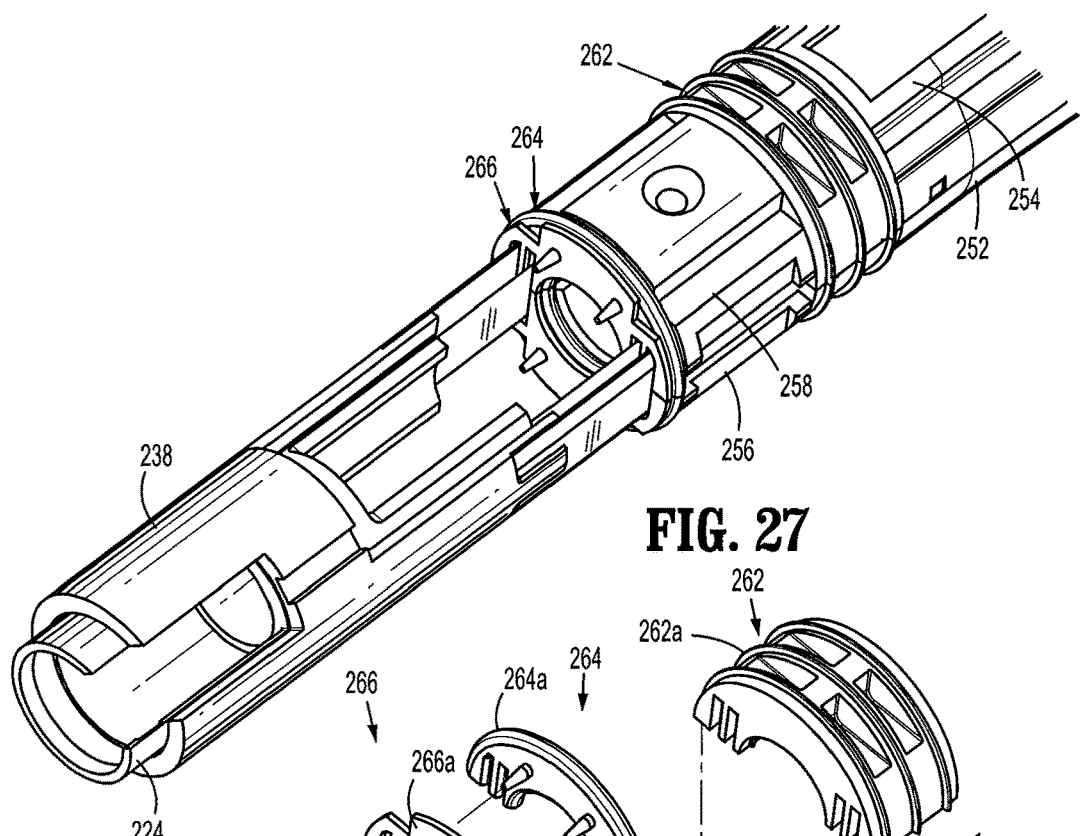
FIG. 27 is an enlarged perspective side view of a distal end of the inner and outer flexible band assemblies and the frame assembly of FIG. 20 including a proximal seal member and first and second distal seal members.
Figure 28:
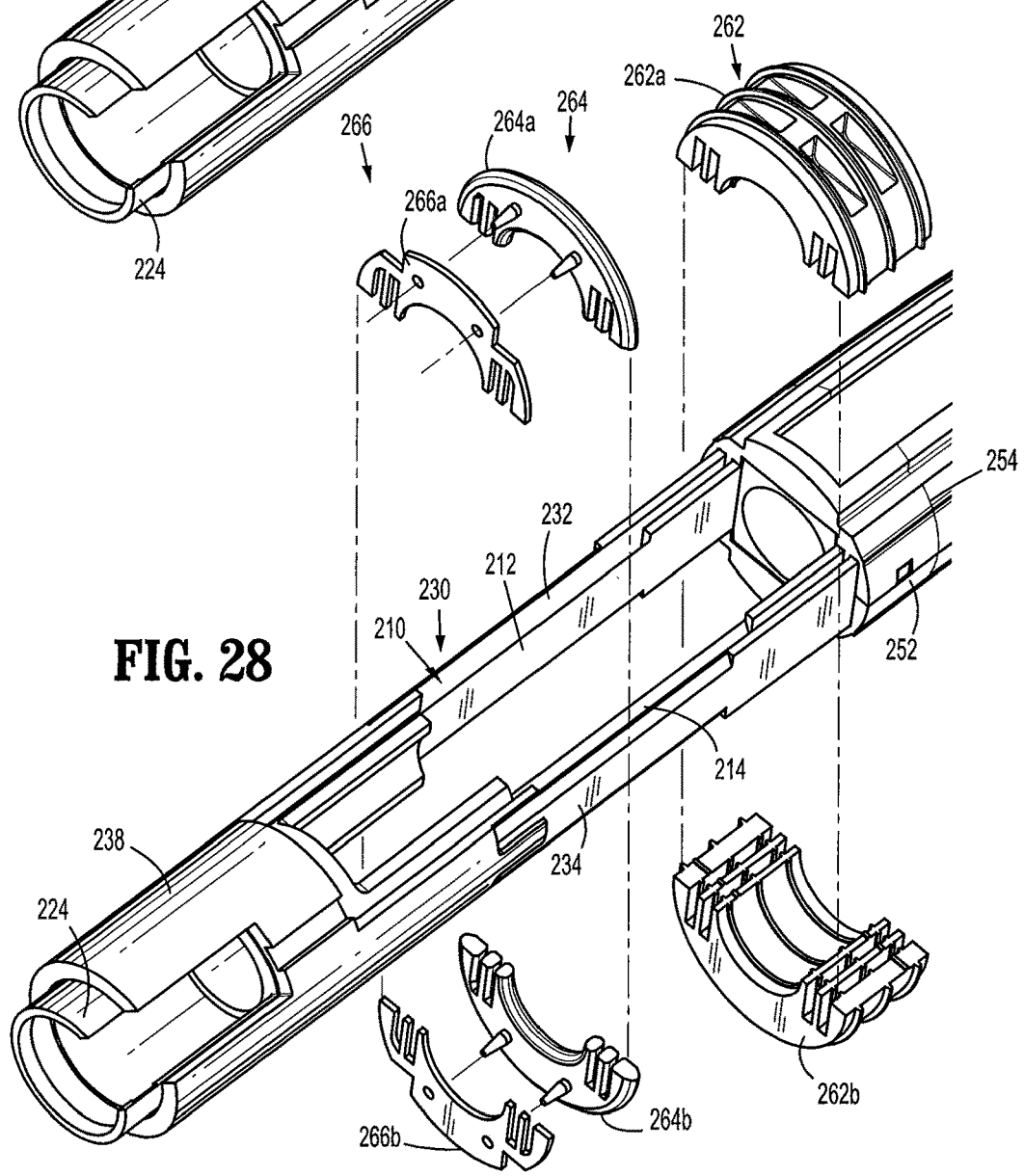
FIG. 28 is an exploded perspective view of the proximal seal member and first and second distal seal members of FIG. 27.
Figure 29:
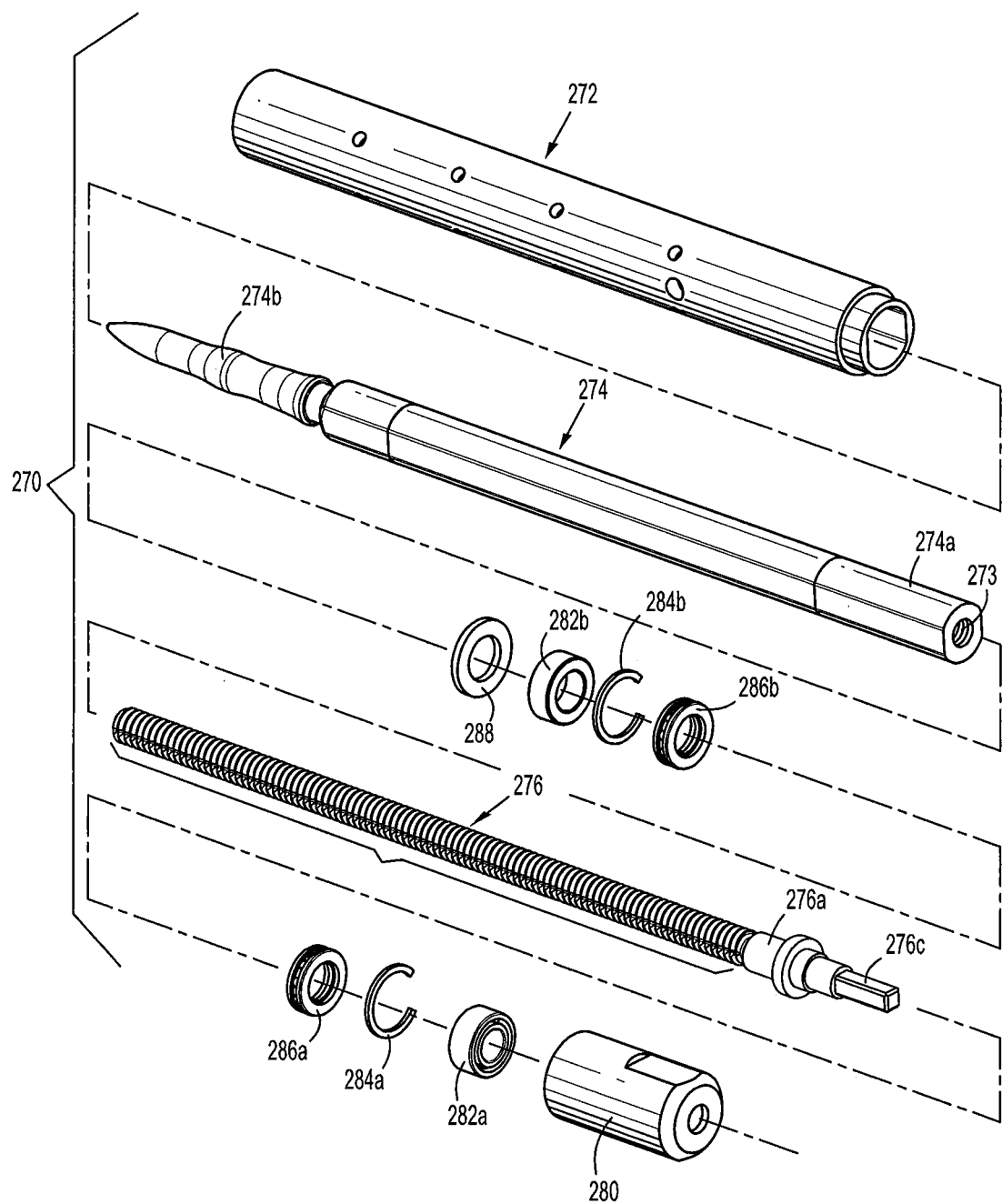
FIG. 29 is an exploded view of a trocar assembly of the extension assembly of FIG. 17.

With reference now to FIGS. 27 and 28, frame assembly 250 further includes a proximal seal member 262 and first and second distal seal members 264, 266. Each of proximal seal member 252 and first and second distal seal members 264, 266 include seals halves 262a, 262b, 264a, 264b, 266a, 266b, respectively. Proximal seal member 262 is received between first and second proximal spacer members 252, 254 and first and second distal spacer members 256, 258. First half 264a of first distal seal member 264 is secured to first half 266a of second distal seal member 266 and second half 264b of first distal seal member 264 is secured to second half of second distal seal member 266. Proximal seal member 262 and first and second distal seal members 264, 266 engage outer sleeve 206 (FIG. 17), inner and outer flexible bands 212, 214 and 232, 234 of respective inner and outer flexible band assemblies 210, 230 and trocar assembly 270 (FIG. 28) in a sealing manner. In this manner, proximal seal member 262 and first and second distal seal members 264, 266 operate to provide a fluid tight seal between distal end 204 and proximal end 202 of extension assembly 200.

With reference to FIGS. 29-32, trocar assembly 270 of extension assembly 200 includes an outer housing 272, a trocar member 274 slidably disposed within tubular outer housing 272, and a drive screw 276 operably received within trocar member 274 for axially moving trocar member 274 relative to tubular housing 272. In particular, trocar member 274 includes a proximal end 274a having an inner threaded portion 275 which engages a threaded distal portion 276b of drive screw 276. As drive screw 276 is rotated within trocar member 274, engagement of inner threaded portion 275 of trocar member 274 with threaded distal portion 276b of drive screw 276 causes longitudinal movement of trocar member 274 within outer housing 272 of trocar assembly 270. Rotation of drive screw 276 in a first direction causes longitudinal advancement of trocar member 274 and rotation of drive screw 276 in a second direction causes longitudinal retraction of trocar member 274. A distal end 274*b* of trocar member 274 is configured to selectively engage anvil assembly 50 (FIG. 34).

A bearing assembly 278 is mounted to a proximal end 272*a* of outer housing 272 of trocar assembly 270 for rotatably supporting a proximal end 276*a* of drive screw 276 relative to outer housing 272 and trocar member 274. Bearing assembly 278 includes a housing 280, proximal and distal spacers 282*a*, 282*b*, proximal and distal retention clips 284*a*, 284*b*, proximal and distal bearings 286*a*, 286*b*, and a washer 288. As shown, proximal end 276*a* of drive screw 276 includes a flange 276*c* for connection with a link assembly 277. A distal portion 277*b* of link assembly 277 is pivotally received between first and second proximal spacer members 252, 254 and operably engages flange 276*c* on drive screw 276. A proximal end 277*a* of link assembly 277 is configured for operable engagement with a distal end 208*b* of drive shaft 208.

With reference now to FIGS. 32 and 33, connector assembly 290 of extension assembly 200 includes a tubular connector 292 attached to a distal end 206*a* of outer sleeve 206 and about distal ends of inner and outer flexible assemblies 210, 230 (FIG. 26) and trocar assembly 270. In particular, a proximal end 292*a* of tubular connector 292 is received within and securely attached to distal end 206*b* of outer sleeve 206 by a retaining clip 294. An O-ring 296 forms a fluid tight seal between tubular connector 292 of connector assembly 290 and outer sleeve 206. A distal end 292*b* of tubular connector 292 is configured to selectively engage a proximal end of loading unit 40 (FIG. 34). Distal end 292*b* of tubular connector 292 engages the circular loading unit with a snap-fit arrangement, bayonet coupling, or in another suitable manner.

Figure 35:
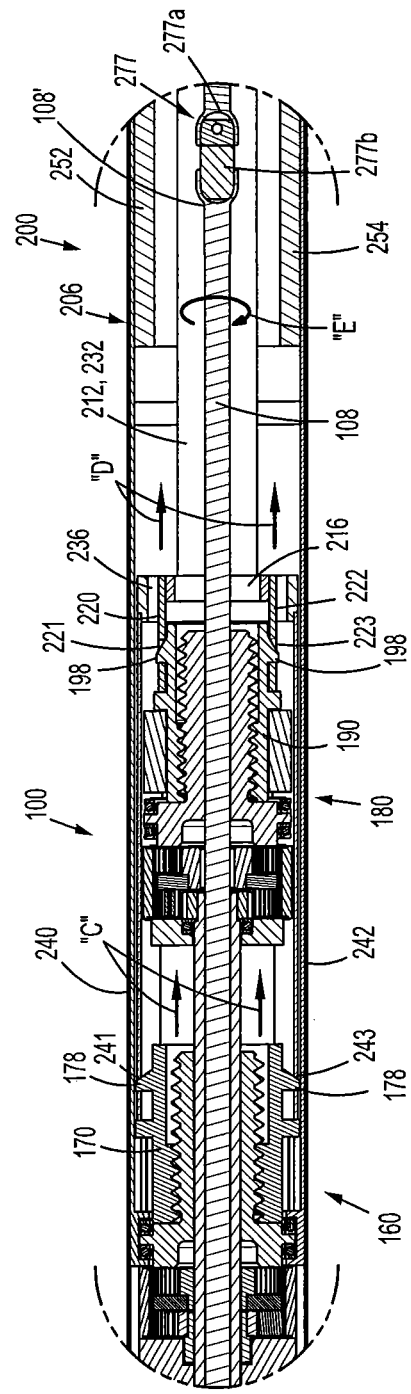
FIG. 35 is an enlarged cross-sectional side view of the indicated area of detail of FIG. 34.
Figure 36:
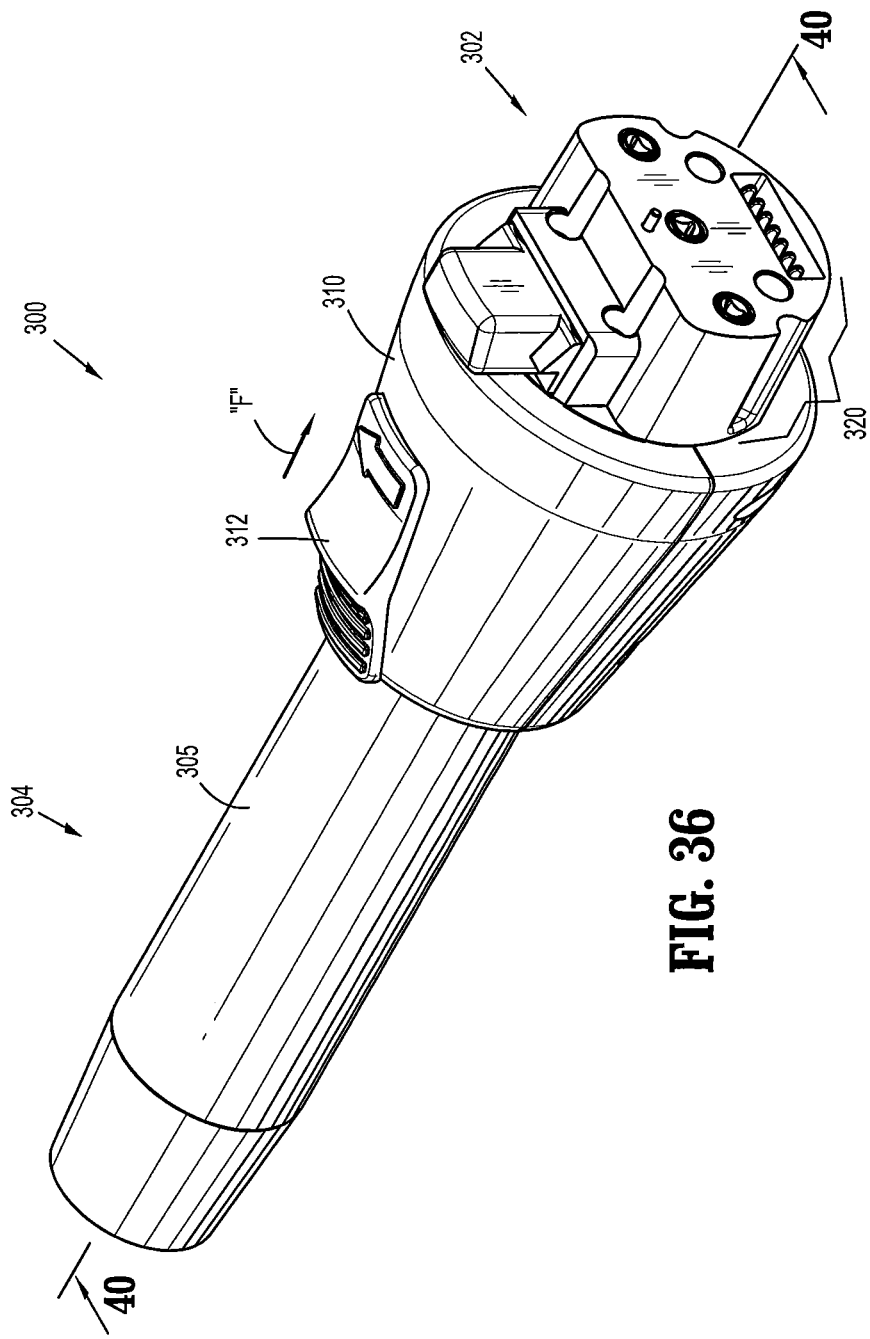
FIG. 36 is a rear, perspective view of an adapter assembly according to another embodiment of the present disclosure.
Figure 37:
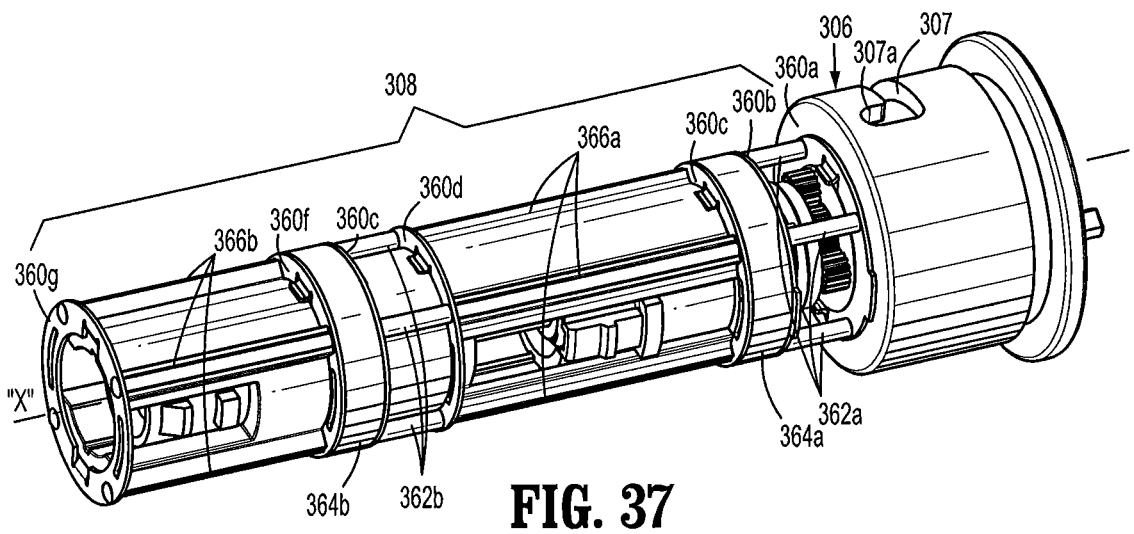
FIG. 37 is a perspective side view of the adapter assembly of FIG. 36 with an outer sleeve and a handle member removed.
Figure 38:
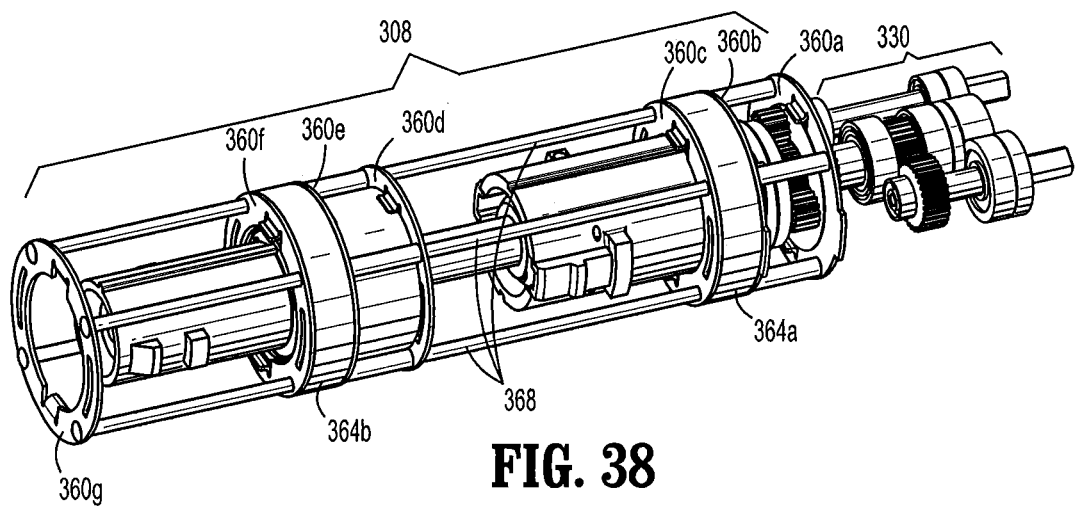
FIG. 38 is a perspective side view of the adapter assembly of FIG. 37 with a base and a housing member removed.
Figure 39:
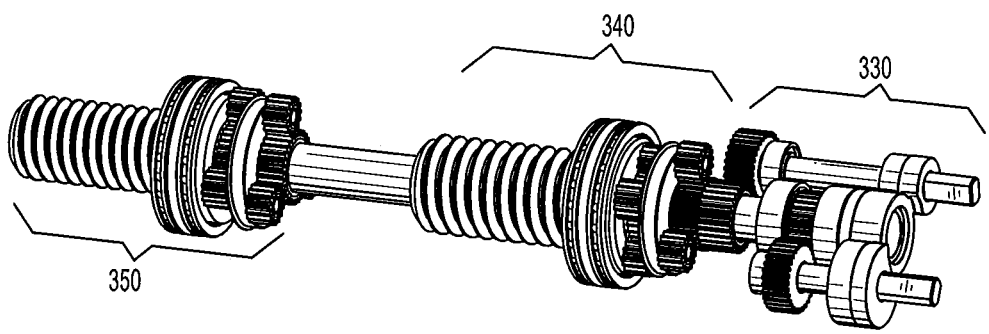
FIG. 39 is a perspective side view of the adapter assembly of FIG. 38 with a support structure removed.

With reference now to FIGS. 34 and 35, extension assembly 200 is connected to adapter assembly 100 by receiving proximal end 202 (FIG. 17) of extension assembly 200 within distal end 104 of adapter assembly 100. In particular, first and second connection extensions 220, 240, 222, 242 of respective inner and outer flexible band assemblies 210, 230 are received within sleeve 106 of adapter assembly 100 such that tabs 178 of pusher member 170 of first pusher assembly 160 of adapter assembly 100 are received within openings 241, 243 of respective first and second connection extensions 240, 242 of outer flexible band assembly 230 to secure outer flexible band assembly 230 with first pusher assembly 160 and tabs 198 of pusher member 190 of second pusher assembly 180 of adapter assembly 100 are received within openings 221, 223 of first and second connection extensions 221, 223 of inner flexible band assembly 210 to secure inner flexible band assembly 210 with second pusher assembly 180.

Figure 12:
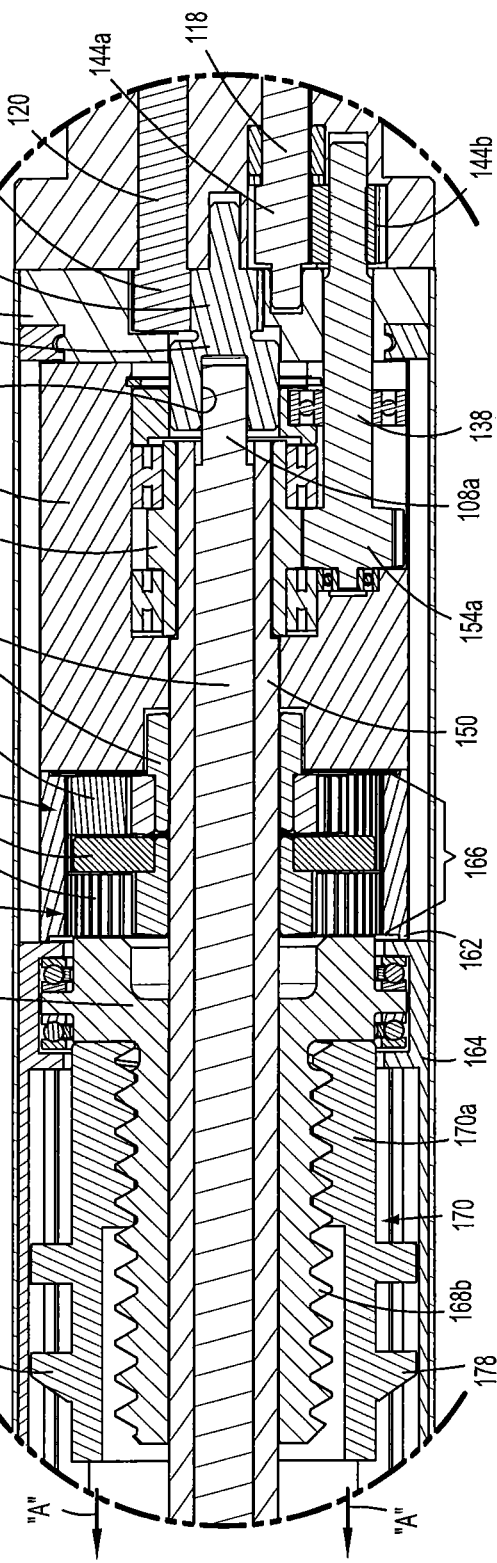
FIG. 12 is an enlarged view of the indicated area of detail of FIG. 7.
Figure 13:
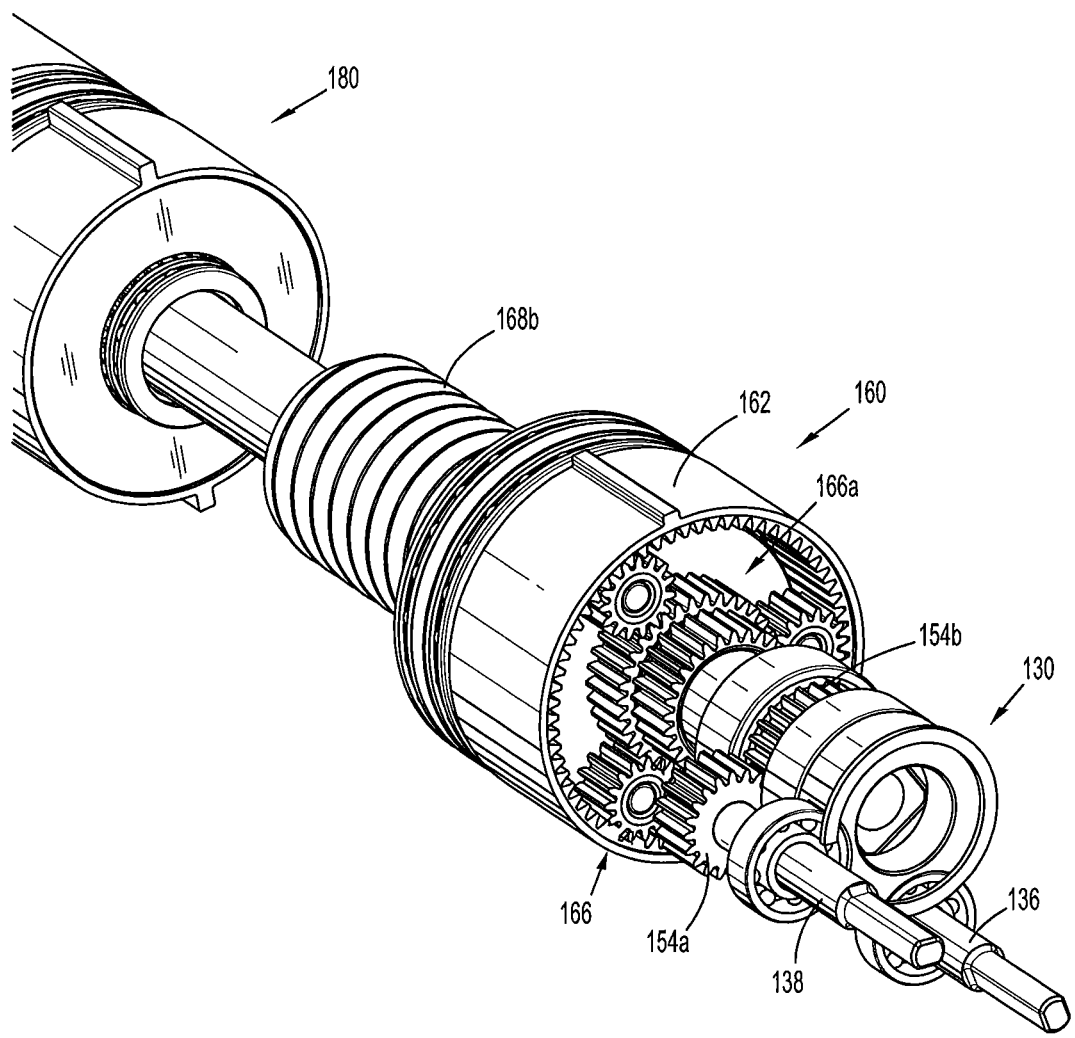
FIG. 13 is a perspective end view of the transfer assembly of FIG. 8.

As noted above, adapter assembly 100 may include a drive shaft 108 (FIG. 3) that extends from distal end 104 of adapter assembly 100. Alternatively, extension assembly 200 may include a drive shaft 208 extending from proximal portion 202 of extension assembly 200. In the event both adapter assembly 100 includes drive shaft 108 and extension assembly 200 includes drive shaft 208, prior to receipt of proximal portion 202 of extension assembly 200 within distal end 104 of extension assembly 100, one of drive shaft 108, 208 must be removed from respective adapter assembly 100 and extension assembly 200. During receipt of proximal portion 202 of extension assembly 200 within distal end 102 of adapter assembly 100, either distal end 108*b* (FIG. 35) of drive shaft 108 (FIG. 35) engages proximal portion 277*b* (FIG. 35) of link assembly 277, or proximal end 208*a* (FIG. 17) of drive shaft 208 (FIG. 17) is received within socket 145 of drive member 140 of drive transfer assembly 130 of extension assembly 100 (FIG. 12).

After extension assembly 200 is operably engaged with adapter assembly 100, and adapter assembly 100 is operably engaged with surgical device 10 (FIG. 1), loading unit 40 (FIG. 34) of end effector 30 (FIG. 34) may be attached to connector assembly 290 of extension assembly 200 and an anvil assembly 50 (FIG. 34) may be attached to distal end 274*b* of trocar 274 of extension assembly 200 in a conventional manner. During actuation of loading unit 40 and anvil assembly 50, longitudinal advancement of pusher member 190 of second pusher assembly 180 of adapter assembly 100, as described above, and as indicated by arrows "C" in FIG. 35, causes longitudinal advancement of outer flexible band assembly 230 of extension assembly 200 and longitudinal advancement of pusher member 170 of first pusher assembly 160, as described above, and as indicated by arrows "D" in FIG. 35, causes longitudinal advancement of inner flexible band assembly 210. Rotation of drive shaft 108 in a first direction, as described above, and as indicated by arrow "E", causes advancement of trocar 274 of extension assembly 200. Conversely, longitudinal retraction of pusher member 190 causes longitudinal retraction of outer flexible band assembly 230, longitudinal retraction of pusher member 170 causes longitudinal retraction of inner flexible band assembly 210, and rotation of drive shaft 108 in a second direction causes retraction of trocar 274 of extension assembly 200.

In one embodiment, inner flexible band assembly 210 is operably connected to a knife assembly (not show) of loading unit 40 (FIG. 34) of end effector 30 (FIG. 34) attached to connector assembly 290 of extension assembly 200, outer flexible band assembly 230 is operably connected to a staple driver assembly (not shown) of loading unit 40, and trocar 274 is operably connected to anvil assembly 50 (FIG. 34) of end effector 30 (FIG. 34). In this manner, longitudinal movement of inner flexible band assembly 210 causes longitudinal movement of the knife assembly, longitudinal movement of outer flexible band assembly 230 causes longitudinal movement of the staple driver assembly, and longitudinal movement of trocar 274 causes longitudinal movement of anvil assembly 50 relative to loading unit 40.

With reference to FIGS. 36-41, an adapter assembly according to another embodiment of the present disclosure is shown as adapter assembly 300. Adapter assembly 300 is substantially similar to adapter assembly 100 described hereinabove and will only be described as it relates to the differences therebetween.

As will become apparent from the following description, the configuration of adapter assembly 300 permits rotation of a distal portion 304 of adapter assembly 300 about a longitudinal axis "X" (FIG. 37), relative to a proximal portion 302 of adapter assembly 300. In this manner, an end effector, e.g. end effector 30 (FIG. 34) secured to distal portion 304 of adapter assembly 300 or an end effector secured to an extension assembly, e.g., extension assembly 200 (FIG. 17) which is secured to distal portion 304 of adapter assembly 300 is rotatable about longitudinal axis "X" independent of movement of the surgical device (not shown) to which adapter assembly 300 is attached.

Adapter assembly 300 includes a base 306 and a support structure 308 rotatable relative to base 306 along longitudinal axis "X" of adapter assembly 300. A rotation handle 310 is rotatably secured to base 306 and fixedly secured to a proximal end of support structure 308. Rotation handle 310 permits longitudinal rotation of distal portion 304 of adapter assembly 300 relative to proximal end 302 of adapter assembly 300. As will be described in further detail below, a latch 312 is mounted to rotation handle 310 and selectively secures rotation handle 310 in a fixed longitudinal position.

Proximal portion 302 of adapter assembly 300 includes a drive coupling assembly 320 and a drive transfer assembly 330 operably connected to drive coupling assembly 320. Distal portion 304 of adapter assembly 300 includes a first pusher assembly 340 operably connected to drive transfer assembly 330, and a second pusher assembly 350 operably connected to drive transfer assembly 330. Drive coupling assembly 320 and drive transfer assembly 330 are mounted within base 306, and thus, remain rotationally fixed relative to the surgical device (not shown) to which adapter assembly 300 is attached. First pusher assembly 340 and second pusher assembly 350 are mounted within support structure 308, and thus, are rotatable relative to the surgical device (not shown) to which adapter assembly 300 is attached.

Drive coupling assembly 320 is configured to selectively secure adapter assembly 300 to a surgical device (not shown). For a detailed description of an exemplary surgical device and drive coupling assembly, please refer to commonly owned U.S. Provisional Patent Application No. 61/913,572, filed Dec. 9, 2013, (U.S. patent application Ser. No. 14/550,183, now U.S. Pat. No. 10,561,417, claims the benefit of U.S. Provisional Patent Application No. 61/913, 572) the content of which is incorporated by reference herein in its entirety.

Rotation knob 310 is rotatably secured to base 306. Latch 312 includes a pin 312a (FIG. 40) configured to lock rotation knob 310 relative to base 306. In particular, pin 312a of latch 312 is received within a slot 307 formed in base 306 and is biased distally by a spring 314 into a notch 307a (FIG. 40) formed in base 306 and in communication with slot 307 to lock rotation knob 310 relative to base 306. Proximal movement of latch 312, as indicated by arrow "F" in FIG. 36, retracts pin 312a from within notch 307a to permit rotation of rotation knob 310 relative to base 306. Although not shown, it is envisioned that base 306 may define a number of notches radially spaced about base 306 and in communication with slot 307 that permit rotation knob 310 to be locked in a number of longitudinal orientations relative to base 306.

Drive transfer assembly 330, first drive pusher assembly 340, and second drive pusher assembly 350 of adapter assembly 300 are substantially identical to respective drive transfer assembly 130, first drive pusher assembly 160, and second drive pusher assembly 180 of adapter assembly 100 described hereinabove, and therefore, will only be described as relates to the differences therebetween.

Support structure 308 is fixedly received about first and second drive pusher assemblies 340, 350 and rotatably relative to base 306. As noted above, rotation knob 310 is fixedly secured to the proximal end of support structure 308 to facilitate rotation of support structure 308 relative to base 306. Support structure 308 is retained with outer sleeve 305 of adapter assembly 300 and is configured to maintain axial alignment of first and second drive pusher assemblies 340, 350. Support structure 308 may also reduce the cost of adapter assembly 300 when compared to the cost of adapter assembly 100.

Support structure 308 respectively includes first, second, third, fourth, fifth, sixth, and seventh plates 360a, 360b, 360c, 360d, 360e, 360f, 360g, a first and a second plurality of tubular supports 362a, 362b, first and second support rings 364a, 364b, a first and a second plurality of ribs 366a, 366b, and a plurality of rivets 368. From proximal to distal, first and second plates 360a, 360b are maintained in spaced apart relation to each other by the first plurality of tubular supports 362a, second and third plates 360b, 360c are maintained in spaced apart relation to each other by first support ring 364a, third and fourth plates 360c, 360d are maintained in spaced apart relation to each other by the first plurality of support ribs 366a, fourth and fifth plates 360d, 360e are maintained in spaced apart relation to each other by the second plurality of tubular supports 362b, fifth and sixth plates 360e, 360f are maintained in spaced apart relation to each other by second support ring 364b, and sixth and seventh plates 360f, 360g are maintained in spaced apart relation to each other by the second plurality of support ribs 366b. First, second, third, fourth, fifth, sixth, and seventh plates 360a-g are held together by a plurality of rivets 368 secured to first and seventh plates 360a, 360g and extending through second, third, fourth, fifth, and sixth plates 360b-360f, first and second support rings 364a, 364b, and respective first and second plurality of tubular support 362a, 362b.

Adapter assembly 300 operates in a substantially similar manner to adapter assembly 100 described hereinabove. In addition, as described in detail above, adapter assembly 300 is configured to permit rotation of an end effector, e.g., end effector 30 (FIG. 34) attached to adapter assembly 300 or attached to an extension assembly that is attached to adapter assembly 300 to be selectively rotated about longitudinal axis "X" (FIG. 37) during use.

Figure 42:
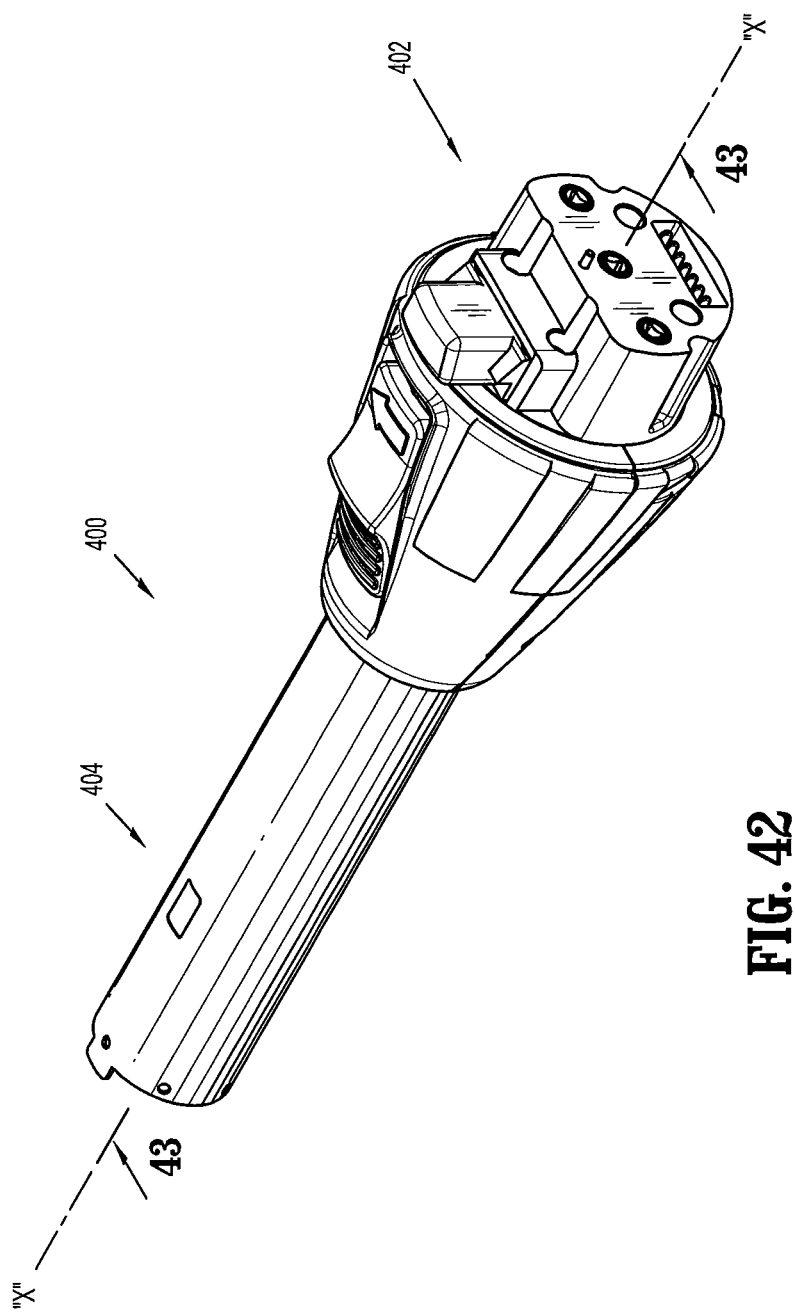
FIG. 42 is a rear, perspective view of an adapter assembly according to yet another embodiment of the present disclosure.
Figure 43:
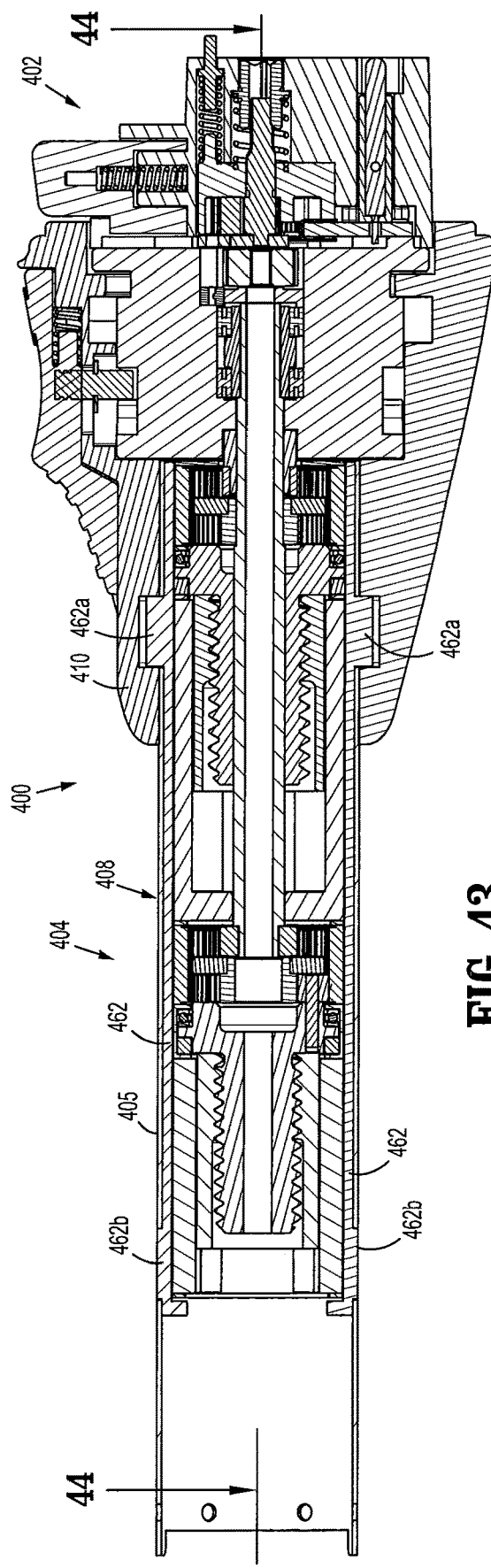
FIG. 43 is a cross-sectional side view taken along line 43-43 of FIG. 42.
Figure 44:
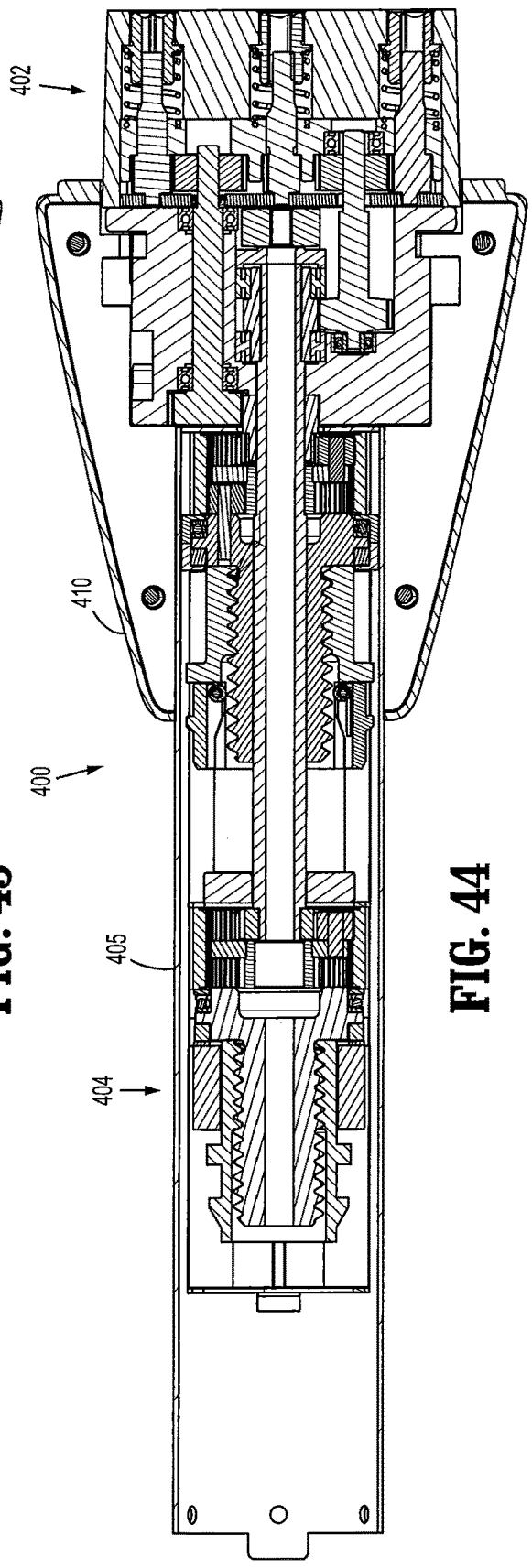
FIG. 44 is a cross-sectional side view taken along line 44-44 of FIG. 42.
Figure 45:
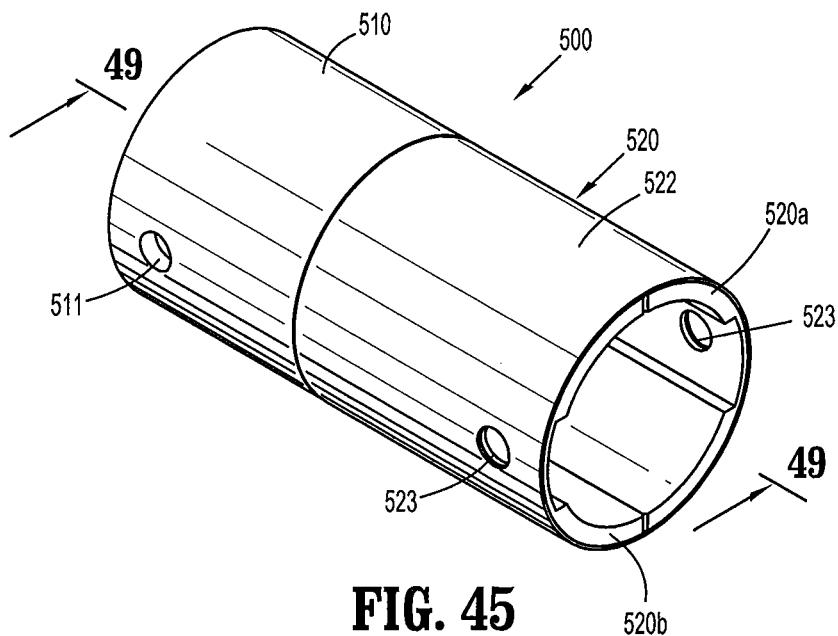
FIG. 45 is a perspective view of a connector assembly according to an embodiment of the present disclosure.
Figure 46:
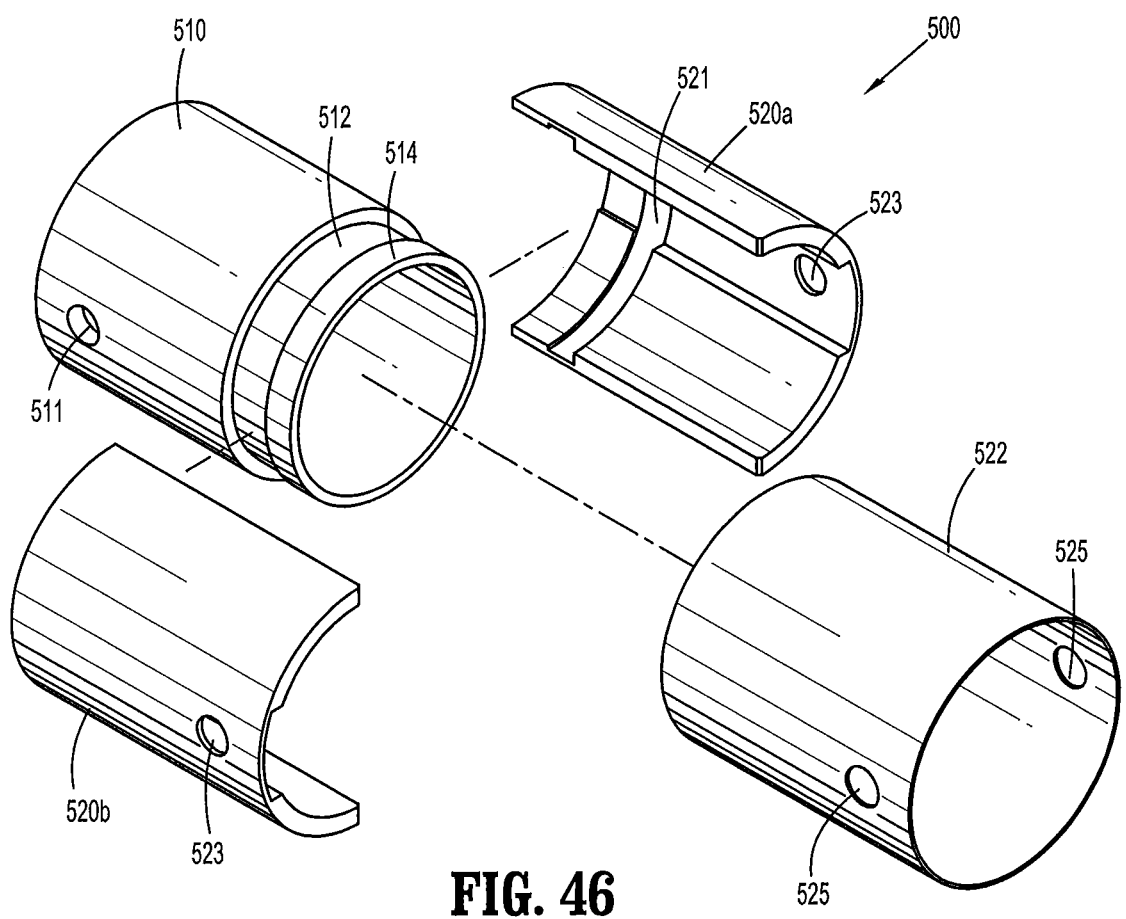
FIG. 46 is an exploded perspective view of the connector assembly of FIG. 45.
Figure 47:
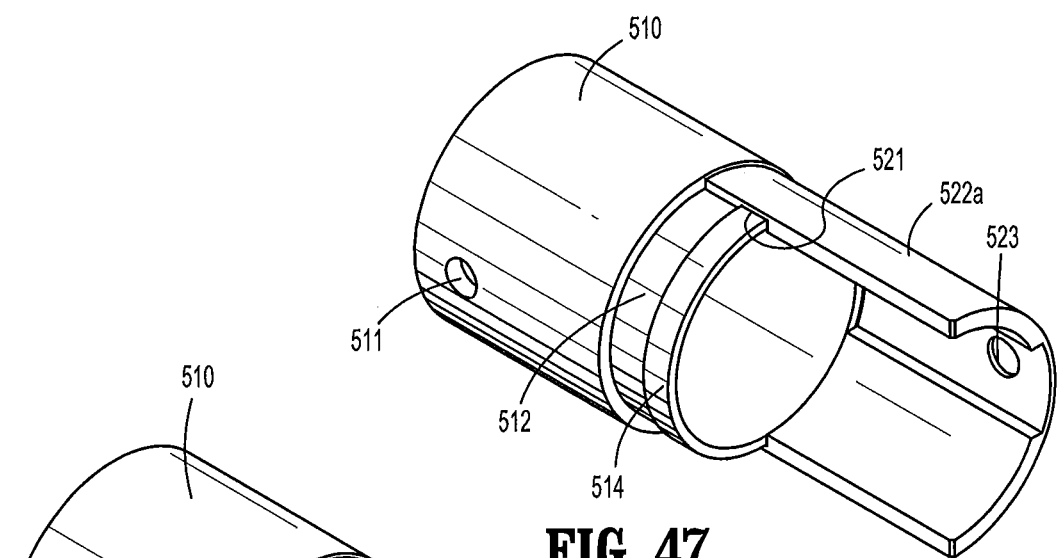
FIG. 47 is a perspective view of the connector assembly of FIG. 45 with a sleeve and first section of a tubular extension removed.
Figure 48:
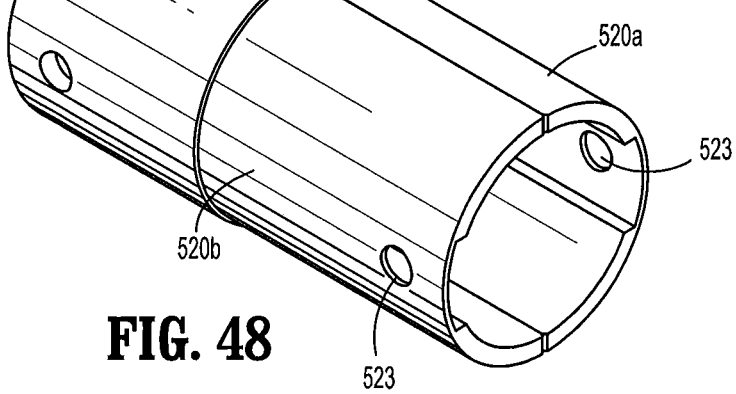
FIG. 48 is a perspective view of the connector assembly of FIG. 45 with the sleeve removed.
Figure 49:
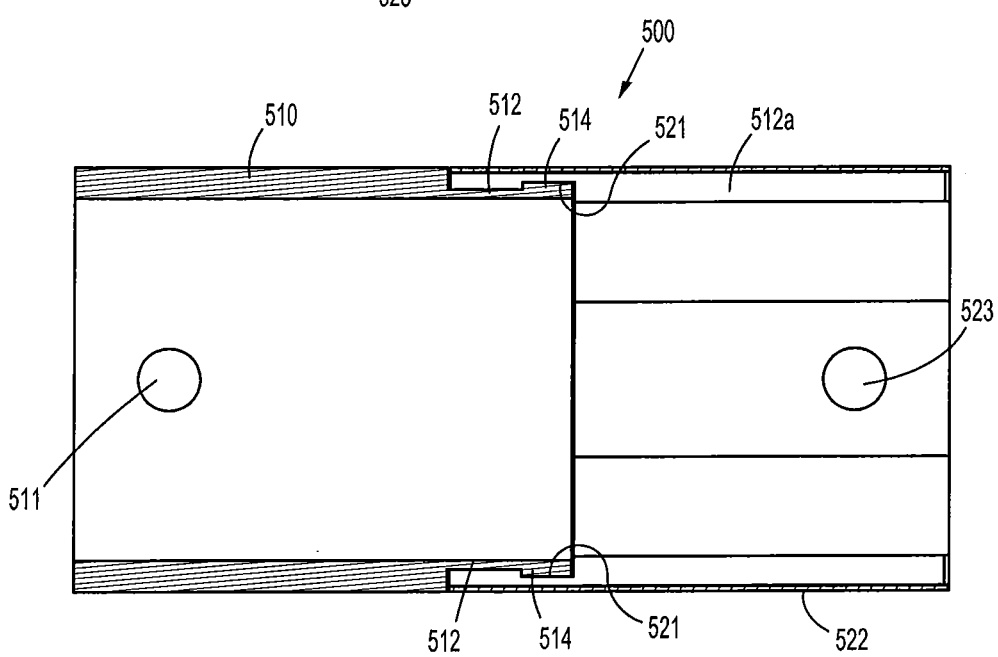
FIG. 49 is a cross-sectional side view taken along line 49-49 of FIG. 45.

With reference now to FIGS. 42-44, an adapter assembly according to another embodiment of the present disclosure is shown generally as adapter assembly 400. Adapter assembly 400 is substantially similar to adapter assemblies 100 and 300 described hereinabove, and therefore will only be described as relates to the differences therebetween.

Adapter assembly 400 includes a proximal portion 402 and a distal portion 404 rotatable along a longitudinal axis "X" relative to proximal portion 402. Distal portion 404 includes a support structure 408 secured to outer sleeve 405 and formed about first and second pusher assemblies 440, 450. Support structure 408 includes a plurality of reinforcing members 462 extending substantially the length of outer sleeve 405. Reinforcing members 462 each include a proximal tab 462a and a distal tab 462b which extend through outer sleeve 405 to secure reinforcing member 462 within outer sleeve 405. Proximal tabs 462 of reinforcing members 462 are further configured to engage a rotation knob 410 of adapter assembly 400. Adapter assembly 400 may include annular plates (not shown) positioned radially inward of reinforcing members 462 that maintain proximal and distal tabs 462a, 462b of reinforcing members 462 in engagement with outer sleeve 405. The annular plates may also provide structure support to distal portion 404 of adapter assembly 400.

With reference to FIGS. 45-49, a connection assembly according to an embodiment of the present disclosure is shown generally as connection assembly 500. As shown and will be described, connection assembly 500 is configured to be attached to first and second tubular bodies (not shown) for connecting the first tubular body, i.e., adapter assembly 100 (FIG. 3), 300 (FIG. 36), 400 (FIG. 42), to the second tubular body, i.e., extension assembly 200 (FIG. 17). It is envisioned, however, that the aspects of the present disclosure may be incorporated directly into the first and second tubular bodies to permit connection of the first tubular body directly to the second tubular body.

Connection assembly 500 includes a tubular base 510 and a tubular extension 520 formed of first and second sections 520a, 520b and an outer sleeve 522. As shown, tubular base 510 defines a pair of openings 511 for securing tubular base 510 to a first tubular body (not shown). Alternatively, tubular base 510 may include only a single opening, one or more tabs (not shown), and/or one or more slots (not shown), for securing tubular base 510 to the first tubular body (not shown). A flange 512 extends from a first end of tubular base 510 and includes an annular rim 514 extending thereabout.

First and second sections 520a, 520b of tubular extension 520 are substantially similar to one another and each define an annular groove 521 formed along an inner first surface thereof. Each of first and second section 520a, 520b of tubular extension 520 is configured to be received about flange 512 of tubular base 510 such that rim 514 of tubular base 510 is received within grooves 521 of first and second sections 520a, 520b of tubular extension 520. Once first and second sections 520a, 520b of tubular extension 520 are received about flange 512 of tubular base 510, outer sleeve 522 of tubular extension 520 is received about first and second sections 520a, 520b of tubular extension 520 to secure tubular extension 520 to tubular base 510.

As shown, each of first and second sections 520a, 520b of tubular extension 520 define an opening 523 configured to be aligned with a pair of openings 525 in outer sleeve 522 to secure outer sleeve 522 to first and second sections 520a, 520b. Either or both of first and second sections 520a, 520b and outer sleeve 522 may include one or more tabs, and/or one or more slots for securing outer sleeve 522 about first and second extensions. Alternatively, outer sleeve 522 may be secured to first and second sections 520a, 520b in any suitable manner.

Outer sleeve 522 may be selectively secured about first and second extensions for selective removal of outer sleeve 522 from about first and second sections 520a, 520b to permit separation of tubular extension 520 from tubular base 510. Alternatively, outer sleeve 522 may be permanently secured about first and second sections 520a, 520b to prevent tubular extension 520 from being separated from tubular base 510. As noted above, although tubular base 510 and tubular extension 520 are shown and described as forming an independent connection assembly 500, it is envisioned that tubular base 510 may be formed on a first tubular member, i.e., adapter assembly 100 (FIG. 3) and tubular extension 520 may be formed on a second tubular member, i.e., extension assembly 200 (FIG. 17) such that the first tubular member may be directly connected to the second tubular member.

Figure 50:
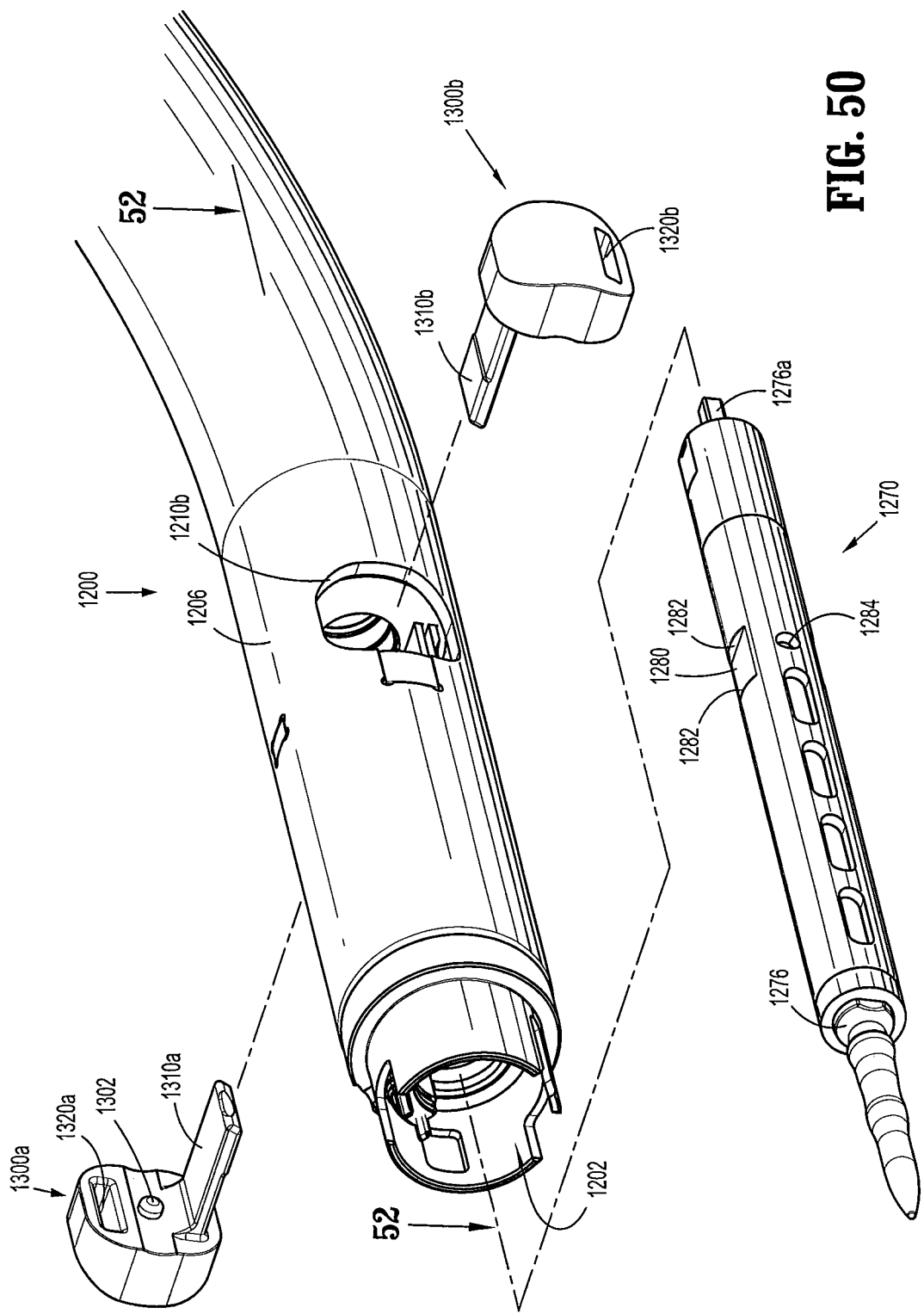
FIG. 50 is a perspective view, with parts separated, of a distal end of the adapter assembly of FIG. 1 in accordance with embodiments of the present disclosure.

With reference to FIGS. 50-52, an alternate embodiment of a trocar assembly 1270 is shown in combination with an alternate embodiment of an extension assembly 1200. Trocar assembly 1270 is similar to trocar assembly 270 described above, and not all similarities will be discussed herein. However, while trocar assembly 270 is configured for secure engagement to link assembly 277 of extension assembly 200, trocar assembly 1270 is configured for releasable engagement with extension assembly 1200.

With particular reference to FIG. 50, trocar assembly 1270 includes a pair of flattened portions 1280 about its perimeter, and extension assembly 1200 includes a pair of openings 1210a, 1210b through its outer wall or sleeve 1206 (opening 1210a is not visible in FIG. 50). When trocar assembly 1270 is engaged with extension assembly 1200, flattened portions 1280 of trocar assembly 1270 are axially aligned with openings 1210a, 1210b of extension assembly 1200. In this position, a pair of retention members 1300a, 1300b is insertable through respective openings 1210a, 1210b and adjacent (e.g., in contact with) flattened portions 1280.

More particularly, each retention member 1300a, 1300b includes an extension portion 1310a, 1310b and a receptacle 1320a, 1320b, respectively. Each extension portion 1310a, 1310b is configured to releasably engage receptacle 1320a, 1320b of the opposite retention member 1300a, 1300b. That is, extension portion 1310a of retention member 1300a is configured to releasably engage receptacle 1320b of retention member 1300b; extension portion 1310b of retention member 1300b is configured to releasably engage receptacle 1320a of retention member 1300a. It is envisioned that extension portions 1310a, 1310b respectively engage receptacles 1320b, 1320a via a snap-fit connection. It is further envisioned that retention member 1300a is identical to retention member 1300b, which may be helpful to minimize manufacturing costs and to facilitate assembly.

In use, to engage trocar assembly 1270 with extension assembly 1200, trocar assembly 1270 is inserted through a distal opening 1202 of extension assembly 1200 until a proximal end 1276a of a drive screw 1276 of trocar assembly 1200 engages a link assembly of trocar assembly 1200 (see link assembly 277 of trocar assembly 270 in FIG. 32, for example). Next, extension portion 1310a, 1310b of each retention member 1300a, 1300b, respectively, is inserted through respective opening 1210a, 1210b of outer sleeve 1206, across flattened portion 1280 of trocar assembly 1270 and into receptacle 1320b, 1320a of the other retention member 1300b, 1300a, respectively. That is, extension portion 1310a of retention member 1300a is inserted through opening 1210a (or 1210b) of outer sleeve 1206, across flattened portion 1280 and into receptacle 1320b of retention member 1300b, and extension portion 1310b of retention member 1300b is inserted through opening 1210b (or 1210a) of outer sleeve 1206, across flattened portion 1280 and into receptacle 1320a of retention member 1300a. The engagement between extension portion 1310a, flattened portion 1280 and receptacle 1320b, and the engagement between extension portion 1310b, flattened portion 1280 and receptacle 1320a is configured to prevent longitudinal translation of a trocar member 1274 of trocar assembly 1270 with respect to outer sleeve 1206 of trocar assembly 1200 (e.g., due to the engagement between extension portions 1310a, 1310b and walls 1282 of flattened portion 1280). Additionally, the engagement between extension portion 1310a, flattened portion 1280 and receptacle 1320b, and the engagement between extension portion 1310b, flattened portion 1280 and receptacle 1320a is configured to prevent relative rotation between trocar member 1274 of trocar assembly 1270 and outer sleeve 1206 of trocar assembly 1200.

Additionally, and with particular reference to FIG. 50, each retention member 1300a, 1300b includes a nub 1302 (only nub 1302 associated with retention member 1300a is shown), which is configured to mechanically engage a detent 1284 of trocar assembly 1270. It is envisioned that the engagement between nubs 1302 and detents 1284 helps maintain the proper alignment and/or orientation between retention members 1300a, 1300b and trocar assembly 1270.

To disengage retention members 1300a, 1300b from each other, it is envisioned that a user can use a tool (e.g., a screwdriver-type tool) to push extension portions 1310a, 1310b out of receptacles 1320b, 1320a, respectively. It is also envisioned that retention members 1300a, 1300b are configured to be tool-lessly disengaged from each other and from trocar assembly 1270. Disengagement of retention members 1300a, 1300b allows trocar assembly 1270 to be removed from outer sleeve 1206 of trocar assembly 1200 (e.g., for replacement or cleaning). It is envisioned that cleaning can occur by inserting a cleaning device at least partially within at least one opening 1210*a*, 1210*b* of outer sleeve 1206 of extension assembly 1200, and directing a cleaning fluid (e.g., saline) proximally and/or distally to help flush out any contaminants that may be present within outer sleeve 1206, for example.

Additionally, while extension assembly 1200 and trocar assembly 1270 are shown used in connection with adapter assembly 100, the present disclosure also envisions the use of extension assembly 1200 and/or trocar assembly 1270 with a surgical instrument (e.g., a circular stapling instrument) without the use of an adapter assembly.

Figure 53:
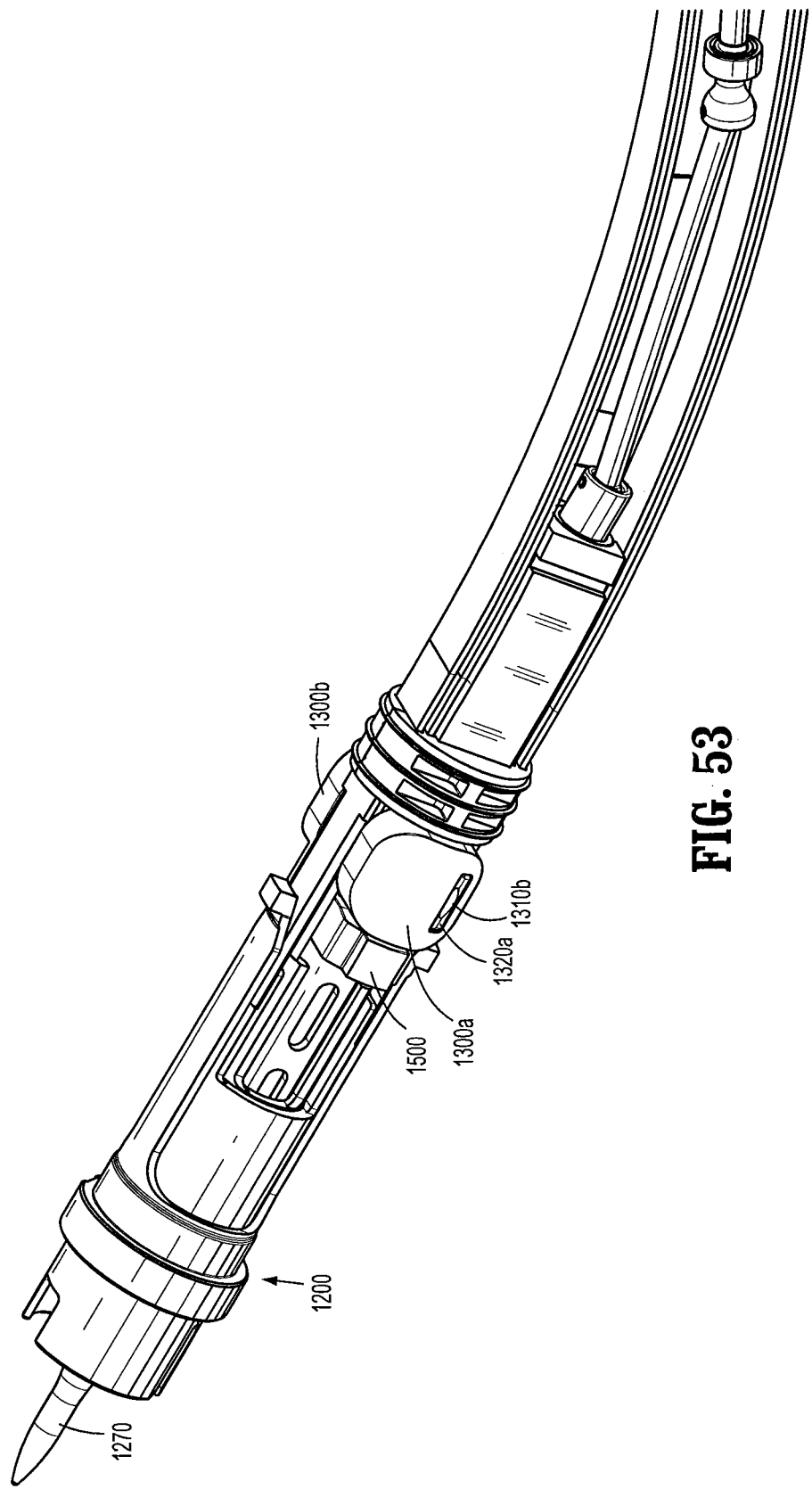

With reference to FIGS. 53-55, the present disclosure also includes a strain gauge 1500, a position sensor 1520, and a memory sensor 1540 (e.g., an E-PROM (erasable programmable read-only memory) sensor). With particular reference to FIG. 55, it is envisioned that a flexible cable 1600 extends between strain gauge 1500, position sensor 1520, memory sensor 1540 and a printed circuit board (not shown), and from the printed circuit board to an electrical connector disposed at proximal portion 302 of adapter assembly 300, for example.

It is envisioned that strain gauge 1500 is used to detect an axial load exerted on the tissue during clamping of tissue. Here, it is envisioned that if this load is too great, or exceeds a predetermined value, the user (or stapling device 10 itself) may abort the stapling operation or may choose to use a different stapling device 10 or adapter assembly 100, for example.

It is envisioned that position sensor 1520 is used to detect the axial position of the fasteners during the stapling process (e.g., when the fasteners are being ejected from adapter assembly 100). It is further envisioned that memory sensor 1540 is configured to recognize the size and/or type of staple cartridge that is engaged with adapter assembly 100 that is engaged with stapling device 10 and to relay this information to handle housing 12 of stapling device 10.

Any of the components described herein may be fabricated from either metals, plastics, resins, composites or the like taking into consideration strength, durability, wearability, weight, resistance to corrosion, ease of manufacturing, cost of manufacturing, and the like.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed:

1. An adapter assembly for operably connecting an end effector to a surgical instrument, the adapter assembly comprising:
   an elongated portion;
   a trocar assembly configured for releasable engagement with the elongated portion;
   a first retention member configured to releasably couple the trocar assembly with the elongated portion; and
   a second retention member configured to contact the trocar assembly and configured to selectively engage the first retention member.

2. The adapter assembly according to claim 1, wherein the first retention member is configured to engage a first flat portion of the trocar assembly.

3. The adapter assembly according to claim 2, wherein the second retention member is configured to engage a second flat portion of the trocar assembly.

4. The adapter assembly according to claim 1, wherein the first retention member includes a nub configured to releasably engage a first detent of the trocar assembly.

5. The adapter assembly according to claim 4, wherein the second retention member includes a nub configured to releasably engage a second detent of the trocar assembly.

6. The adapter assembly according to claim 1, wherein a portion of the first retention member is insertable at least partially within a receptacle of the second retention member.

7. The adapter assembly according to claim 6, wherein a portion of the second retention member is insertable at least partially within a receptacle of the first retention member.

8. The adapter assembly according to claim 1, wherein the first retention member is movable through a first opening of the elongated portion.

9. The adapter assembly according to claim 8, wherein the elongated portion defines a longitudinal axis, and wherein the first retention member is movable in a direction perpendicular to the longitudinal axis through the first opening of the elongated portion and into engagement with the trocar assembly.

10. The adapter assembly according to claim 9, wherein the second retention member is movable through a second opening of the elongated portion.

11. The adapter assembly according to claim 10, wherein the second retention member is movable in a direction perpendicular to the longitudinal axis through the second opening of the elongated portion and into engagement with the trocar assembly.

12. The adapter assembly according to claim 1, wherein the elongated portion defines a longitudinal axis, wherein a portion of the first retention member is configured to move from a first lateral side of the longitudinal axis, through a first opening of the elongated portion, and to a second lateral side of the longitudinal axis, and wherein a portion of the second retention member is configured to move from the second lateral side of the longitudinal axis, through a second opening of the elongated portion, and to the first lateral side of the longitudinal axis.

13. A surgical instrument, comprising:
   a handle assembly;
   an elongated portion extending distally from the handle assembly and defining a longitudinal axis;
   a trocar assembly configured for releasable engagement with the elongated portion;
   a first retention member configured to releasably couple the trocar assembly with the elongated portion; and
   a second retention member configured to engage the first retention member and the trocar assembly.

14. The surgical instrument according to claim 13, wherein the first retention member is configured to engage a first flat portion of the trocar assembly.

15. The surgical instrument according to claim 14, wherein the first retention member includes a nub configured to releasably engage a first detent of the trocar assembly.

16. The surgical instrument according to claim 13, wherein a portion of the first retention member is insertable at least partially within a receptacle of the second retention member.

17. The surgical instrument according to claim 16, wherein a portion of the second retention member is insertable at least partially within a receptacle of the first retention member.

18. The surgical instrument according to claim 13, wherein the first retention member is movable in a direction perpendicular to the longitudinal axis through a first opening of the elongated portion and into engagement with the trocar assembly.

19. The surgical instrument according to claim 13, wherein a portion of the first retention member is configured to move from a first lateral side of the longitudinal axis, through a first opening of the elongated portion, and to a second lateral side of the longitudinal axis.

20. An adapter assembly for operably connecting an end effector to a surgical instrument, the adapter assembly comprising:
- an elongated portion defining a longitudinal axis;
- a trocar assembly configured for releasable engagement with the elongated portion;
- a first retention member configured to releasably couple the trocar assembly with the elongated portion, a portion of the first retention member configured to move from a first lateral side of the longitudinal axis, through a first opening of the elongated portion, and to a second lateral side of the longitudinal axis; and
- a second retention member configured to engage the first retention member.

\* \* \* \* \*